US009825237B2

(12) United States Patent
Takada et al.

(10) Patent No.: US 9,825,237 B2
(45) Date of Patent: Nov. 21, 2017

(54) ORGANIC ELECTROLUMINESCENT ELEMENT, COMPOUND FOR ORGANIC ELECTROLUMINESCENT ELEMENT, AND LIGHT-EMITTING DEVICE, DISPLAY DEVICE, AND ILLUMINATION DEVICE USING SAID ELEMENT

(75) Inventors: Saki Takada, Kanagawa (JP); Koji Takaku, Kanagawa (JP); Tetsu Kitamura, Kanagawa (JP); Toshihiro Ise, Kanagawa (JP); Wataru Sotoyama, Kanagawa (JP)

(73) Assignee: UDC Ireland Limited, Dublin (IE)

( * ) Notice: Subject to any disclaimer, the term of this patent is extended or adjusted under 35 U.S.C. 154(b) by 887 days.

(21) Appl. No.: 14/238,367

(22) PCT Filed: Aug. 6, 2012

(86) PCT No.: PCT/JP2012/069948
§ 371 (c)(1),
(2), (4) Date: May 13, 2014

(87) PCT Pub. No.: WO2013/024730
PCT Pub. Date: Feb. 21, 2013

(65) Prior Publication Data
US 2014/0291652 A1    Oct. 2, 2014

(30) Foreign Application Priority Data

Aug. 18, 2011  (JP) ................... 2011-179173
Oct. 14, 2011  (JP) ................... 2011-226619

(51) Int. Cl.
*H01L 51/54*    (2006.01)
*C09K 11/06*    (2006.01)
(Continued)

(52) U.S. Cl.
CPC ........ *H01L 51/0071* (2013.01); *C07D 209/80* (2013.01); *C07D 221/18* (2013.01);
(Continued)

(58) Field of Classification Search
CPC .. C07D 209/80; C07D 209/82; C07D 221/00; C07D 221/18; C07D 235/00;
(Continued)

(56) References Cited

U.S. PATENT DOCUMENTS

2011/0114889 A1* 5/2011 Buesing ............... C07C 13/62
252/301.16

FOREIGN PATENT DOCUMENTS

JP    2006512395    4/2006
JP    2010205986    9/2010
(Continued)

OTHER PUBLICATIONS

Machine translation of JP2010-205986. Date of publication: Sep. 16, 2010.*
(Continued)

*Primary Examiner* — Andrew K Bohaty
(74) *Attorney, Agent, or Firm* — Riverside Law LLP

(57) ABSTRACT

An organic electroluminescent element using a compound represented by the following general formula (I) emits dark
(Continued)

blue light and has small changes in the chromaticity and in the driving voltage even after driving for a long period of time:

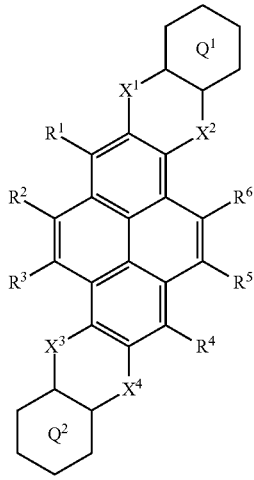

wherein $R^1$ to $R^6$; $Q^1$ and $Q^2$; $X^1$, $X^2$, $X^3$ and $X^4$ are as defined herein.

24 Claims, 1 Drawing Sheet

(51) Int. Cl.
| | |
|---|---|
| H01L 51/00 | (2006.01) |
| C07D 307/93 | (2006.01) |
| C07D 221/18 | (2006.01) |
| C07D 471/16 | (2006.01) |
| C07D 491/06 | (2006.01) |
| C07D 209/80 | (2006.01) |
| C07D 235/18 | (2006.01) |
| C07D 519/00 | (2006.01) |
| H01L 51/50 | (2006.01) |

(52) U.S. Cl.
CPC ......... *C07D 235/18* (2013.01); *C07D 307/93* (2013.01); *C07D 471/16* (2013.01); *C07D 491/06* (2013.01); *C07D 519/00* (2013.01); *C09K 11/06* (2013.01); *H01L 51/006* (2013.01); *H01L 51/0051* (2013.01); *H01L 51/0054* (2013.01); *H01L 51/0061* (2013.01); *H01L 51/0067* (2013.01); *H01L 51/0068* (2013.01); *H01L 51/0072* (2013.01); *H01L 51/0073* (2013.01); *H01L 51/0094* (2013.01); *C09K 2211/104* (2013.01); *C09K 2211/1007* (2013.01); *C09K 2211/1029* (2013.01); *C09K 2211/1033* (2013.01); *C09K 2211/1037* (2013.01); *C09K 2211/1044* (2013.01); *C09K 2211/1048* (2013.01); *C09K 2211/1059* (2013.01); *C09K 2211/1088* (2013.01); *C09K 2211/1096* (2013.01); *H01L 51/5012* (2013.01)

(58) Field of Classification Search
CPC .. C07D 235/18; C07D 307/00; C07D 307/93; C07D 471/00; C07D 471/02; C07D 471/04; C07D 471/06; C07D 471/08; C07D 471/12; C07D 471/14; C07D 471/16; C07D 471/22; C07D 491/00; C07D 491/02; C07D 491/04; C07D 491/06; C07D 491/12; C07D 519/00; C09K 11/06; C09K 2211/00; C09K 2211/10; C09K 2211/1007; C09K 2211/1018; C09K 2211/1022; C09K 2211/1029; C09K 2211/1033; C09K 2211/1037; C09K 2211/104; C09K 2211/1044; C09K 2211/1048; C09K 2211/1059; C09K 2211/1088; C09K 2211/1096; H01L 51/0032; H01L 51/005; H01L 51/0051; H01L 51/0052; H01L 51/0054; H01L 51/0059; H01L 51/006; H01L 51/0061; H01L 51/0062; H01L 51/0065; H01L 51/0067; H01L 51/0068; H01L 51/0071; H01L 51/0072; H01L 51/0073; H01L 51/0074; H01L 51/0094; H01L 51/50; H01L 51/5012
USPC ....... 428/690, 691, 917, 411.4, 336; 427/58, 427/66; 313/500–512; 257/40, 88–104, 257/E51.001–E51.052; 252/301.16–301.35; 544/245, 229; 546/30, 31, 14; 548/417, 406, 407; 549/456, 41, 214; 556/406
See application file for complete search history.

(56) References Cited

FOREIGN PATENT DOCUMENTS

| | | | |
|---|---|---|---|
| KR | 20110006915 | | 1/2011 |
| KR | 20110041726 | | 4/2011 |
| KR | 20110041726 A | * | 4/2011 |
| WO | 2010012328 | | 2/2010 |

OTHER PUBLICATIONS

Machine translation of KR2011-041726. Date of publication: Apr. 22, 2011.*

* cited by examiner

ORGANIC ELECTROLUMINESCENT ELEMENT, COMPOUND FOR ORGANIC ELECTROLUMINESCENT ELEMENT, AND LIGHT-EMITTING DEVICE, DISPLAY DEVICE, AND ILLUMINATION DEVICE USING SAID ELEMENT

CROSS-REFERENCE TO RELATED APPLICATIONS

This application is a national stage entry of International Patent Application No. PCT/JP2012/069948, filed 6 Aug. 2012, which in turn claims priority to, and the benefit of, Japanese Patent Application Nos. 2011-179173, filed 18 Aug. 2011, and 2011-226619, filed 14 Oct. 2011, all of which are incorporated herein by reference in their entireties.

TECHNICAL FIELD

The present invention relates to an organic electroluminescent element, and a material compound for an organic electroluminescent element used therefor. The present invention further relates to a light emitting device, a display device, or an illumination device, using the organic electroluminescent element.

BACKGROUND ART

Since organic electroluminescent elements (which may hereinafter also be referred to as "elements" or "organic EL elements") are capable of high-luminance light emitting using low voltage driving, they have been actively researched and developed. The organic electroluminescent elements have an organic layer between a pair of electrodes, and utilize, for light emitting, energy of the exciton generated as a result of recombination of the electron injected from a cathode and the hole injected from an anode in the organic layer. Since The organic electroluminescent elements can be provided as an element having diverse light emitting wavelengths, and have a high response speed and are relatively thin and light-weight, it is expected that they can be employed in a wide range of applications. Above all, it is important to develop the development of an organic electroluminescent element having high color purity and luminous efficiency is important in applications with full-color displays and the like, and the results of studies on various research and development have been reported.

PTL 1 describes that it is possible to attain light emission and a longer service life in the blue region of an element using a material in which a ring is formed with a single bond and a methylene chain with respect to a fused ring structure such as pyrene as a fluorescent material. In Examples of this literature, 3 kinds of compounds are used as a blue dopant which has a chromaticity of about (0.14 or 0.16) and a maximum efficiency of about 7.8 cd/A, described in Table 6.

Furthermore, the literature 2 which is well-known, describes that an element having high efficiency and a wide gap (that is, considered to allow blue light emission to be performed) is obtained by using a molecule formed by subjecting benzofluorene to ring fusion and expansion as a light emitting material. In Examples of this literature, the spectrum of the element thus fabricated is disclosed, in which the wavelength is in a long and broad wave form and the maximum light emitting wavelength was about 462 nm on average.

In addition, PTLs 3 and 4 disclose a material in which two indole rings are fused symmetrically at 1-, 2-, 6-, and 7-positions of a pyrene ring, but according to the investigation of the present inventors, it has been found that there are problems, for example, that the material has an insufficient blue color purity and a change in the chromaticity due to deterioration by driving with a lowered luminous intensity (hereinafter also referred to as a change in the driving chromaticity), and has an increase in the voltage by driving (hereinafter also referred to as an increase in the driving voltage).

CITATION LIST

Patent Literature
[PTL 1] WO2010/012328
[PTL 2] JP-T-2006-512395
[PTL 3] KR20110006915A
[PTL 4] KR20110041726A

SUMMARY OF INVENTION

Technical Problem

However, the present inventors have investigated, and as a result, they have found that the chromaticity of the organic electroluminescent elements described in PTLs 1 and 2 above may still be insufficient for dark blue colors in display applications or the like, and there is a further need for achieving darker blue light emission. In addition, it has been found that when these organic electroluminescent elements are driven for a long period of time, a change in the chromaticity occurs together with an increase in the driving voltage.

The present invention aims to solve the foregoing problems. That is, it is an object of the present invention to provide an organic electroluminescent element which emits dark blue light and has small changes in the chromaticity and in the driving voltage even after driving for a long period of time.

Solution to Problem

Therefore, the present inventors have conducted extensive investigations for the purpose of providing an organic electroluminescent element which emits dark blue light and is driven at a low voltage even after driving for a long period of time.

Here, PTL 1 mentions a position of a pyrene skeleton to which a non-aromatic ring is fused, and this literature describes that rings are preferably fused in the major axis direction of the pyrene (1-, 2-, 3-, 6-, 7-, and 8-positions), but does not specifically describe the reason or the detailed mechanism thereof. On the other hand, PTL 2 does not describe a good position to which a pyrene skeleton is fused, as seen from the use of an exemplary compound having a structure having non-aromatic rings fused so as to connect the major axis direction and the minor axis direction (4-, 5-, 9-, and 10-positions) of two molecules of pyrene in [0119].

Therefore, at that time, it could not be expected from the knowledge in the related art whether or not a material for an organic electroluminescent element which emits dark blue light and has a low voltage after a long-term driving can be obtained by changing the structure of a pyrene-based compound.

In this regard, the present inventors have found that by using a pyrene-based compound in a specific structure having a ring fused in a specific direction as a light emitting dopant for an element, an organic electroluminescent element which emits dark blue light and is driven at a low voltage even after driving for a long period of time can be obtained, which could not have been achieved in the related art. They have further found that the skeleton of such a compound having the structure itself emits short-wavelength light and it is not necessary to shorten the wavelength by additionally introducing a substituent having a specific structure into the skeleton as in the fluorescent light emitting materials known in the related art.

That is, the present inventors have found that by using a pyrene derivative having a specific structure, the aforementioned problems can be solved, thereby providing the present invention as described below.

[1] An organic electroluminescent element including:
a substrate,
a pair of electrodes including an anode and a cathode, disposed on the substrate, and
at least one organic layer including a light emitting layer, disposed between the electrodes,
in which at least one kind of compound represented by the following general formula (I) is contained in any layer of the at least one organic layer.

General formula (I)

[Chem. 1]

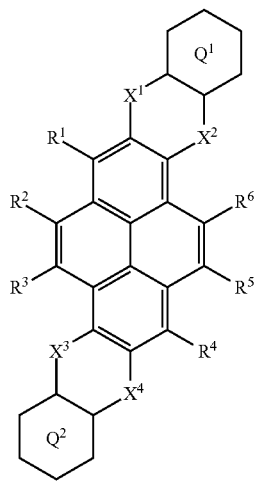

[In the general formula (I), $R^1$ to $R^6$ each independently represent a hydrogen atom or a substituent, but there is no case where two adjacent groups out of $R^1$ to $R^6$ are bonded to each other to form a ring. $Q^1$ and $Q^2$ each independently represent a 6-membered aromatic ring or a 6-membered nitrogen-containing aromatic heterocycle. A ring may be further fused with the 6-membered ring represented by $Q^1$ and $Q^2$. Among $X^1$ to $X^4$, $X^1$ and $X^4$ represent a single bond, and $X^2$ and $X^3$ each independently represent a linking group represented by any one of $CR^{51}R^{52}$, $NR^{53}$, O, S, and $SiR^{54}R^{55}$, or $X^2$ and $X^3$ represent a single bond, and $X^1$ and $X^4$ each independently represent a linking group represented by any one of $CR^{51}R^{52}$, $NR^{53}$, O, S, and $SiR^{54}R^{55}$. $R^{51}$ to $R^{55}$ each independently represent a hydrogen atom or a substituent. The general formula (I) satisfies at least one of the following conditions 1 and 2.

(Condition 1) The number of carbon atoms constituting the 6-membered aromatic ring or the 6-membered nitrogen-containing aromatic heterocycle of $Q^1$ and the number of carbon atoms constituting the 6-membered aromatic ring or the 6-membered nitrogen-containing aromatic heterocycle of $Q^2$ are different from each other.

(Condition 2) The linking group represented by one of $X^1$ and $X^2$ and the linking group represented by one of $X^3$ and $X^4$ are different from each other.]

[2] The organic electroluminescent element as described in [1], in which the compound represented by the general formula (I) is a compound represented by the following general formula (II-1).

[Chem. 2]

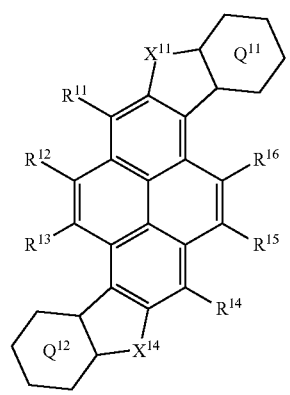

General formula (II-1)

[In the general formula (II-1), $R^{11}$ to $R^{16}$ each independently represent a hydrogen atom or a substituent, but there is no case where two adjacent groups out of $R^{11}$ to $R^{16}$ are bonded to each other to form a ring. $Q^{11}$ and $Q^{12}$ each independently represent a 6-membered aromatic ring or a 6-membered nitrogen-containing aromatic heterocycle. A ring may be further fused with the 6-membered ring represented by $Q^{11}$ and $Q^{12}$. $X^{11}$ and $X^{14}$ each independently represent a linking group represented by any one of $CR^{51}R^{52}$, $NR^{53}$, O, S, and $SiR^{54}R^{55}$. $R^{51}$ to $R^{55}$ each independently represent a hydrogen atom or a substituent. The general formula (II-1) satisfies at least one of the following conditions 1 and 2.

(Condition 1) The number of carbon atoms constituting the 6-membered aromatic ring or the 6-membered nitrogen-containing aromatic heterocycle of $Q^{11}$ and the number of carbon atoms constituting the 6-membered aromatic ring or the 6-membered nitrogen-containing aromatic heterocycle of $Q^{12}$ are different from each other.

(Condition 2) The linking group represented by $X^{11}$ and the linking group represented by $X^{14}$ are different from each other.]

[3] The organic electroluminescent element as described in [2], in which the compound represented by the general formula (II-1) is a compound represented by the following general formula (II-2).

General formula (II-2)

[Chem. 3]

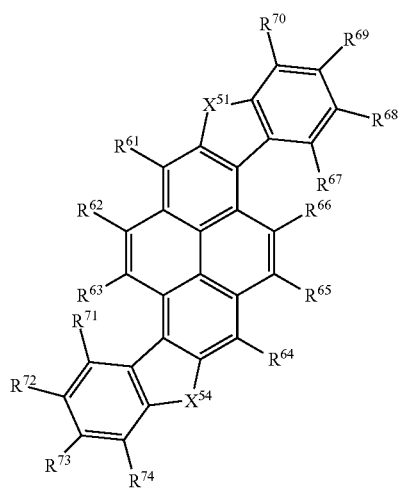

[In the general formula (II-2), $R^{61}$ to $R^{66}$ each independently represent a hydrogen atom or a substituent, but there is no case where two adjacent groups out of $R^{61}$ to $R^{66}$ are bonded to each other to form a ring. $R^{67}$ to $R^{74}$ each independently represent a hydrogen atom or a substituent, two adjacent groups out of $R^{67}$ to $R^{74}$ may be bonded to each other to form a ring structure, but the number of the rings thus formed is 2 or less. $X^{51}$ and $X^{54}$ each independently represent a linking group represented by any one of $CR^{51}R^{52}$, $NR^{53}$, O, S, and $SiR^{54}R^{55}$. $R^{51}$ to $R^{55}$ each independently represent a hydrogen atom or a substituent. The linking group represented by $X^{51}$ and the linking group represented by $X^{54}$ are different from each other.]

The organic electroluminescent element as described in [3], in which in the general formula (II-2), $X^{51}$ and $X^{54}$ each independently represent a linking group represented by any one of $CR^{51}R^{52}$, $NR^{53}$, and O.

[5] The organic electroluminescent element as described in [3] or [4], in which in the general formula (II-2), any one of $X^{51}$ and $X^{54}$ is $NR^{53}$, and the other is a linking group represented by any one of $CR^{51}R^{52}$ and O.

[6] The organic electroluminescent element as described in any one of [3] to [5], in which in the general formula (II-2), at least one of $R^{61}$ to $R^{74}$ and $R^{51}$ to $R^{55}$ is a substituent having any one of a fluorine atom, an alkyl group, a silyl group, an amino group, and a phenyl group or nitrogen-containing aromatic 6-membered ring having these groups.

[7] The organic electroluminescent element as described in [1], in which the compound represented by the general formula (I) is a compound represented by the following general formula (III-1).

[Chem. 4]

General formula (III-1)

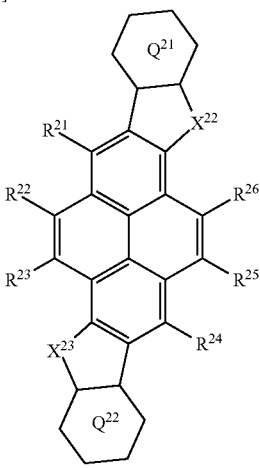

[In the general formula (III-1), $R^{21}$ to $R^{26}$ each independently represent a hydrogen atom or a substituent, but there is no case where two adjacent groups out of $R^{21}$ to $R^{25}$ are bonded to each other to form a ring. $Q^{21}$ and $Q^{22}$ each independently represent a 6-membered aromatic ring or a 6-membered nitrogen-containing aromatic heterocycle. A ring may be further fused with the 6-membered ring represented by $Q^{21}$ and $Q^{22}$. $X^{22}$ and $X^{23}$ each independently represent a linking group represented by any one of $CR^{51}R^{52}$, $NR^{53}$, O, S, and $SiR^{54}R^{55}$. $R^{51}$ to $R^{55}$ each independently represent a hydrogen atom or a substituent. The general formula (III-1) satisfies at least one of the following conditions 1 and 2.

(Condition 1) The number of carbon atoms constituting the 6-membered aromatic ring or the 6-membered nitrogen-containing aromatic heterocycle of $Q^{21}$ and the number of carbon atoms constituting the 6-membered aromatic ring or the 6-membered nitrogen-containing aromatic heterocycle of $Q^{22}$ are different from each other.

(Condition 2) The linking group represented by $X^{22}$ and the linking group represented by $X^{23}$ are different from each other.]

[8] The organic electroluminescent element as described in [7], in which the compound represented by the general formula (III-1) is a compound represented by the following general formula (III-2).

General formula (III-2)

[Chem. 5]

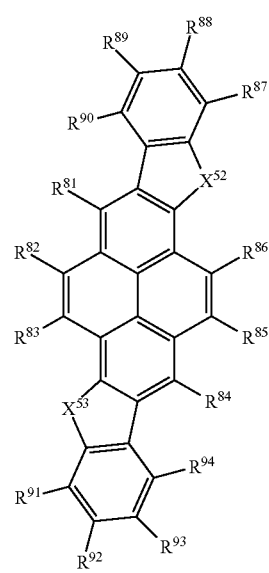

[In the general formula (III-2), $R^{81}$ to $R^{86}$ each independently represent a hydrogen atom or a substituent, but there is no case where two adjacent groups out of $R^{61}$ to $R^{66}$ are bonded to each other to form a ring. $R^{87}$ to $R^{94}$ each independently represent a hydrogen atom or a substituent, two adjacent groups out of $R^{87}$ to $R^{94}$ may be bonded to each other to form a ring structure, but the number of the rings thus formed is 2 or less. $X^{51}$ and $X^{54}$ each independently represent a linking group represented by any one of $CR^{51}R^{52}$, $NR^{53}$, O, S, and $SiR^{54}R^{55}$. $R^{51}$ to $R^{55}$ each independently represent a hydrogen atom or a substituent. The linking group represented by $X^{52}$ and the linking group represented by $X^{53}$ are different from each other.]

The organic electroluminescent element as described in [8], in which in the general formula (III-2), $X^{52}$ and $X^{53}$ each independently represent a linking group represented by any one of $CR^{51}R^{52}$, $NR^{53}$, and O.

[10] The organic electroluminescent element as described in [8] or [9], in which in the general formula (III-2), any one of $X^{52}$ and $X^{53}$ is a linking group represented by $NR^{53}$, and the other is a linking group represented by any one of $CR^{51}R^{52}$ and O.

[11] The organic electroluminescent element as described in any one of [8] to [10], in which in the general formula (III-2), at least one of $R^{81}$ to $R^{94}$ and $R^{51}$ to $R^{55}$ is a substituent having any one of a fluorine atom, an alkyl group, a silyl group, an amino group, and a phenyl group or nitrogen-containing aromatic 6-membered ring having these groups.

[12] The organic electroluminescent element as described in [1], in which the compound represented by the general formula (I) is a compound represented by the following general formula (IV).

[Chem. 6]

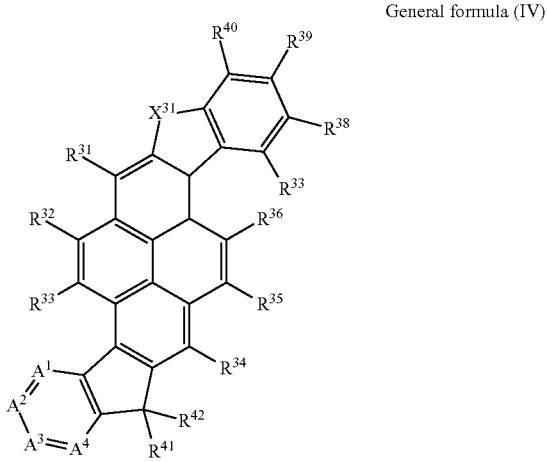

General formula (IV)

[In the general formula (IV), $R^{31}$ to $R^{36}$ each independently represent a hydrogen atom or a substituent, but there is no case where two adjacent groups out of $R^{31}$ to $R^{36}$ are bonded to each other to form a ring. $R^{37}$ to $R^{40}$ each independently represent a hydrogen atom or a substituent, two adjacent groups out of $R^{37}$ to $R^{40}$ may be bonded to each other to form a ring structure, but the number of the rings thus formed is 2 or less. $R^{41}$ and $R^{42}$ each independently represent a hydrogen atom or a substituent. $A^1$ to $A^4$ each independently represent $CR^{56}$ or N, and at least one of $A^1$ to $A^4$ represents N. $R^{56}$ represents a hydrogen atom or a substituent, when two adjacent groups out of $A^1$ to $A^4$ are $CR^{56}$, the two $R^{56}$'s may be bonded to each other to form a ring structure, but the number of the rings thus formed is 2 or less. $X^{31}$ represents a linking group represented by any one of $NR^{53}$, O, S, and $SiR^{54}R^{55}$. $R^{53}$ to $R^{55}$ each independently represent a hydrogen atom or a substituent.]

[13] The organic electroluminescent element as described in any one of [1] to [12], in which the molecular weight of the compound represented by the general formula (I) is 800 or less.

[14] The organic electroluminescent element as described in any one of [1] to [13], in which the compound represented by the general formula (I) is contained in the light emitting layer.

[15] The organic electroluminescent element as described in [14], in which the compound represented by the general formula (I) is a light emitting material contained in the light emitting layer.

[16] The organic electroluminescent element as described in [15], in which the light emitting layer further contains a host material.

[17] The organic electroluminescent element as described in [16], in which the host material has a hydrocarbon fused ring structure having 10 to 50 carbon atoms.

[18] The organic electroluminescent element as described in [16], in which the host material has an anthracene skeleton.

[19] The organic electroluminescent element as described in any one of [1] to [18], in which the organic layer containing the compound represented by the general formula (I) is formed by a vacuum decomposition process.

[20] The organic electroluminescent element as described in any one of [1] to [18], in which the light emitting layer is formed by a wet process.

[21] A light emitting device using the organic electroluminescent element as described in any one of [1] to [20].

A display device using the organic electroluminescent element as described in any one of [1] to [20].

[23] An illumination device using the organic electroluminescent element as described in any one of [1] to [20].

[24] A compound represented by the following general formula (I).

[Chem. 7]

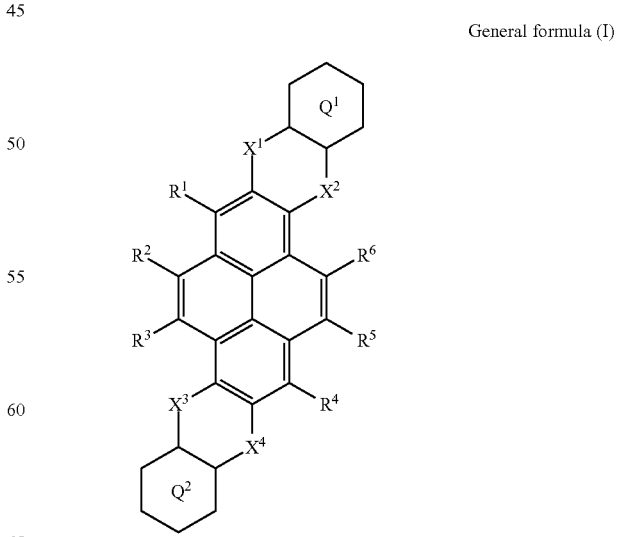

General formula (I)

[In the general formula (I), $R^1$ to $R^6$ each independently represent a hydrogen atom or a substituent, but there is no case where two adjacent groups out of $R^1$ to $R^6$ are bonded to each other to form a ring. $Q^1$ and $Q^2$ each independently represent a 6-membered aromatic ring or a 6-membered nitrogen-containing aromatic heterocycle. A ring may be further fused with the 6-membered ring represented by $Q^1$ and $Q^2$. Among $X^1$ to $X^4$, $X^1$ and $X^4$ represent a single bond, and $X^2$ and $X^3$ each independently represent a linking group represented by any one of $CR^{51}R^{52}$, $NR^{53}$, O, S, and $SiR^{54}R^{55}$, or $X^2$ and $X^3$ represent a single bond, and $X^1$ and $X^4$ each independently represent a linking group represented by any one of $CR^{51}R^{52}$, $NR^{53}$, O, S, and $SiR^{54}R^{55}$. $R^{51}$ to $R^{55}$ each independently represent a hydrogen atom or a substituent. The general formula (I) satisfies at least one of the following conditions 1 and 2.

(Condition 1) The number of carbon atoms constituting the 6-membered aromatic ring or the 6-membered nitrogen-containing aromatic heterocycle of $Q^1$ and the number of carbon atoms constituting the 6-membered aromatic ring or the 6-membered nitrogen-containing aromatic heterocycle of $Q^2$ are different from each other.

(Condition 2) The linking group represented by one of $X^1$ and $X^2$ and the linking group represented by one of $X^3$ and $X^4$ are different from each other.]

Advantageous Effects of Invention

The organic electroluminescent element of the present invention has advantageous effects in that it emits dark blue light and is driven at a low voltage even after a long period of time. Further, when the material for an organic electroluminescent element of the present invention is used, such an excellent organic electroluminescent element can be easily prepared. In addition, the light emitting device, the display device, and the illumination device of the present invention has advantageous effects in that the power consumption is low and the chromaticity is excellent, and is particularly suitable in display applications.

DESCRIPTION OF EMBODIMENTS

Figure 1:
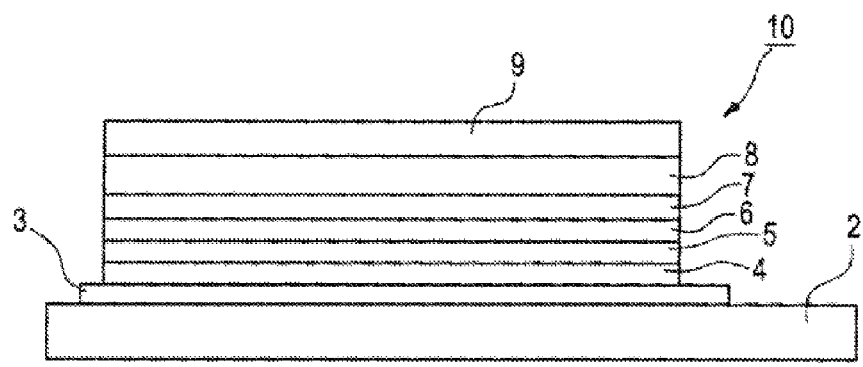
FIG. 1 is a schematic view showing one example of a configuration of an organic electroluminescent element according to the present invention.

Hereinafter, the details of the present invention will be described. The description of the requirements of the configuration as described below is based on representative embodiments and specific examples of the present invention, but the present invention is not limited to these embodiments and specific examples. Incidentally, in the present specification, the range expressed with "to" means a range including the numerical values before and after "to" as the lower limit and the upper limit, respectively.

[Light Emitting Material for Organic Electroluminescent Element, Represented by General Formula (I)]

The organic electroluminescent element of the present invention has at least a substrate, a pair of electrodes including an anode and a cathode, disposed on the substrate, and at least one organic layer including a light emitting layer, disposed between the electrodes. The organic electroluminescent element of the present invention contains at least one kind of compound represented by the following general formula (I) in any organic layers.

[Chem. 8]

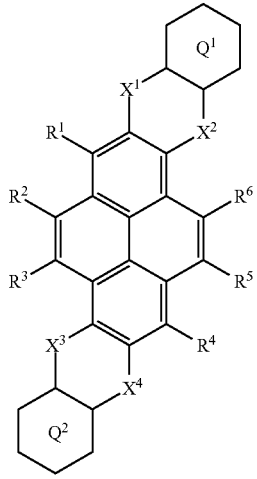

General formula (I)

In the general formula (I), $R^1$ to $R^6$ each independently represent a hydrogen atom or a substituent, but there is no case where two adjacent groups out of $R^1$ to $R^6$ are bonded to each other to form a ring. $Q^1$ and $Q^2$ each independently represent a 6-membered aromatic ring or a 6-membered nitrogen-containing aromatic heterocycle. A ring may be further fused with the 6-membered ring represented by $Q^1$ and $Q^2$. For $X^1$ to $X^4$, $X^1$ and $X^4$ represent a single bond, and $X^2$ and $X^3$ each independently represent a linking group represented by any one of $CR^{51}R^{52}$, $NR^{53}$, O, S, and $SiR^{54}R^{55}$, or $X^2$ and $X^3$ represent a single bond, and $X^1$ and $X^4$ each independently represent a linking group represented by any one of $CR^{51}R^{52}$, $NR^{53}$, O, S, and $SiR^{54}R^{55}$. $R^{51}$ to $R^{55}$ each independently represent a hydrogen atom or a substituent. The general formula (I) satisfies at least one of the following conditions 1 and 2.

(Condition 1) The number of carbon atoms constituting the 6-membered aromatic ring or the 6-membered nitrogen-containing aromatic heterocycle of $Q^1$ and the number of carbon atoms constituting the 6-membered aromatic ring or the 6-membered nitrogen-containing aromatic heterocycle of $Q^2$ are different from each other.

(Condition 2) The linking group represented by one of $X^1$ and $X^2$ and the linking group represented by one of $X^3$ and $X^4$ are different from each other.]

In the organic electroluminescent element of the present invention, the compound for an organic electroluminescent element, represented by the general formula (I) (hereinafter also referred to as a light emitting material represented by the general formula (I), the light emitting material of the present invention, or the compound of the present invention) is used as a light emitting material.

By using the light emitting material of the present invention, dark blue light emission can be obtained. This is presumed to be due to the fact that the symmetry of the molecule is reduced by winding the rings asymmetrically with respect to the center of pyrene to inhibit the association among the molecules, in addition to the molecular conjugation length or the molecular length contributing to electronic transition becoming suitable.

Furthermore, in the present invention, it is found that the light emitting material can not only exhibit good blue light emission, but also inhibit a change in the chromaticity after driving and an increase in the voltage during deterioration of decomposition. This is presumed to be due to the fact that since the light emitting material has a structure in which molecules are less accessible to each other, the molecules decomposed by driving (which is presumed to be due to the fact that the low-energy gap decomposed products of the molecules trap charges or the decomposed high-energy gap products interfere with charge transporting) prevent local aggregation.

On the other hand, if an organic electroluminescent element is fabricated using a pyrene-based compound in the related art and used for a long period of time, the chromaticity is changed due to deterioration by driving with a lowered luminous intensity. It is thought that the causes of the change in the chromaticity involved in such a deterioration by driving are a change in the light emitting positions due to a change in the element charge balance and optical interference therefrom, formation of association among pyrene rings by heat generation involved in driving, or the like, production of light emitting components by chemical reaction deterioration of the light emitting materials or host materials by element driving, or the like. As a result, in order to prevent a change in the chromaticity involved in deterioration by driving, it is necessary to provide materials which are insusceptible to any of those events. The compound represented by the general formula (I) of the present invention is stable against holes (oxidation) or electrons (reduction) and has a high charge injecting or transporting property. With the compound, formation of association among the pyrene rings does not easily occur and the chemical reaction deterioration by element driving does not easily occur. As a result, the change in the chromaticity involved in deterioration by driving does not easily occur, either. In addition, since the compound represented by the general formula (I) of the present invention is insusceptible to association among the pyrene rings, it can form a light emitting layer alone without the use of a host material.

Moreover, since the compound represented by the general formula (I) has a structure in which molecules are less accessible to each other, is stable against holes (oxidation) or electrons (reduction), and is insusceptible to chemical reaction deterioration by element driving, it can not only exhibit good blue light emission, but also inhibit an increase in the voltage during decomposition deterioration.

Specifically, the light emitting material for an organic electroluminescent element, represented by the general formula (I), contributes to shortening of the wavelength and inhibition of a change in the chromaticity during driving and an increase in the voltage during deterioration of decomposition in its mother skeleton. In this regard, the light emitting material represented by the general formula (I) is not limited in the substituent of the mother skeleton and provides the effects as described above. However, in a preferred aspect of the present invention, shortening of the wavelength and inhibition of an increase in the voltage during deterioration of decomposition may be promoted by using a specific substituent.

Hereinbelow, the light emitting material represented by the general formula (I) will be described in detail.

In the general formula (I), $Q^1$ and $Q^2$ each independently represent a 6-membered monocyclic aromatic ring or a 6-membered monocyclic nitrogen-containing aromatic heterocycle. In the case where they represent a 6-membered nitrogen-containing aromatic heterocycle, one to four members out of atoms constituting the ring skeleton are preferably hetero atoms, one to three members out of atoms constituting the ring skeleton are more preferably hetero atoms, and one or two members out of atoms constituting the ring skeleton are still more preferably hetero atoms. Examples of the hetero atom include a nitrogen atom, an oxygen atom, and a sulfur atom, but preferably a nitrogen atom.

To the 6-membered aromatic ring and the 6-membered nitrogen-containing aromatic heterocycle, a hydrogen atom or a substituent is bonded. Specific examples of the substituent include the following Substituent Group A; preferably an alkyl group (more preferably a linear, branched, or cyclic alkyl group having 1 to 10 carbon atoms), an aryl group (more preferably an aryl group having 6 to 14 carbon atoms), a heteroaryl group (preferably a heteroaryl group having 5 to 20 carbon atoms and containing anyone of N, O, and S as a hetero atom), a di-substituted amino group (more preferably a dialkylamino group or a diarylamino group; the preferred ranges of the alkyl and the aryl in this case are the same as the preferred ranges of the alkyl and the aryl as described above), a halogeno group (preferably a fluoro group), a cyano group, and a nitro group. Further, the substituent may be further substituted with any one or more substituents and the preferred range of the substituent in this case is the same as the definition as described above. The substituents may be bonded to each other to form a ring structure, and a structure in which a ring is further fused to the 6-membered aromatic ring and the 6-membered nitrogen-containing aromatic heterocycle may be formed. Here, it is preferable that the substituents bonded to an adjacent ring-constituting atom be bonded to each other to form a ring structure. The ring thus formed may be any one of an aromatic ring, a heterocycle, and a non-aromatic ring, and preferably an aromatic ring such as a benzene ring.

For $X^2$ to $X^4$ in the general formula (I), $X^1$ and $X^4$ represent a single bond, and $X^2$ and $X^3$ each independently represent a linking group represented by any one of $CR^{51}R^{52}$, $NR^{53}$, O, S, and $SiR^{54}R^{55}$, or $X^2$ and $X^3$ represent a single bond, and $X^1$ and $X^4$ each independently represent a linking group represented by any one of $CR^{51}R^{52}$, $NR^{53}$, O, S, and $SiR^{54}R^{55}$. In the case where they represent a linking group, from the viewpoint of a more preferred light emission color, they are preferably $CR^{51}R^{52}$ or $NR^{53}$.

$R^{51}$ to $R^{55}$ each independently represent a hydrogen atom or a substituent. Examples of $R^{51}$, $R^{52}$, $R^{54}$ and $R^{55}$ include the following Substituent Group A and examples of $R^{53}$ include the following Substituent Group B.

<<Substituent Group A (Substituent on Carbon Atom and Substituent Group on Silicon Atom)>>

An alkyl group (preferably having 1 to 30 carbon atoms, more preferably having 1 to 20 carbon atoms, and particularly preferably having 1 to 10 carbon atoms; for example, methyl, ethyl, isopropyl, t-butyl, n-octyl, n-decyl, n-hexadecyl, cyclopropyl, cyclopentyl, and cyclohexyl), an alkenyl group (preferably having 2 to 30 carbon atoms, more preferably having 2 to 20 carbon atoms, and particularly preferably having 2 to 10 carbon atoms; for example, vinyl, allyl, 2-butenyl, and 3-pentenyl), an alkynyl group (preferably having 2 to 30 carbon atoms, more preferably having 2 to 20 carbon atoms, and particularly preferably having 2 to 10 carbon atoms; for example, propargyl and 3-pentynyl), an aryl group (preferably having 6 to 30 carbon atoms, more preferably having 6 to 20 carbon atoms, and particularly preferably having 6 to 12 carbon atoms; for example, phenyl, p-methylphenyl, naphthyl, anthranyl), amino group (preferably having 0 to 30 carbon atoms, more preferably having 0 to 20 carbon atoms, and particularly preferably having 0 to 10 carbon atoms; for example, amino, methylamino, dimethylamino, diethylamino, dibenzylamino, diphenylamino, and ditolylamino), an alkoxy group (preferably having 1 to 30 carbon atoms, more preferably having 1 to 20 carbon atoms, and particularly preferably having 1 to 10 carbon atoms; for example, methoxy, ethoxy, butoxy, and 2-ethylhexyloxy), and aryloxy group (preferably having 6 to 30 carbon atoms, more preferably having 6 to 20 carbon atoms, and particularly preferably having 6 to 12 carbon atoms; for example, phenyloxy, 1-naphthyloxy, and 2-naphthyloxy), a heterocyclic oxy group (preferably having 1 to 30 carbon atoms, more preferably having 1 to 20 carbon atoms, and particularly preferably having 1 to 12 carbon atoms; for example, pyridyloxy, pyrazyloxy, pyrimidyloxy, and quinolyloxy), an acyl group (preferably having 2 to 30 carbon atoms, more preferably having 2 to 20 carbon atoms, and particularly preferably having 2 to 12 carbon atoms; for example, acetyl, benzoyl, formyl, and pivaloyl), an alkoxycarbonyl group (preferably having 2 to 30 carbon atoms, more preferably having 2 to 20 carbon atoms, and particularly preferably having 2 to 12 carbon atoms; for example, methoxycarbonyl and ethoxycarbonyl), an aryloxycarbonyl group (preferably having 7 to 30 carbon atoms, more preferably having 7 to 20 carbon atoms, and particularly preferably having 7 to 12 carbon atoms; for example, phenyloxycarbonyl), an acyloxy group (preferably having 2 to 30 carbon atoms, more preferably having 2 to 20 carbon atoms, and particularly preferably having 2 to 10 carbon atoms; for example, acetoxy and benzoyloxy), an acylamino group (preferably having 2 to 30 carbon atoms, more preferably having 2 to 20 carbon atoms, and particularly preferably having 2 to 10 carbon atoms; for example, acetylamino and benzoylamino), an alkoxycarbonylamino group (preferably having 2 to 30 carbon atoms, more preferably having 2 to 20 carbon atoms, and particularly preferably having 2 to 12 carbon atoms; for example, methoxycarbonylamino), an aryloxycarbonylamino group (preferably having 7 to 30 carbon atoms, more preferably having 7 to 20 carbon atoms, and particularly preferably having 7 to 12 carbon atoms; for example, phenyloxycarbonylamino), a sulfonylamino group (preferably having 1 to 30 carbon atoms, more preferably having 1 to 20 carbon atoms, and particularly preferably having 1 to 12 carbon atoms; for example, methanesulfonylamino and benzenesulfonylamino), a sulfamoyl group (preferably having 0 to 30 carbon atoms, more preferably having 0 to 20 carbon atoms, and particularly preferably having 0 to 12 carbon atoms; for example, sulfamoyl, methylsulfamoyl, dimethylsulfamoyl, and phenylsulfamoyl), a carbamoyl group (preferably having 1 to 30 carbon atoms, more preferably having 1 to 20 carbon atoms, and particularly preferably having 1 to 12 carbon atoms; for example, carbamoyl, methylcarbamoyl, diethylcarbamoyl, and phenylcarbamoyl), an alkylthio group (preferably having 1 to 30 carbon atoms, more preferably having 1 to 20 carbon atoms, and particularly preferably having 1 to 12 carbon atoms; for example, methylthio and ethylthio), an arylthio group (preferably having 6 to 30 carbon atoms, more preferably having 6 to 20 carbon atoms, and particularly preferably having 6 to 12 carbon atoms; for example, phenylthio), a heterocyclic thio group (preferably having 1 to 30 carbon atoms, more preferably having 1 to 20 carbon atoms, and particularly preferably having 1 to 12 carbon atoms; for example, pyridylthio, 2-benzoimizolylthio, 2-benzoxazolylthio, and 2-benzothiazolylthio), a sulfonyl group (preferably having 1 to 30 carbon atoms, more preferably having 1 to 20 carbon atoms, and particularly preferably having 1 to 12 carbon atoms; for example, mesyl and tosyl), a sulfinyl group (preferably having 1 to 30 carbon atoms, more preferably having 1 to 20 carbon atoms, and particularly preferably having 1 to 12 carbon atoms; for example, methanesulfinyl and benzenesulfinyl), a ureido group (preferably having 1 to 30 carbon atoms, more preferably having 1 to 20 carbon atoms, and particularly preferably having 1 to 12 carbon atoms; for example, ureido, methylureido, and phenylureido), phosphoramide group (preferably having 1 to 30 carbon atoms, more preferably having 1 to 20 carbon atoms, and particularly preferably having 1 to 12 carbon atoms; for example, diethylphosphoramide and phenylphosphoramide), a hydroxy group, a mercapto group, a halogen atom (for example, a fluorine atom, a chlorine atom, a bromine atom, and an iodine atom), a cyano group, a sulfo group, a carboxyl group, a nitro group, a hydroxamic group, a sulfino group, a hydrazino group, an imino group, a heterocyclic group (inclusive of an aromatic heterocyclic group, which preferably has 1 to 30 carbon atoms, and more preferably 1 to 12 carbon atoms and in which examples of the hetero atom include a nitrogen atom, an oxygen atom, a sulfur atom, a phosphorus atom, a silicon atom, a selenium atom, and a tellurium atom; and specific examples thereof include pyridyl, pyrazinyl, pyrimidyl, pyridazinyl, pyrrolyl, pyrazolyl, triazolyl, imidazolyl, oxazolyl, triazolyl, isoxazolyl, isothiazolyl, quinolyl, furyl, thienyl, selenophenyl, tellurophenyl, piperidyl, piperidino, morpholino, pyrrolidyl, pyrrolidino, benzoxazolyl, benzoimidazolyl, benzothiazolyl, a carbazolyl group, an azepinyl group, and a silolyl group), a silyl group (preferably having 3 to 40 carbon atoms, more preferably having 3 to 30 carbon atoms, and particularly preferably having 3 to 24 carbon atoms; for example, trimethylsilyl and triphenylsilyl), a silyloxy group (preferably having 3 to 40 carbon atoms, more preferably having 3 to 30 carbon atoms, and particularly preferably having 3 to 24 carbon atoms; for example, trimethylsilyloxy and triphenylsilyloxy), and a phosphoryl group (for example, a diphenylphosphoryl group and a dimethylphosphoryl group). These substituents may be further substituted, and examples of the additional substituent include the groups selected from the Substituent Group A as described above. Further, the substituent substituted with a substituent may be further substituted, and examples of the additional substituent include the groups selected from the Substituent Group A as described above. In addition, the substituent substituted with the substituent substituted with a substituent may be further substituted, and examples of the additional substituent include the groups selected from the Substituent Group A as described above.

<<Substituent Group B (Substituent Group on Nitrogen Atom)>>

An alkyl group (preferably having 1 to 30 carbon atoms, more preferably having 1 to 20 carbon atoms, and particularly preferably having 1 to 10 carbon atoms; for example, methyl, ethyl, isopropyl, t-butyl, n-octyl, n-decyl, n-hexadecyl, cyclopropyl, cyclopentyl, and cyclohexyl), an alkenyl group (preferably having 2 to 30 carbon atoms, more preferably having 2 to 20 carbon atoms, and particularly preferably having 2 to 10 carbon atoms; for example, vinyl, allyl, 2-butenyl, and 3-pentenyl), an alkynyl group (preferably having 2 to 30 carbon atoms, more preferably having 2 to 20 carbon atoms, and particularly preferably having 2 to 10 carbon atoms; for example, propargyl and 3-pentynyl), an aryl group (preferably having 6 to 30 carbon atoms, more preferably having 6 to 20 carbon atoms, and particularly preferably having 6 to 12 carbon atoms; for example, phenyl, p-methylphenyl, naphthyl, and anthranyl), a cyano group, and a heterocyclic group (inclusive of an aromatic heterocyclic group, which preferably has 1 to 30 carbon atoms, and more preferably 1 to 12 carbon atoms and in which examples of the hetero atom include a nitrogen atom, an oxygen atom, a sulfur atom, a phosphorus atom, a silicon atom, a selenium atom, and a tellurium atom; and specific examples thereof include pyridyl, pyrazinyl, pyrimidyl, pyridazinyl, pyrrolyl, pyrazolyl, triazolyl, imidazolyl, oxazolyl, triazolyl, isoxazolyl, isothiazolyl, quinolyl, furyl, thienyl, selenophenyl, tellurophenyl, piperidyl, piperidino, morpholino, pyrrolidyl, pyrrolidino, benzoxazolyl, benzoimidazolyl, benzothiazolyl, a carbazolyl group, an azepinyl group, and a silolyl group). These substituents may be further substituted, and examples of the additional substituent include the groups selected from the Substituent Group B as described above. Further, the substituent substituted with a substituent may be further substituted, and examples of the additional substituent include the groups selected from the Substituent Group B as described above. In addition, the substituent substituted with the substituent substituted with a substituent may be further substituted, and examples of the additional substituent include the groups selected from the Substituent Group B as described above.

$R^{51}$, $R^{52}$, $R^{54}$ and $R^{55}$ preferably represent an alkyl group (more preferably a linear, branched, or cyclic alkyl group having 1 to 10 carbon atoms), an aryl group (more preferably an aryl group having 6 to 14 carbon atoms), or a heteroaryl group (preferably a heteroaryl group having 5 to 20 carbon atoms and containing anyone of N, O, and S as a hetero atom). Among these, a linear or branched alkyl group having 1 to 6 carbon atoms, and an aryl group having 6 to 10 carbon atoms are more preferred. In addition, from the viewpoint of easiness of synthesis, it is preferable that $R^{51}$ and $R^{52}$ be the same as each other.

$R^{53}$ is preferably any one of a linear, branched, or cyclic alkyl group having 1 to 10 carbon atoms, an aryl group having 6 to 50 carbon atoms, or a heteroaryl group having 5 to 20 carbon atoms and containing any one or more of N, O, and S as a hetero atom, and more preferably any one of an aryl group having 6 to 14 carbon atoms and a heteroaryl group having 5 to 20 carbon atoms and containing any one or more of N, O, and S as a hetero atom.

It is preferable that the compound represented by the general formula (I) have any one of a fluorine atom, an alkyl group, a silyl group, an amino group, and a phenyl group or nitrogen-containing aromatic 6-membered ring having these groups in the molecule from the viewpoint of inhibition of association light emission. Particularly preferred specific examples of a fluorine atom, an alkyl group, a silyl group, an amino group, and a phenyl group or nitrogen-containing aromatic 6-membered ring containing these groups in the molecule are shown below, but the present invention is not limited thereto.

[Chem. 9]

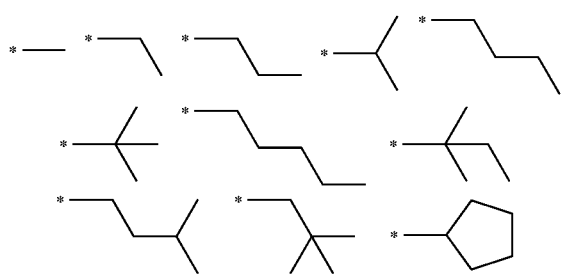

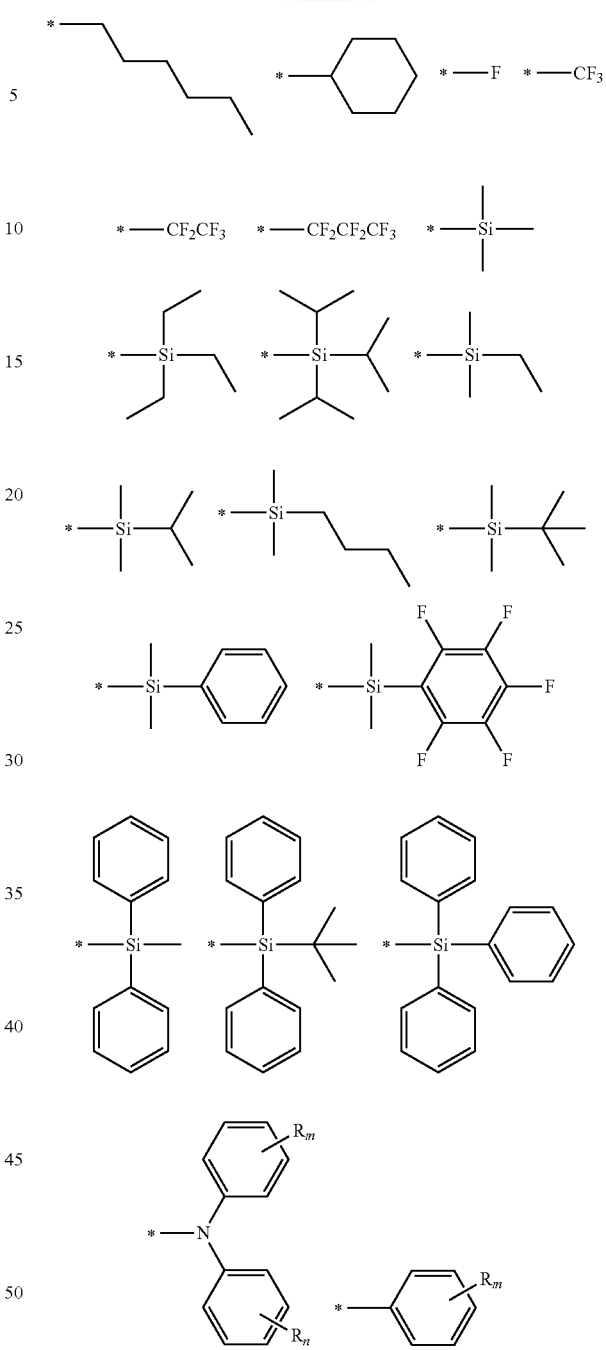

[Chem. 10]

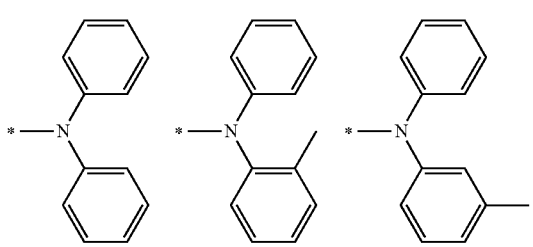

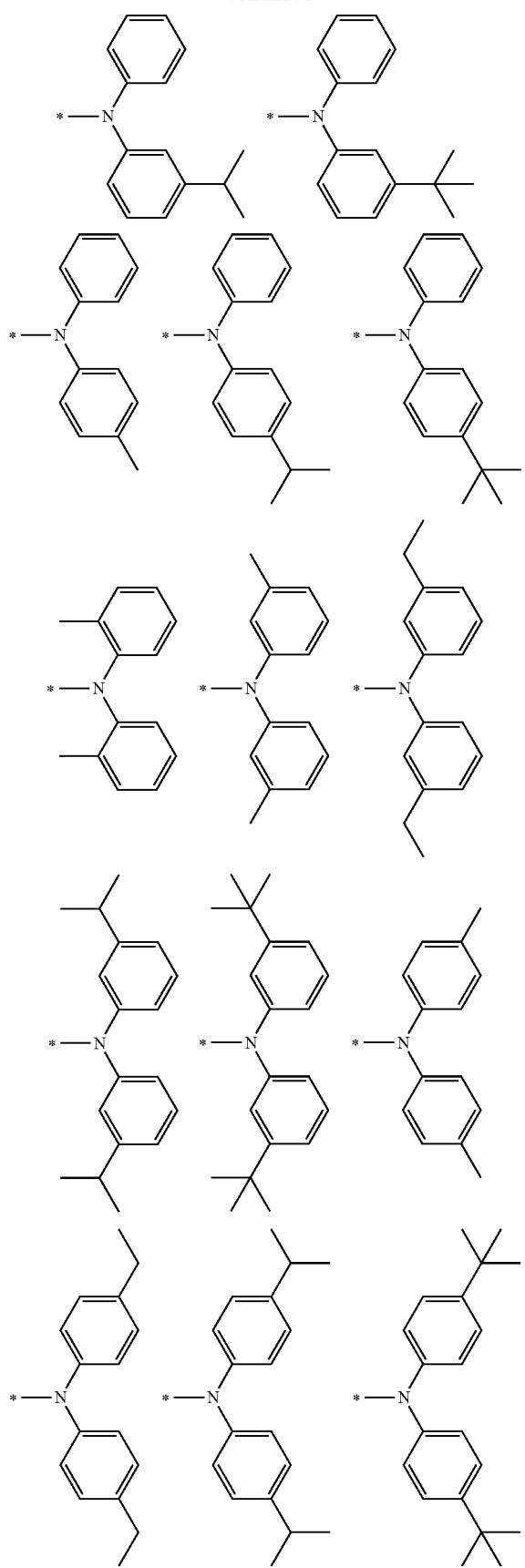
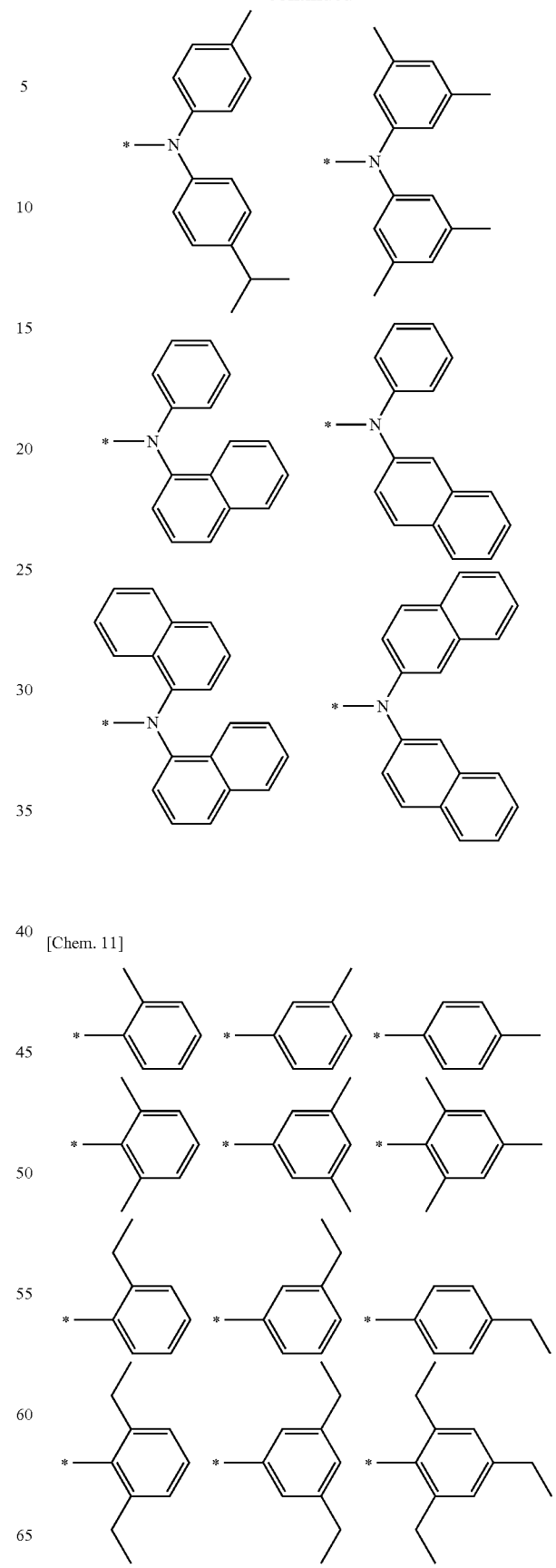
[Chem. 11]

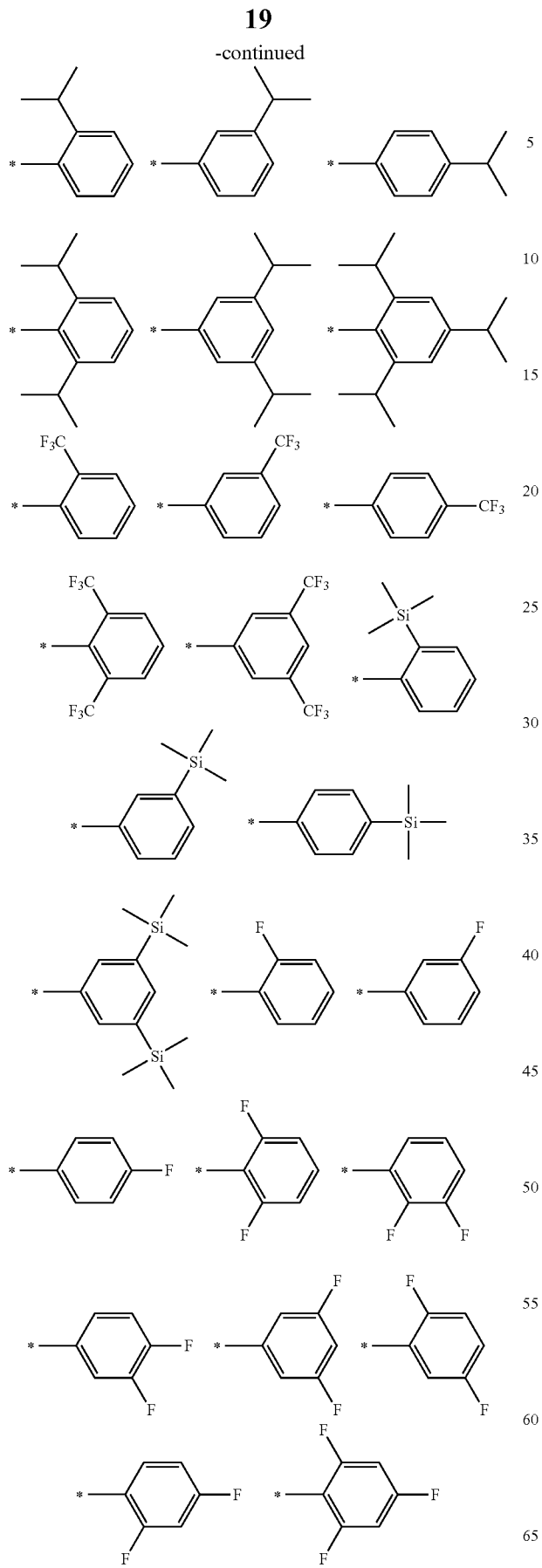
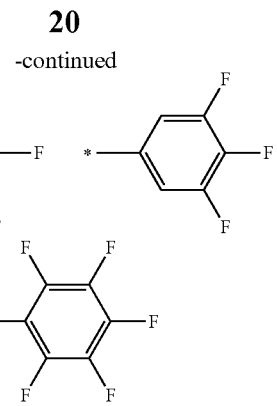

The compound represented by the general formula (I) satisfies at least one of the following conditions 1 and 2.

(Condition 1) The number of carbon atoms constituting the 6-membered aromatic ring or the 6-membered nitrogen-containing aromatic heterocycle of $Q^1$ and the number of carbon atoms constituting the 6-membered aromatic ring or the 6-membered nitrogen-containing aromatic heterocycle of $Q^2$ are different from each other.

(Condition 2) The linking group represented by one of $X^1$ and $X^2$ and the linking group represented by one of $X^3$ and $X^4$ are different from each other.

The number of carbon atoms mentioned in the condition 1 is the number of carbon atoms constituting the ring skeleton of the 6-membered aromatic ring or the number of carbon atoms constituting the ring skeleton of the 6-membered nitrogen-containing aromatic heterocycle, but not carbon atoms constituting the ring skeleton of the entire fused ring formed by the mutual bonding of a plurality of substituents bonding to these rings. In the case where the compound represented by the general formula (I) satisfies the condition 1, for example, a case where the number of carbon atoms constituting one ring of $Q^1$ and $Q^2$ is 6 and the number of carbon atoms constituting the other ring is 5 (for example, a benzene ring and a pyridine ring); a case where the number of carbon atoms constituting one ring is 6 and the number of carbon atoms constituting the other ring is 4 (for example, a benzene ring and a pyrimidine ring); and a case where the number of carbon atoms constituting one ring is 5 and the number of carbon atoms constituting the other ring is 4 (for example, a pyridine ring and a pyrimidine ring) can be exemplified. The difference in the numbers of carbon atoms constituting the rings of $Q^1$ and $Q^2$ is preferably 1 to 3, and more preferably 1 or 2.

In the case where the compound represented by the general formula (I) satisfies the condition 2, for example, for a linking group represented by one of $X^1$ and $X^2$ and a linking group represented by one of $X^3$ and $X^4$, a case where one is $CR^{51}R^{52}$ and the other is $NR^{53}$; a case where one is $CR^{51}R^{52}$ and the other is O; a case where one is $CR^{51}R^{52}$ and the other is S; a case where one is $CR^{51}R^{52}$ and the other is $SiR^{54}R^{55}$; a case where one is $NR^{53}$ the other is O; a case where one is $NR^{53}$ and the other is S; a case where one is $NR^{53}$ and the other is $SiR^{54}R^{55}$; and a case where one is O and the other is S can be exemplified. A combination of $X^1$ and $X^4$ or a combination of $X^2$ and $X^3$ preferably represents a linking group.

In the present invention, the compound satisfying both of the condition 1 and the condition 2 is more preferred, and in the case of using such a compound, the effect of the present invention can be further obtained.

In the general formula (I), $R^1$ to $R^6$ each independently represent a hydrogen atom or a substituent. As mentioned herein, examples of the substituent include the Substituent Group A as described above. $R^1$ to $R^6$ preferably represent an alkyl group (more preferably a linear, branched, or cyclic alkyl group having 1 to 10 carbon atoms), an aryl group (more preferably an aryl group having 6 to 14 carbon atoms), a heteroaryl group (preferably a heteroaryl group having 5 to 20 carbon atoms and containing any one of N, O, and S as a hetero atom), a di-substituted amino group (more preferably a dialkylamino group or a diarylamino group; the preferred range of the alkyl or aryl in this case is the same as the preferred range of the alkyl or aryl in $R^1$ to $R^8$), a halogeno group (preferably a fluoro group), a cyano group, or a nitro group. Further, such a substituent may be substituted with any one or more substituents, and the preferred range of the substituent in this case is the same as the preferred range of the substituent in $R^1$ to $R^6$.

One or more of $R^1$ to $R^6$ are preferably a substituent represented by any one of the following general formulae.

[Chem. 12]

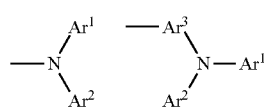

$Ar^1$ and $Ar^2$ each independently represent an aryl group, $Ar^3$ represents a divalent arylene group. $Ar^1$ and $Ar^2$ are preferably a substituted or unsubstituted phenyl or naphthyl, and more preferably a substituted or unsubstituted phenyl. $Ar^3$ is preferably a substituted or unsubstituted phenylene or naphthylene, more preferably a substituted or unsubstituted phenylene, and most preferably a substituted or unsubstituted p-phenylene.

In the present invention, $R^1$ to $R^6$ may be all hydrogen atoms. 0 to 4 groups out of $R^1$ to $R^6$ are preferably substituents, 0 to 2 groups are more preferably substituents, and 0 or 1 group are still more preferably substituents.

In the general formula (I), there is no case where $R^1$ to $R^6$ bonded to the adjacent ring skeleton atom are bonded to each other to form a ring. As used herein, the "ring" includes both of a case where an aromatic ring or a heterocycle is newly fused and a case where a non-aromatic ring is formed. As used herein, specific examples of the non-aromatic ring include the following structures.

[Chem. 13]

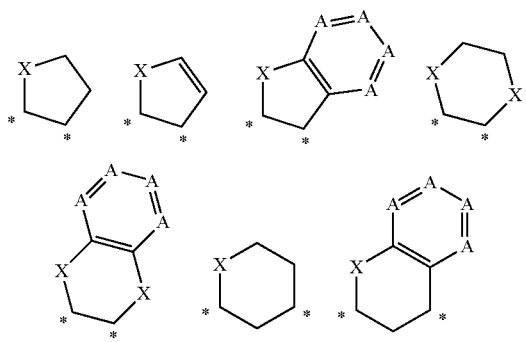

In the formulae above, X's each independently represent a hetero atom, and examples of the hetero atom include a nitrogen atom, an oxygen atom, and a sulfur atom. A's each independently represent $CR^{51}R^{52}$ or $NR^{53}$, and the definitions of $R^{51}$ to $R^{53}$ are as described above.

The light emitting material represented by the general formula (I) is preferably a compound represented by the following general formula (II-1).

[Chem. 14]

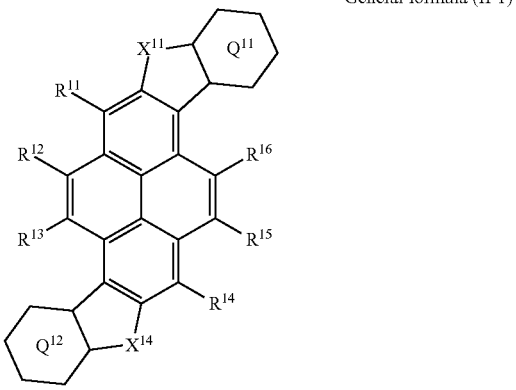

General formula (II-1)

In the general formula (II-1), $R^{11}$ to $R^{16}$ each independently represent a hydrogen atom or a substituent, but there is no case where two adjacent groups out of $R^{11}$ to $R^{16}$ are bonded to each other to form a ring. $Q^{11}$ and $Q^{12}$ each independently represent a 6-membered aromatic ring or a 6-membered nitrogen-containing aromatic heterocycle. A ring may be further fused with the 6-membered ring represented by $Q^{11}$ and $Q^{12}$. $X^{11}$ and $X^{14}$ each independently represent a linking group represented by any one of $CR^{51}R^{52}$, $NR^{53}$, O, S, and $SiR^{54}R^{55}$. $R^{51}$ to $R^{55}$ each independently represent a hydrogen atom or a substituent. The general formula (II-1) satisfies at least one of the following conditions 1 and 2.

(Condition 1) The number of carbon atoms constituting the 6-membered aromatic ring or the 6-membered nitrogen-containing aromatic heterocycle of $Q^{11}$ and the number of carbon atoms constituting the 6-membered aromatic ring or the 6-membered nitrogen-containing aromatic heterocycle of $Q^{12}$ are different from each other.

(Condition 2) The linking group represented by $X^{11}$ and the linking group represented by $X^{14}$ are different from each other.

The preferred ranges of $R^{11}$ to $R^{16}$, $Q^{11}$ and $Q^{12}$ in the general formula (II-1) are the same as the preferred ranges of $R^1$ to $R^6$, $Q^1$ and $Q^2$ in the general formula (I). Further, the preferred ranges of the linking groups represented by $X^{11}$ and $X^{14}$ in the general formula (II-1) are the same as the preferred ranges of the linking groups represented by $X^1$ to $X^4$ in the general formula (I).

The compound represented by the general formula (II-1) is preferably a compound represented by the following general formula (II-2).

General formula (II-2)

[Chem. 15]

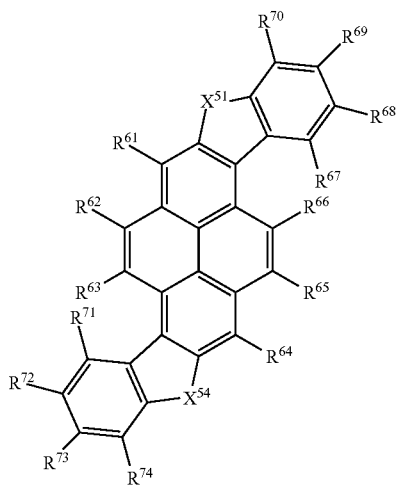

In the general formula (II-2), $R^{61}$ to $R^{66}$ each independently represent a hydrogen atom or a substituent, but there is no case where two adjacent groups out of $R^{61}$ to $R^{66}$ are bonded to each other to form a ring. $R^{67}$ to $R^{74}$ each independently represent a hydrogen atom or a substituent, two adjacent groups out of $R^{67}$ to $R^{74}$ may be bonded to each other to form a ring structure, but the number of the rings thus formed is 2 or less. $X^{51}$ and $X^{54}$ each independently represent a linking group represented by any one of $CR^{51}R^{52}$, $NR^{53}$, O, S, and $SiR^{54}R^{55}$. $R^{51}$ to $R^{55}$ each independently represent a hydrogen atom or a substituent. The linking group represented by $X^{51}$ and the linking group represented by $X^{54}$ are different from each other.

The preferred ranges of $R^{61}$ to $R^{66}$ in the general formula (II-2) are the same as the preferred ranges of $R^1$ to $R^6$ in the general formula (I). $R^{67}$ to $R^{74}$ in the general formula (II-2) can represent the substituents which $R^{61}$ to $R^{66}$ may take. In the case where two adjacent groups out of $R^{67}$ to $R^{74}$ are bonded to each other to form a ring structure, the ring structure may be any one of an aromatic ring, a heterocycle, and a non-aromatic ring. However, since the number of the rings thus formed is limited to 2 or less, the ring structure thus formed is a monocyclic structure or a bicyclic structure. Further, the preferred ranges of the linking groups represented by $X^{51}$ and $X^{54}$ in the general formula (II-2) are the same as the preferred ranges of the linking groups represented by $X^1$ to $X^4$ in the general formula (I).

Furthermore, the general formula (II-2) more preferably has the following aspects.

In the general formula (II-2), it is more preferable that $X^{51}$ and $X^{54}$ be each independently a linking group represented by any one of $CR^{51}R^{52}$, $NR^{53}$, and O, and it is particularly preferable that any one of $X^{51}$ and $X^{54}$ be $NR^{53}$ and the other be a linking group represented by any one of $CR^{51}R^{52}$ and O.

In the general formula (II-2), it is preferable that at least one of $R^{61}$ to $R^{74}$ and $R^{51}$ to $R^{55}$ be a substituent having any one of a fluorine atom, an alkyl group, a silyl group, an amino group, and a phenyl group or nitrogen-containing aromatic 6-membered ring having these groups, and examples of the substituent having any one of a fluorine atom, an alkyl group, a silyl group, and an amino group are the same as particularly preferred specific examples of a fluorine atom, an alkyl group, a silyl group, an amino group, and a phenyl group or nitrogen-containing aromatic 6-membered ring containing these groups in the molecule.

The light emitting material represented by the general formula (I) is preferably a compound represented by the following general formula (III-1).

[Chem. 16]

General formula (III-1)

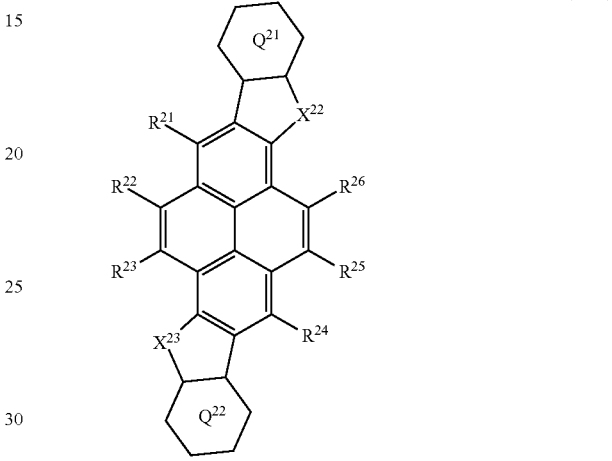

In the general formula (III-1), $R^{21}$ to $R^{26}$ each independently represent a hydrogen atom or a substituent, but there is no case where two adjacent groups out of $R^{21}$ to $R^{25}$ are bonded to each other to form a ring. $Q^{21}$ and $Q^{22}$ each independently represent a 6-membered aromatic ring or a 6-membered nitrogen-containing aromatic heterocycle. A ring may be further fused with the 6-membered ring represented by $Q^{21}$ and $Q^{22}$. $X^{22}$ and $X^{23}$ each independently represent a linking group represented by any one of $CR^{51}R^{52}$, $NR^{53}$, O, S, and $SiR^{54}R^{55}$. $R^{51}$ to $R^{55}$ each independently represent a hydrogen atom or a substituent. The general formula (III-1) satisfies at least one of the following conditions 1 and 2.

(Condition 1) The number of carbon atoms constituting the 6-membered aromatic ring or the 6-membered nitrogen-containing aromatic heterocycle of $Q^{21}$ and the number of carbon atoms constituting the 6-membered aromatic ring or the 6-membered nitrogen-containing aromatic heterocycle of $Q^{22}$ are different from each other.

(Condition 2) The linking group represented by $X^{22}$ and the linking group represented by $X^{23}$ are different from each other.

The preferred ranges of $R^{21}$ to $R^{26}$, $Q^{21}$ and $Q^{22}$ in the general formula (III-1) are the same as the preferred ranges of $R^1$ to $R^6$, $Q^1$ and $Q^2$ in the general formula (I). Further, the preferred ranges of the linking groups represented by $X^{21}$ and $X^{24}$ in the general formula (III-1) are the same as the preferred ranges of the linking groups represented by $X^1$ to $X^4$ in the general formula (I).

The compound represented by the general formula (III-1) is preferably a compound represented by the following general formula (III-2).

[Chem. 17]

General formula (III-2)

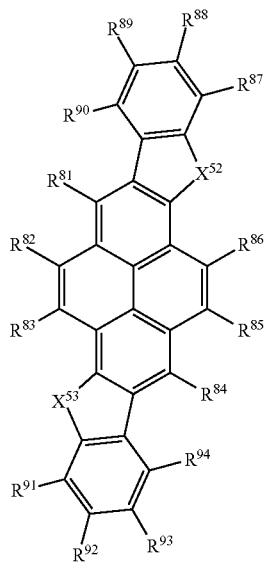

In the general formula (III-2), $R^{81}$ to $R^{86}$ each independently represent a hydrogen atom or a substituent, but there is no case where two adjacent groups out of $R^{61}$ to $R^{66}$ are bonded to each other to form a ring. $R^{87}$ to $R^{94}$ each independently represent a hydrogen atom or a substituent, two adjacent groups out of $R^{87}$ to $R^{94}$ may be bonded to each other to form a ring structure, but the number of the rings thus formed is 2 or less. $X^{51}$ and $X^{54}$ each independently represent a linking group represented by any one of $CR^{51}R^{52}$, $NR^{53}$, O, S, and $SiR^{54}R^{55}$. $R^{51}$ to $R^{55}$ each independently represent a hydrogen atom or a substituent. The linking group represented by $X^{52}$ and the linking group represented by $X^{53}$ are different from each other.

The preferred ranges of $R^{81}$ to $R^{86}$ in the general formula (III-2) are the same as the preferred ranges of $R^1$ to $R^6$ in the general formula (I). $R^{87}$ to $R^{94}$ in the general formula (II-2) can represent the substituents which $R^{81}$ to $R^{86}$ may take. In the case where two adjacent groups out of $R^{87}$ to $R^{94}$ are bonded to each other to form a ring structure, the ring structure may be any one of an aromatic ring, a heterocycle, and a non-aromatic ring. However, since the number of the rings thus formed is limited to 2 or less, the ring structure thus formed is a monocyclic structure or a bicyclic structure. Further, the preferred ranges of the linking groups represented by $X^{52}$ and $X^{53}$ in the general formula (III-2) are the same as the preferred ranges of the linking groups represented by $X^1$ to $X^4$ in the general formula (I).

Furthermore, the general formula (III-2) more preferably has the following aspects.

In the general formula (III-2), it is more preferable that $X^{51}$ and $X^{53}$ be each independently a linking group represented by any one of $CR^{51}R^{52}$, $NR^{53}$, and O, and it is particularly preferable that any one of $X^{52}$ and $X^{53}$ be $NR^{53}$ and the other be a linking group represented by any one of $CR^{51}R^{52}$ and O.

In the general formula (II-2), at least one of $R^{81}$ to $R^{94}$ and $R^{51}$ to $R^{55}$ is preferably a substituent having any one of a fluorine atom, an alkyl group, a silyl group, an amino group, and a phenyl group or nitrogen-containing aromatic 6-membered ring having these groups, and examples of the substituent having any one of a fluorine atom, an alkyl group, a silyl group, and an amino group are the same as particularly preferred specific examples of a fluorine atom, an alkyl group, a silyl group, an amino group, and a phenyl group or nitrogen-containing aromatic 6-membered ring containing these groups in the molecule.

The light emitting material represented by the general formula (I) is preferably a compound represented by the following general formula (IV).

General formula (IV)

[Chem. 18]

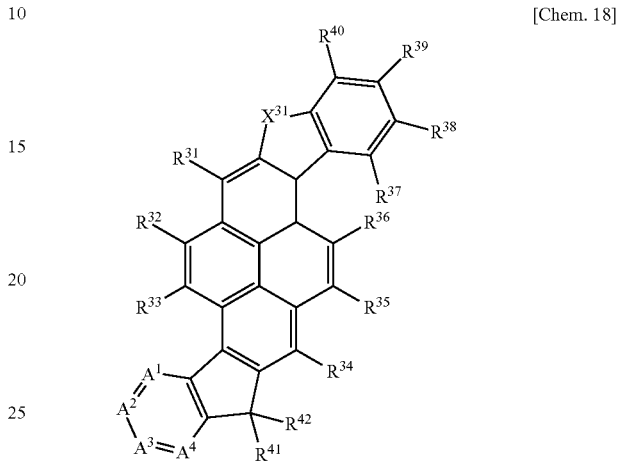

In the general formula (IV), $R^{31}$ to $R^{36}$ each independently represent a hydrogen atom or a substituent, but there is no case where two adjacent groups out of $R^{31}$ to $R^{36}$ are bonded to each other to form a ring. $R^{37}$ to $R^{40}$ each independently represent a hydrogen atom or a substituent, two adjacent groups out of $R^{37}$ to $R^{40}$ may be bonded to each other to form a ring structure, but the number of the rings thus formed is 2 or less. $R^{41}$ and $R^{42}$ each independently represent a hydrogen atom or a substituent. $A^1$ to $A^4$ each independently represent $CR^{56}$ or N, and at least one of $A^1$ to $A^4$ represents N. $R^{56}$ represents a hydrogen atom or a substituent, when two adjacent groups out of $A^1$ to $A^4$ are $CR^{56}$, the two $R^{56}$'s may be bonded to each other to form a ring structure, but the number of the rings thus formed is 2 or less. $X^{31}$ represents a linking group represented by any one of $NR^{53}$, O, S, and $SiR^{54}R^{55}$. $R^{53}$ to $R^{55}$ each independently represent a hydrogen atom or a substituent.

The preferred ranges of $R^{31}$ to $R^{36}$ in the general formula (IV) are the same as the preferred ranges of $R^1$ to $R^6$ in the general formula (I). $R^{37}$ to $R^{40}$ in the general formula (IV) can represent the substituents which $R^{31}$ to $R^{36}$ may take. In the case where two adjacent groups out of $R^{37}$ to $R^{40}$ are bonded to each other to form a ring structure, the ring structure may be any one of an aromatic ring, a heterocycle, and a non-aromatic ring. However, since the number of the rings thus formed is limited to 2 or less, the ring structure thus formed is a monocyclic structure or a bicyclic structure. $R^{41}$ and $R^{42}$ each independently represent a hydrogen atom or a substituent, and the preferred range of the substituent are the same as the preferred ranges of $R^1$ to $R^6$ in the general formula (I). The preferred ranges of the linking group represented by $X^{31}$ in the general formula (IV) are the same as the preferred ranges of the linking group represented by $X^1$ to $X^4$ in the general formula $A^1$ to $A^4$ in the general formula (IV) each independently represent $CR^{56}$ or N. In $A^1$ to $A^4$, the number of N's is preferably 0 to 2, preferably 0 or 1, and particularly preferably 0. That is, a case where $A^1$ to $A^4$ are all $CR^{56}$'s can be exemplified as a preferred case.

In $CR^{56}$, the carbon atom is a ring-constituting atom of the light emitting material represented by the general formula (I), and $R^{56}$ represents a hydrogen atom or a substituent, which is bonded to the carbon atom. Further, as used herein, the substituent includes those in which the substituent is further substituted with a substituent. Examples of $R^{56}$ include the Substituent Group A as described above. $R^{56}$ is preferably an alkyl group (more preferably a linear, branched, or cyclic alkyl group having 1 to 10 carbon atoms), an aryl group (more preferably an aryl group having 6 to 14 carbon atoms), a heteroaryl group (preferably a heteroaryl group having 5 to 20 carbon atoms and containing any one of N, O, and S as a hetero atom), a di-substituted amino group (more preferably a dialkylamino group or a diarylamino group; the preferred ranges of the alkyl group and the aryl group in this case are the same as the preferred ranges of the alkyl group and the aryl group in $R^1$), a halogeno group (preferably having a fluoro group), a cyano group, or a nitro group. Further, $R^{56}$'s bonded to the adjacent carbon atom may be bonded to each other to form a cyclic structure. Examples of such a cyclic structure include an aryl group (more preferably an aryl group having 6 to 14 carbon atoms), and a heteroaryl group (preferably a heteroaryl group having 5 to 20 carbon atoms and containing any one of N, O, and S as a hetero atom), and more preferably an aryl group.

Specific examples of the light emitting material represented by the general formula (I) are shown below, but it should not be construed that the light emitting material represented by the general formula (I) which can be used in the present invention is limited to the specific examples.

[Chem. 19]

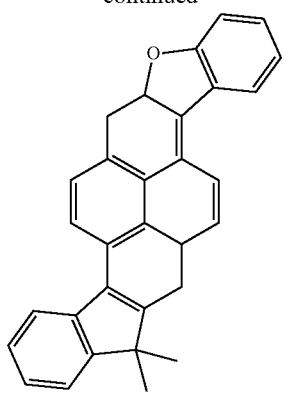

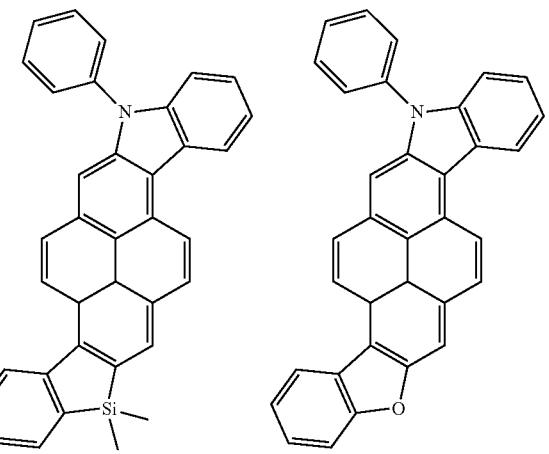

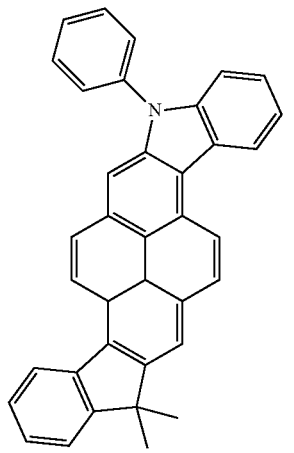

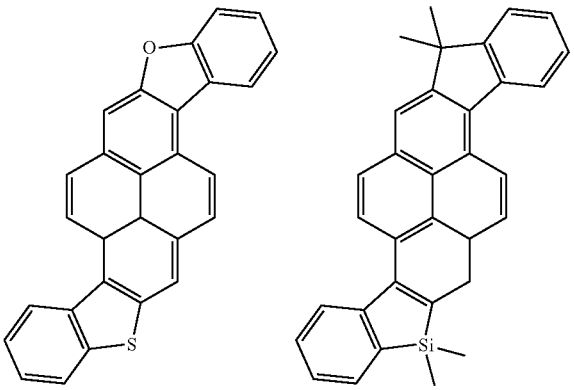

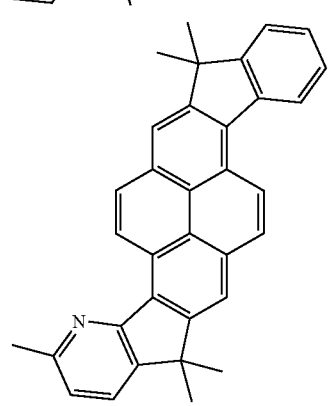

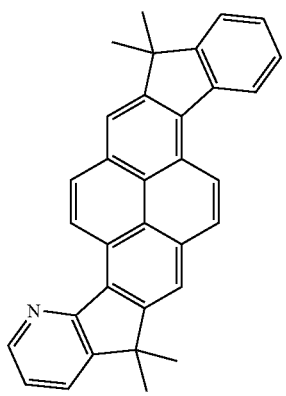

-continued
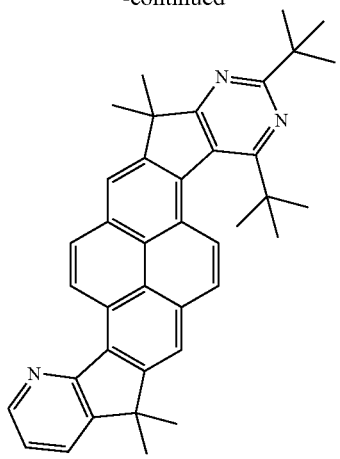
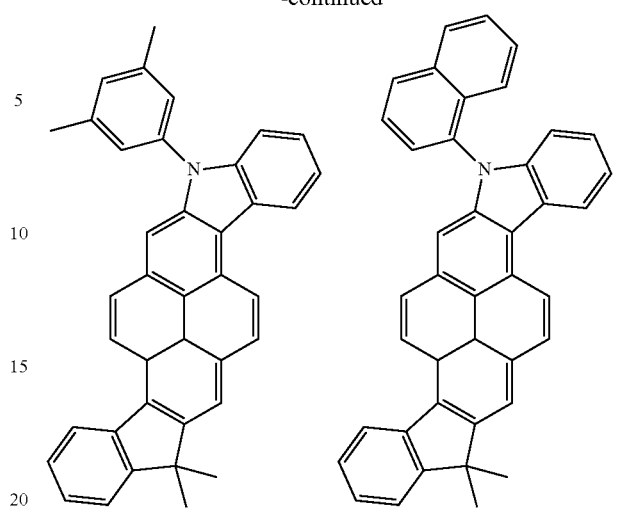
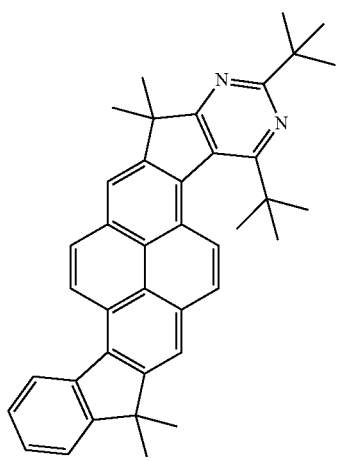
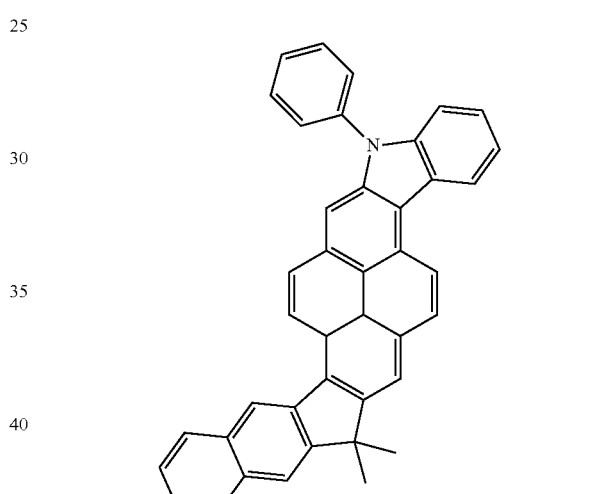
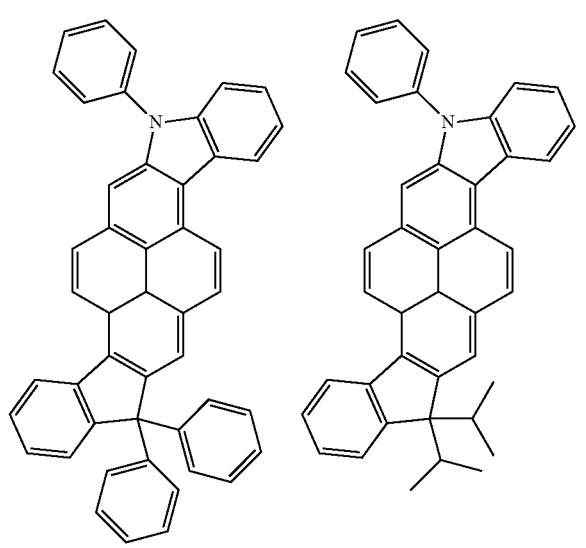
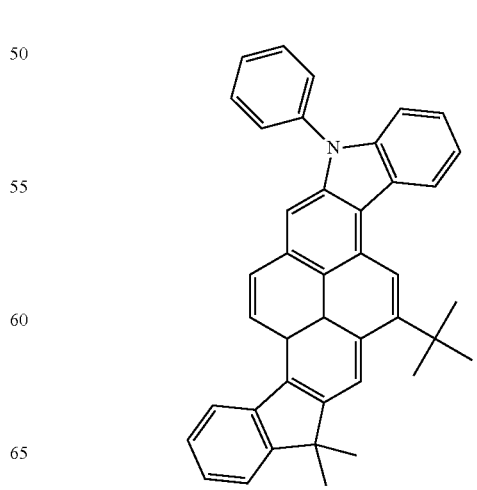

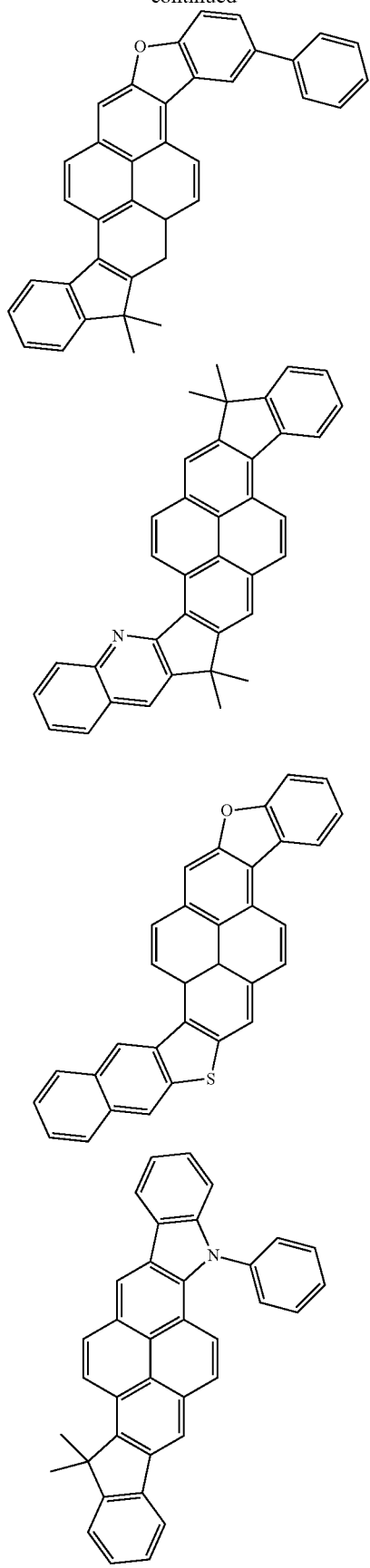
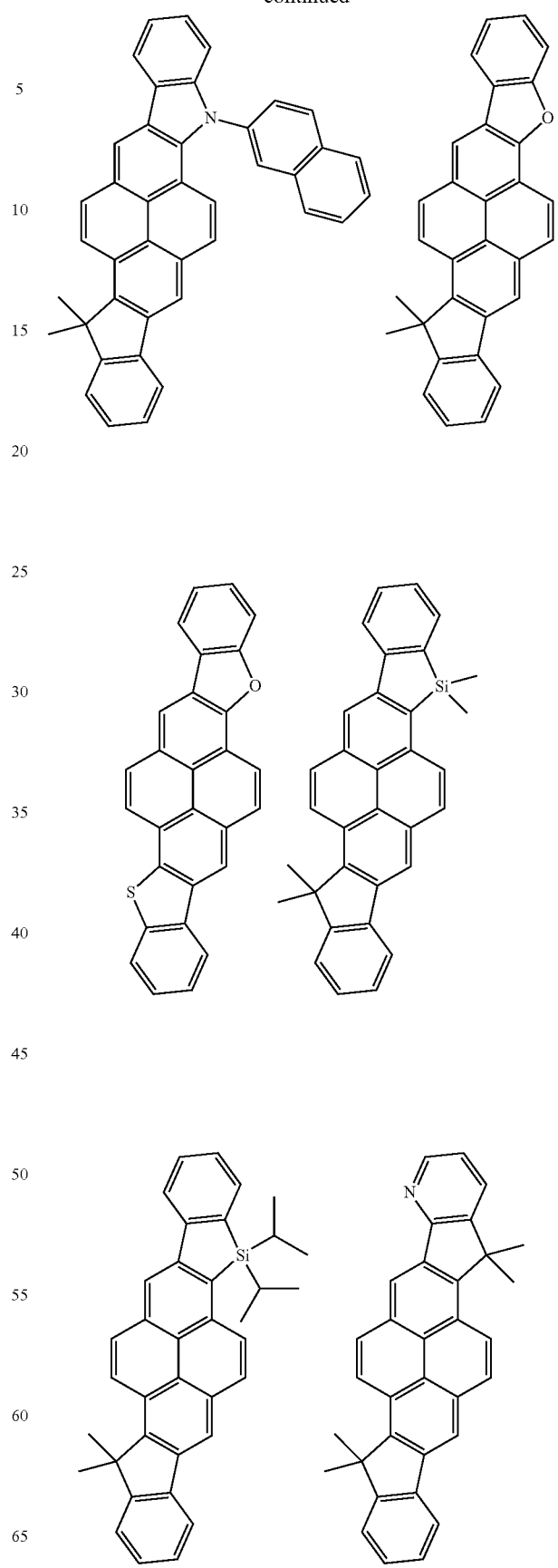

33
-continued
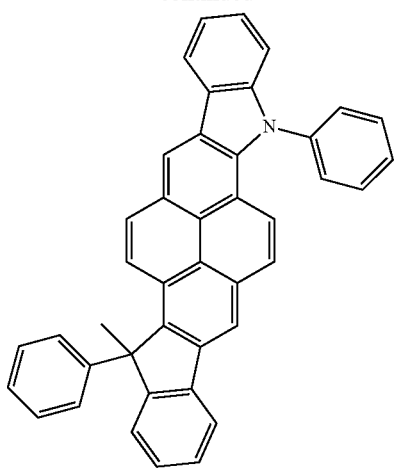
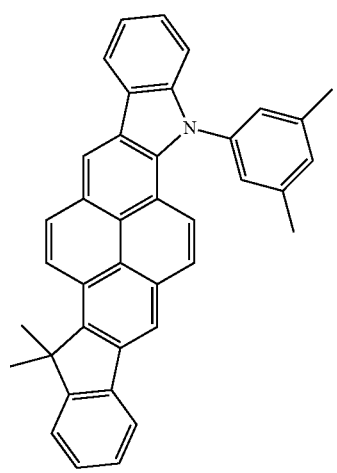
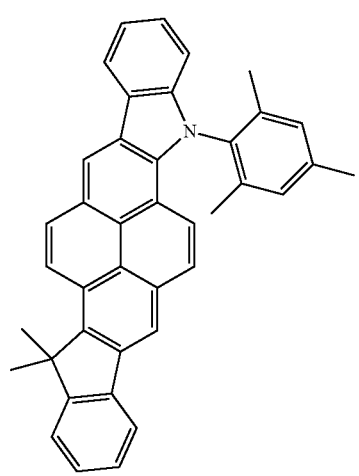
34
-continued
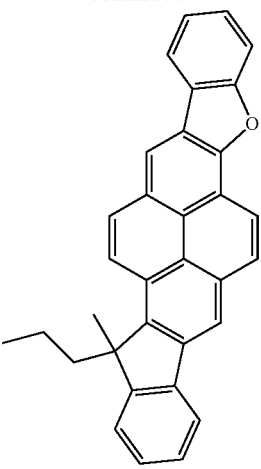
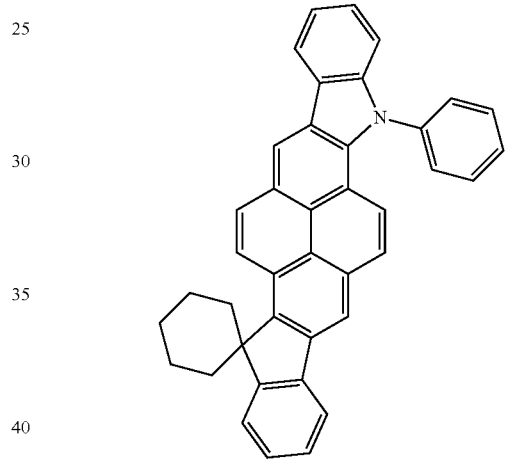
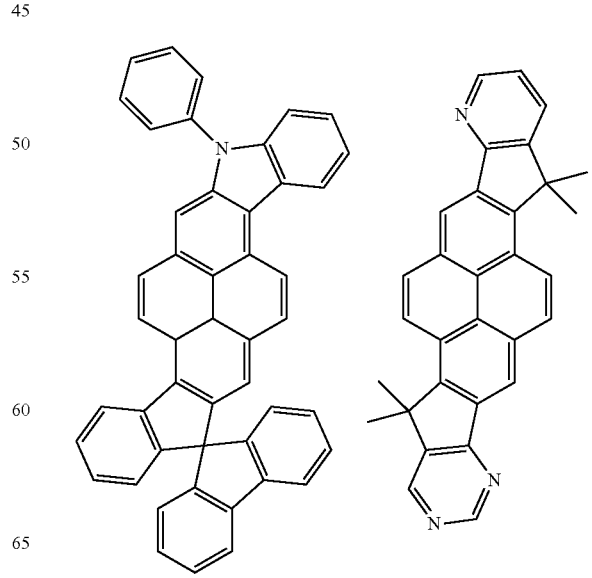

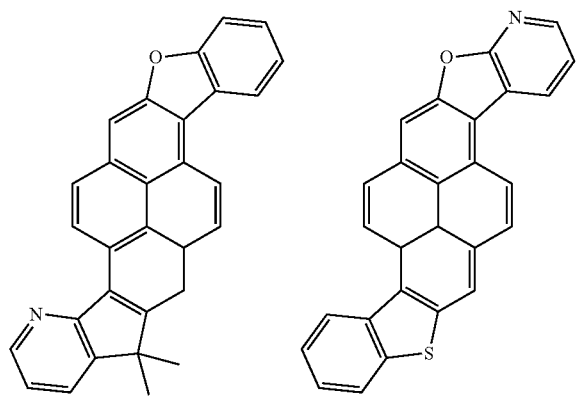
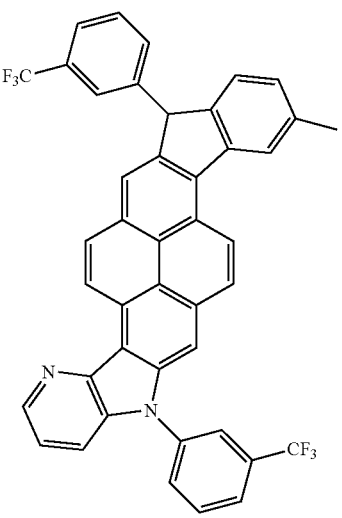
[Chem. 20]
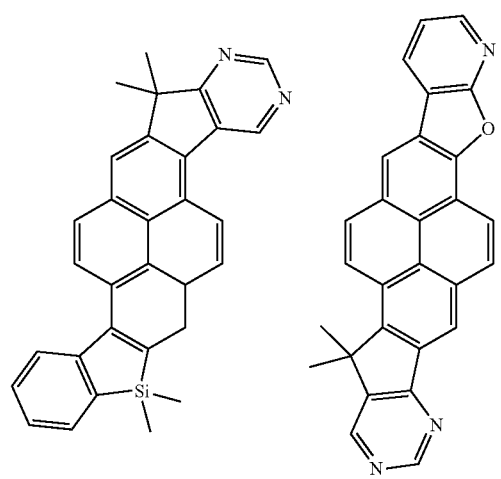
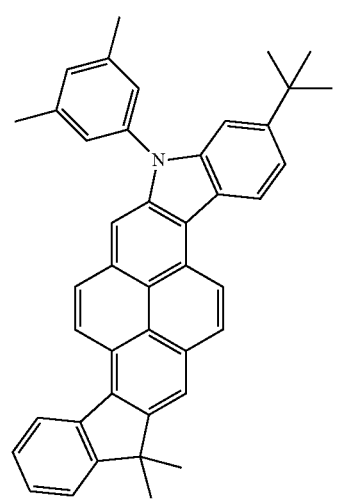
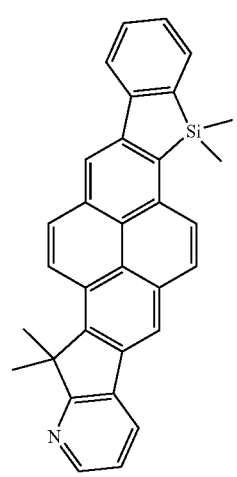
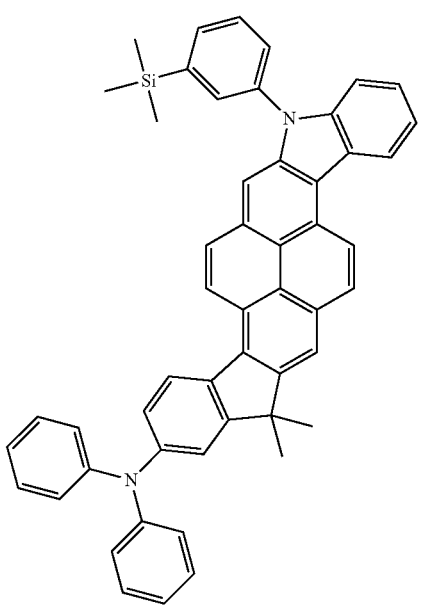

37
-continued
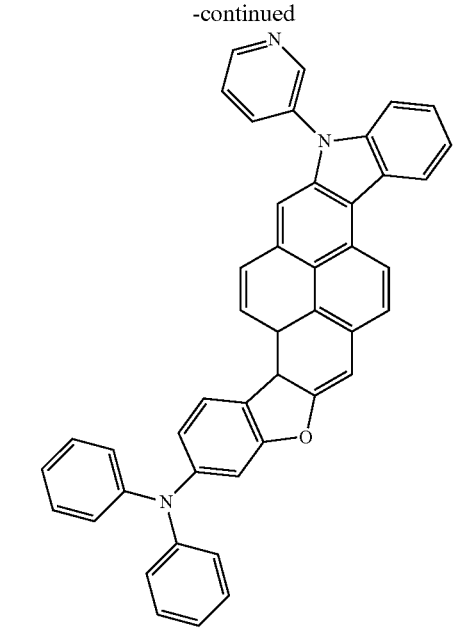
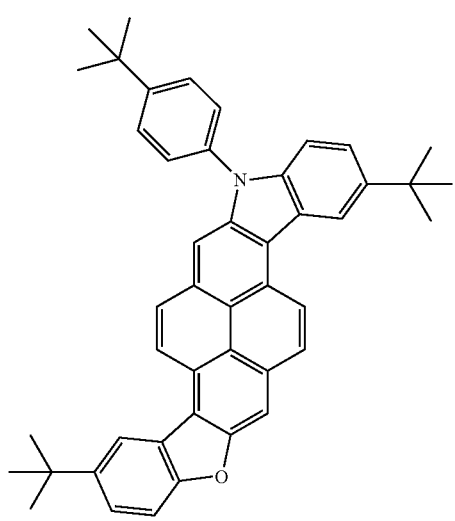
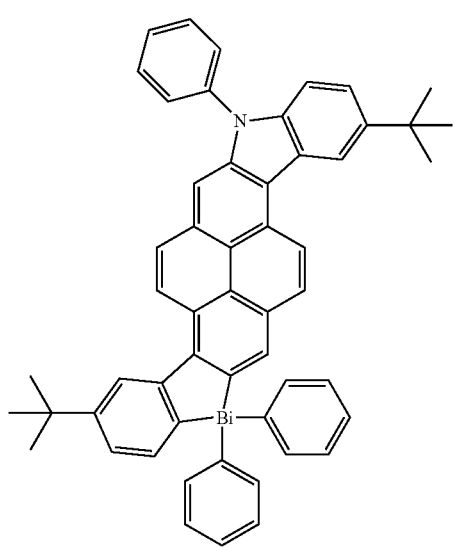
38
-continued
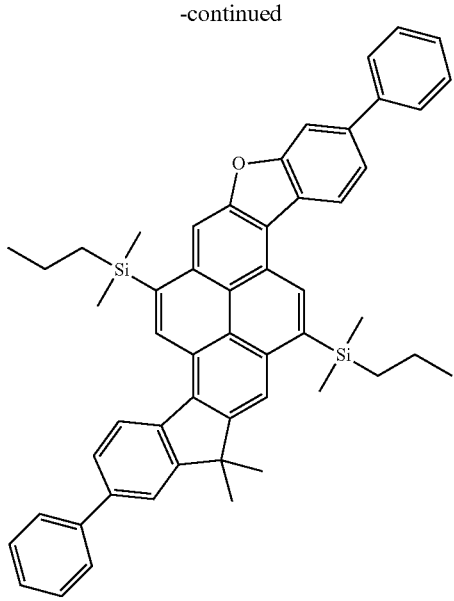
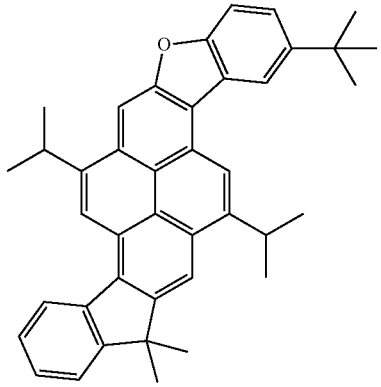
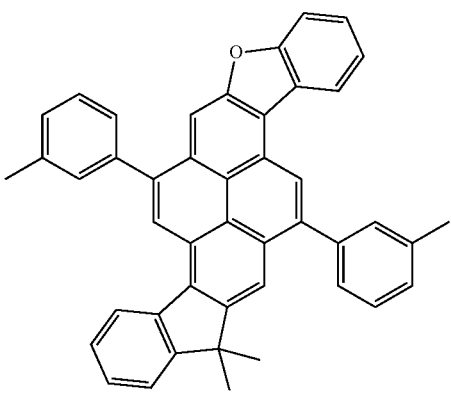

-continued
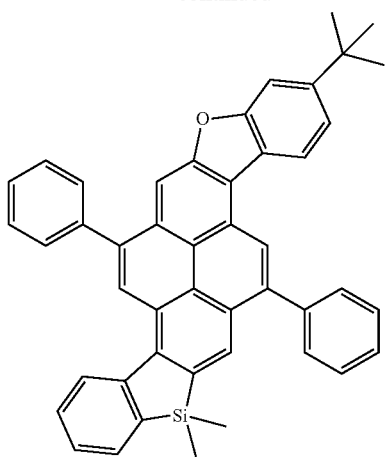
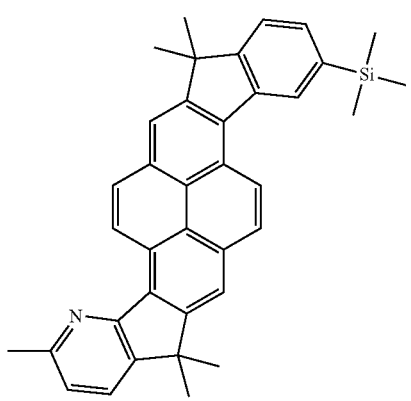
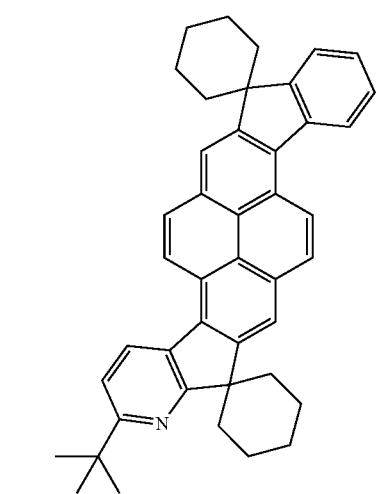
-continued
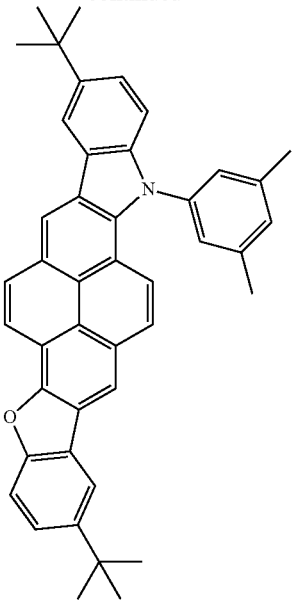
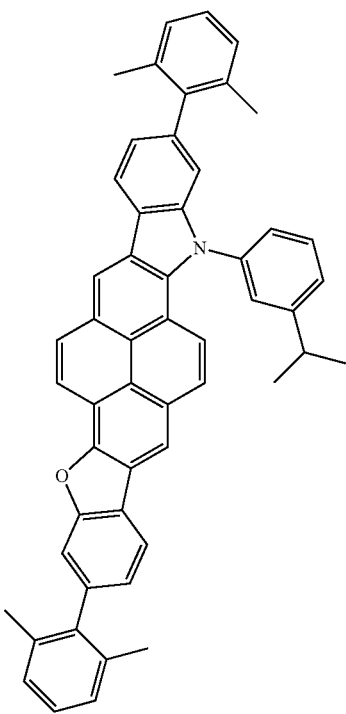

41
-continued
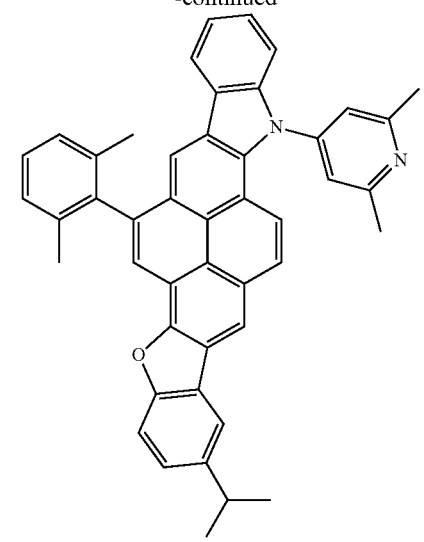
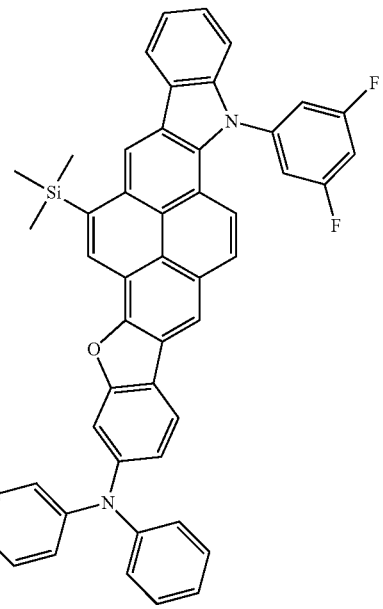
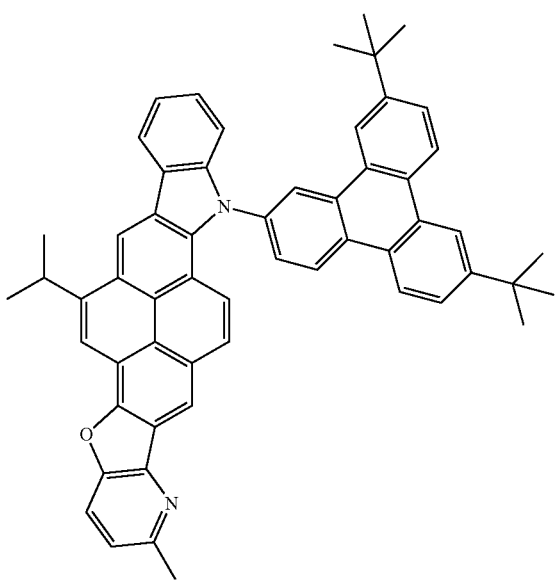
42
-continued
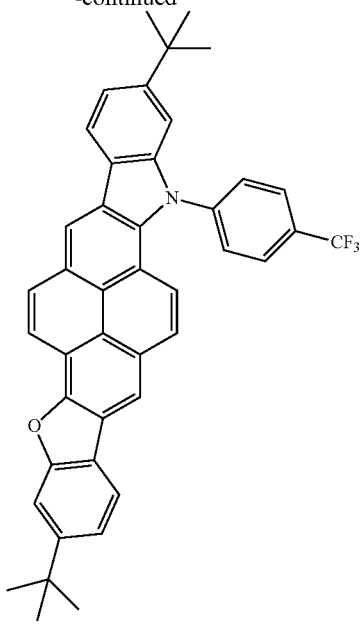
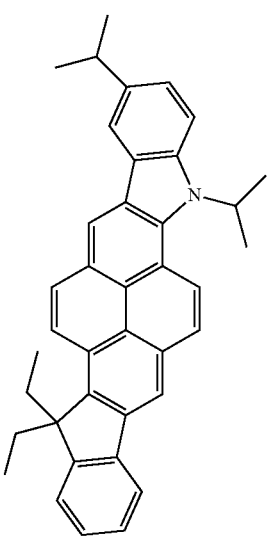

43
-continued
44
-continued
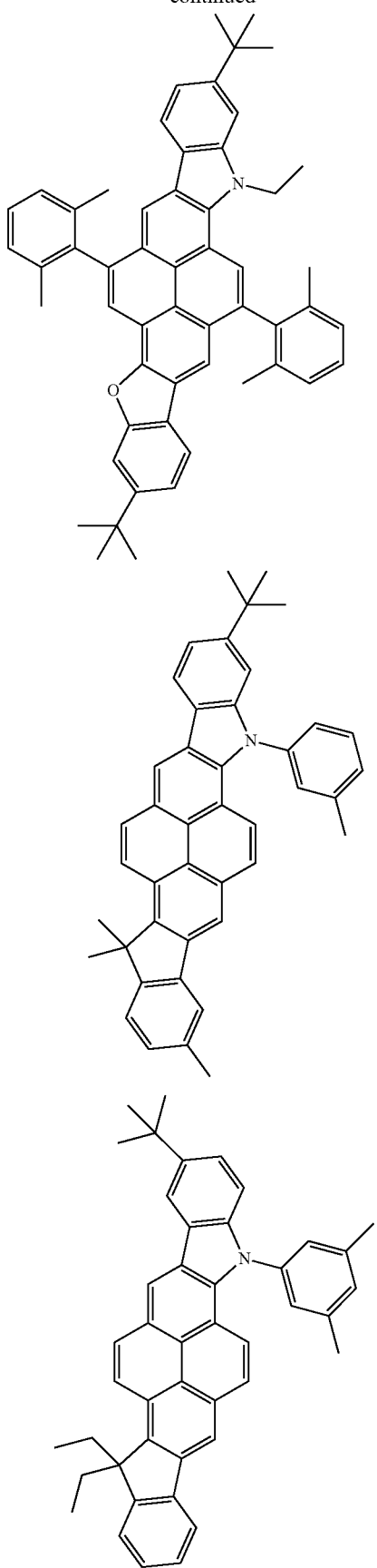

-continued
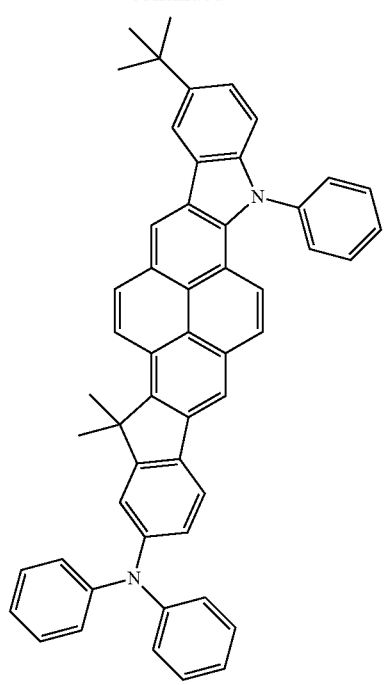
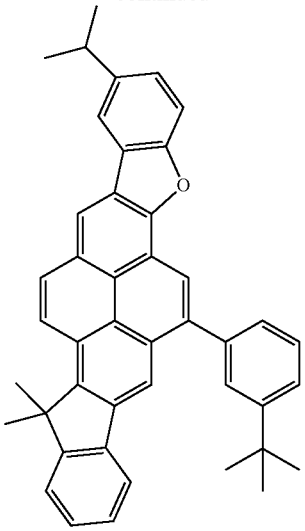
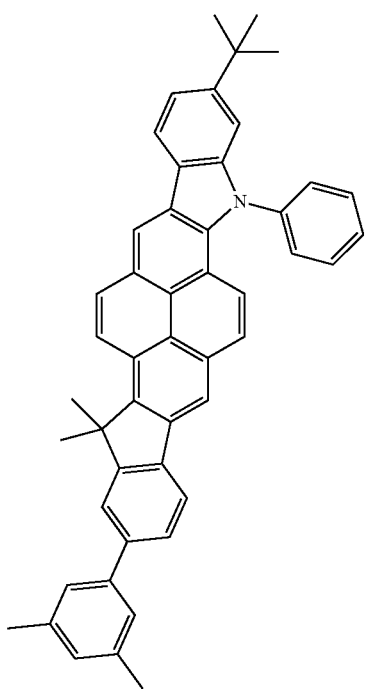
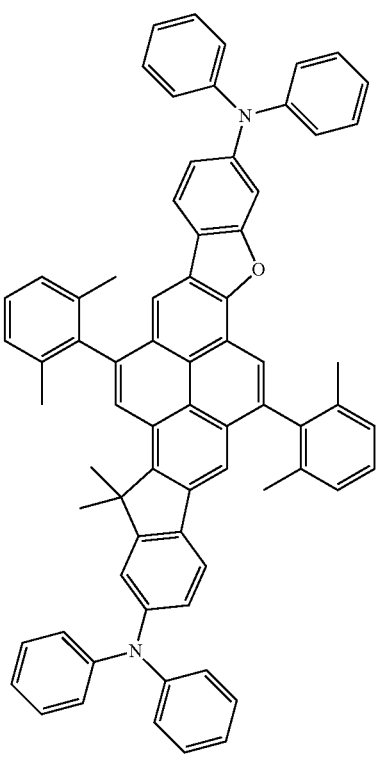

47
-continued
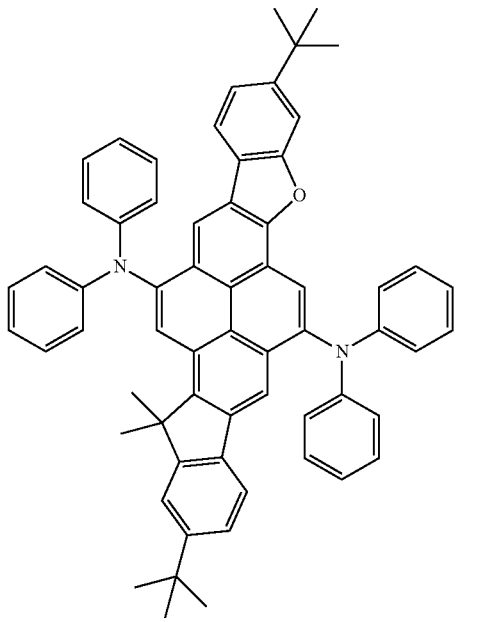
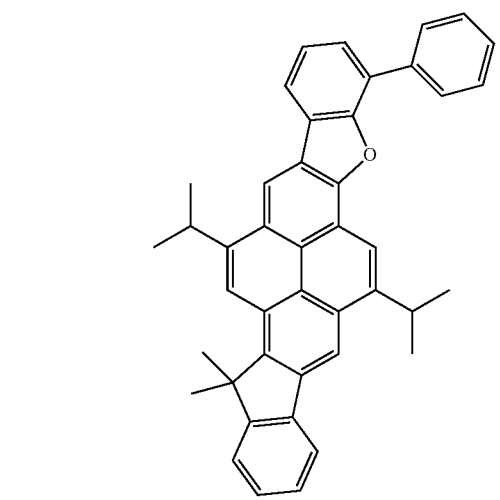
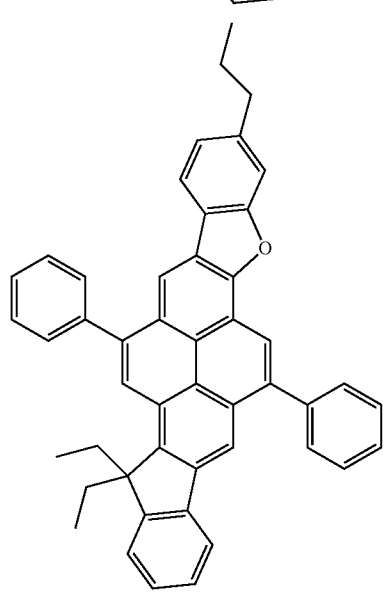
48
-continued
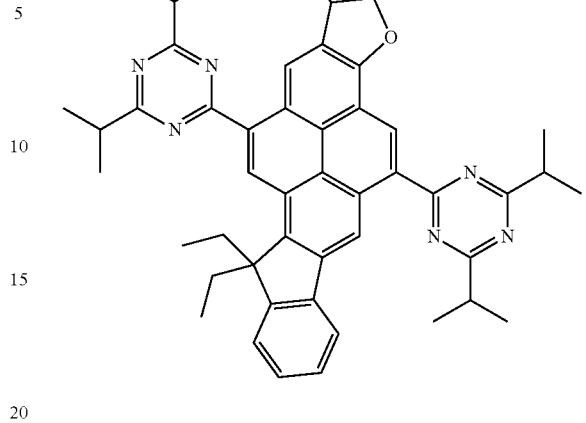
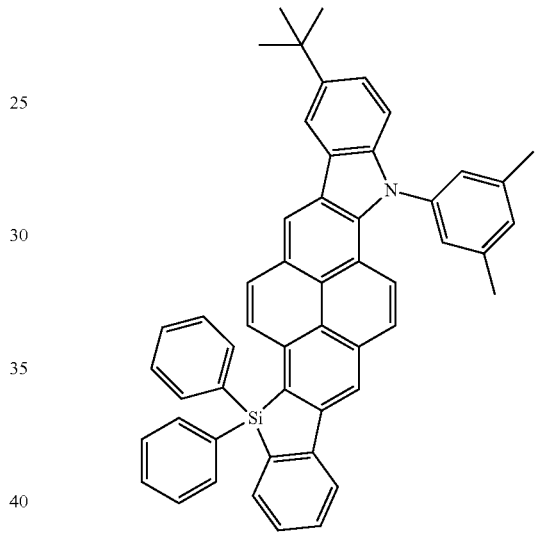
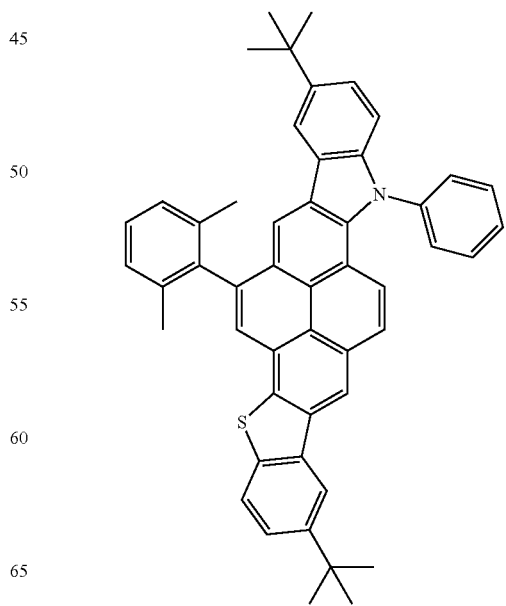

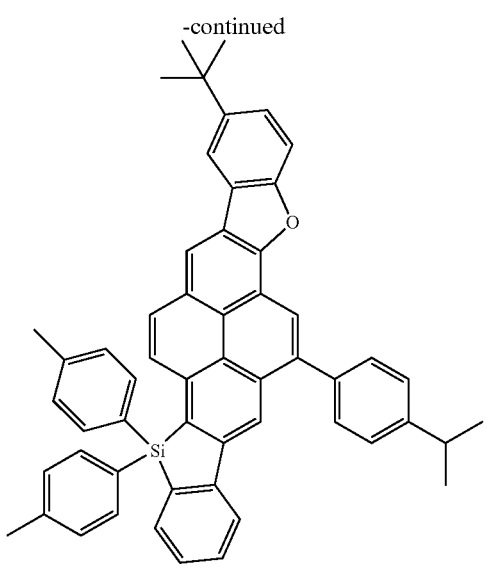
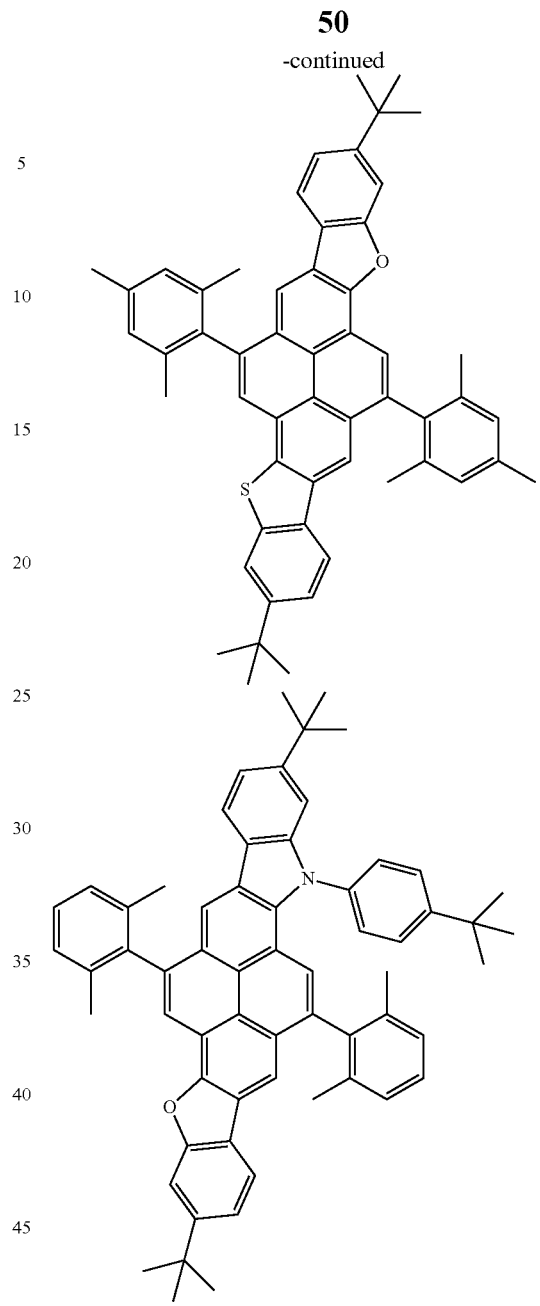
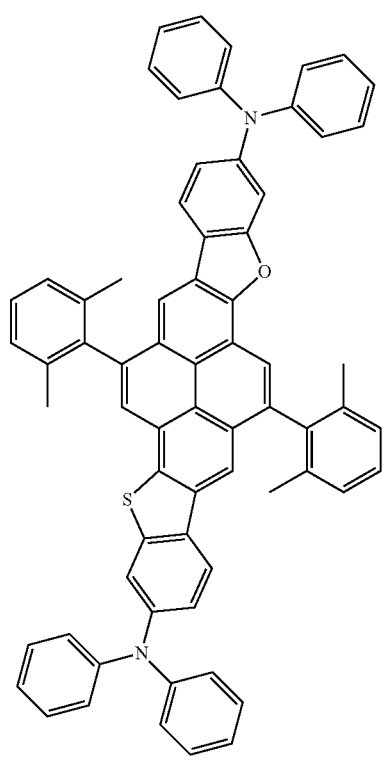
The compound represented by the general formula (I) can be synthesized by a combination of known reactions. In the case of synthesizing a compound in which $Q^1$ and $Q^2$ in the general formula (I) are different, for example, the compound can be synthesized by the following scheme for sequentially introducing a $Q^1$ site and a $Q^2$ site.
[Chem. 21]
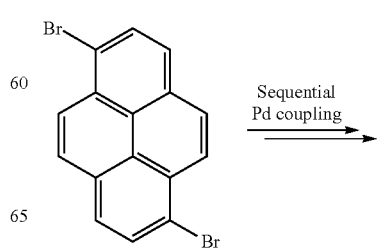

-continued

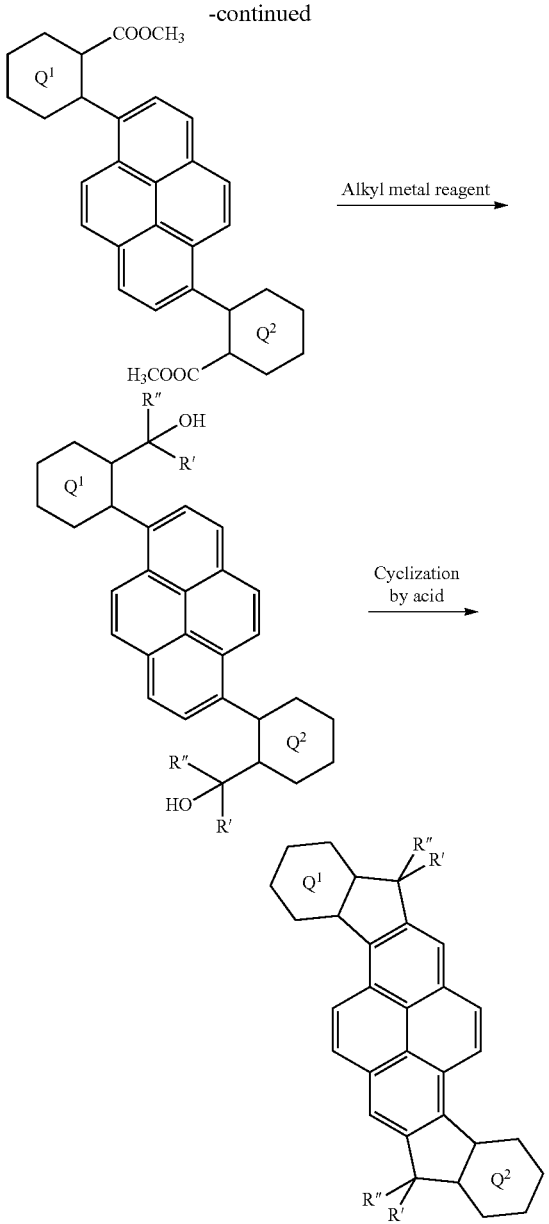

The synthesized compound is preferably purified by column chromatography, recrystallization, or the like, and then purified by sublimation purification. By the sublimation purification, organic impurities can be separated and inorganic salts, residual solvents, or the like can be removed effectively.

When the compounds represented by the general formula (I) are used as light emitting material, the maximum light emitting wavelength thereof is preferably less than 460 nm, more preferably 400 nm or more and less than 460 nm, particularly preferably 420 nm or more and less than 460 nm, still more preferably 430 nm or more and less than 460 nm, and most preferably 440 nm or more and less than 460 nm.

[Organic Electroluminescent Element]

The organic electroluminescent element of the present invention includes a substrate, a pair of electrodes including an anode and a cathode, disposed on the substrate, and at least one organic layer including a light emitting layer, disposed between the electrodes, in which a compound represented by the general formula (I) is contained in any layers of the organic layers.

The configuration of the organic electroluminescent element of the present invention is not particularly limited.

FIG. 1 shows one example of the configuration of the organic electroluminescent element of the present invention. The organic electroluminescent element 10 in FIG. 1 has an organic layer between a pair of electrodes (an anode 3 and a cathode 9) on a substrate 2.

The element configuration of the organic electroluminescent element, the substrate, the cathode, and the anode are described in detail in, for example, JP-A-2008-270736, and the detailed descriptions described in this publication can be applied to the present invention.

Hereinafter, preferred aspects of the organic electroluminescent element of the present invention will be described in detail in the order of the substrate, the electrodes, the organic layer, a protective layer, a sealing enclosure, a driving method, a light emitting wavelength, and applications.

<Substrate>

The organic electroluminescent element of the present invention has a substrate.

The substrate used in the present invention is preferably a substrate that does not scatter or decay light emitted from the organic layer. In the case of an organic material, those having excellent heat resistance, dimensional stability, solvent resistance, electrical insulating properties, and processability are preferred.

<Electrodes>

The organic electroluminescent element of the present invention has a pair of electrodes including an anode and a cathode, disposed on the substrate.

In view of the properties of the light emitting element, at least one electrode of a pair of electrodes, the anode and the cathode, is preferably transparent or semi-transparent.

(Anode)

The anode may be usually one having a function as an electrode of supplying holes into an organic layer, and is not particularly limited in terms of its shape, structure, size, or the like. Further, depending on the use and purpose of the light emitting element, the anode can be suitably selected from the known electrode materials. As described above, the anode is usually provided as a transparent anode.

(Cathode)

The cathode may be usually one having a function as an electrode of injecting electrons to an organic layer, and is not particularly limited in terms of its shape, structure, size, or the like. Further, depending on the use and purpose of the light emitting element, the cathode can be suitably selected from the known electrode materials.

<Organic Layer>

The organic electroluminescent element of the present invention has at least one organic layer including a light emitting layer, disposed between the electrodes, in which the organic layer includes the host material and at least one emitting material represented by the general formula (I).

The organic layer is not particularly limited and can be suitably selected depending on the use and purpose of the organic electroluminescent element. However, the organic layer is preferably formed on the transparent electrode or the semi-transparent electrode. In that case, the organic layer is formed on the whole surface or one surface of the transparent electrode or the semi-transparent electrode.

The shape, the size, the thickness, and the like of the organic layer are not particularly limited and can be suitably selected depending on the purpose.

Hereinafter, the configuration of the organic layer, the method for forming an organic layer, preferred aspects of the respective layers constituting the organic layer, and the materials used in the respective layers in the organic electroluminescent element of the present invention will be described in detail in order.

(Configuration of Organic Layer)

In the organic electroluminescent element of the present invention, the organic layer includes a light emitting layer. The organic layer preferably includes a charge transporting layer. The charge transporting layer refers to a layer in which charges move when voltage is applied to the organic electroluminescent element. Specifically, examples thereof include a hole injecting layer, a hole transporting layer, an electron blocking layer, a light emitting layer, a hole blocking layer, an electron transporting layer, and an electron injecting layer. When the charge transporting layer is a hole injecting layer, a hole transporting layer, an electron blocking layer, or a light emitting layer, an organic electroluminescent element can be prepared with low cost and high efficiency.

The compound represented by the general formula (I) is contained in at least one layer out of one or a plurality of organic layers disposed between the electrodes of the organic electroluminescent element. In particular, the compound represented by the general formula (I) is preferably contained in the organic layer. However, so far as the gist of the present invention is deviated, the compound represented by the general formula (I) may be contained in another organic layer of the organic electroluminescent element of the present invention. Examples of the organic layer other than the light emitting layer, which may contain the compound represented by the general formula (I), include a hole injecting layer, a hole transporting layer, an electron transporting layer, an electron injecting layer, an exciton blocking layer, and a charge blocking layer (a hole blocking layer, an electron blocking layer, or the like), preferably any one of an exciton blocking layer, a charge blocking layer, an electron transporting layer, and an electron injecting layer, and more preferably an exciton blocking layer, a charge blocking layer, or an electron transporting layer.

In the case where the compound represented by the general formula (I) is contained in the light emitting layer, the compound represented by the general formula (I) is contained in the light emitting layer, preferably in the amount of 0.1% by mass to 100% by mass, more preferably 1% by mass to 50% by mass, and still more preferably 2% by mass to 20% by mass, with respect to the total mass.

In the case where the compound represented by the general formula (I) is contained in an organic layer other than the light emitting layer, the compound represented by the general formula (I) is contained in the light emitting layer, preferably in the amount of 70% by mass to 100% by mass, more preferably 80% by mass to 100% by mass, and still more preferably 90% by mass to 100% by mass, with respect to the total mass.

(Method for Forming Organic Layer)

The respective organic layers in the organic electroluminescent element of the present invention can be suitably formed by any of dry film forming methods such as a deposition method and a sputtering method, and wet type film forming methods (solution coating methods) such as a transfer method, a printing method, a spin coating method, and a bar coating method.

In the organic electroluminescent element of the present invention, the organic layer disposed between the pair of electrodes is preferably formed by a vacuum deposition process or a wet process. Further, the light emitting layer is more preferably formed by deposition of a composition further including at least the compound represented by the general formula (I).

(Light Emitting Layer)

The light emitting layer is a layer having a function of, upon application of an electric field, receiving holes from the anode, the hole injecting layer, or the hole transporting layer, receiving electrons from the cathode, the electron injecting layer, or the electron transporting layer, providing a recombination site of the holes and the electrons, and causing light emitting. However, the light emitting layer in the present invention is not necessarily limited to the light emitting by such a mechanism.

The light emitting layer in the organic electroluminescent element of the present invention may be constituted of only the light emitting material, or may be constituted as a mixed layer of a host material and the light emitting material. The light emitting material may be made of a single kind or two or more kinds thereof. The host material is preferably a charge transporting material. The host material may be made of a single kind or two or more kinds thereof. Examples thereof include a configuration in which an electron transporting host material and a hole transporting host material are mixed. Further, the light emitting layer may include a material which does not have charge transporting properties and does not emit light.

In addition, the light emitting layer may be made of a single layer or multiple layers of two or more layers. The respective layers may include the same light emitting material or host material, and may also include a different material in every layer. In the case where a plurality of light emitting layers are present, the respective light emitting layers may emit light in a different luminous color from each other.

The thickness of the light emitting layer is not particularly limited, but it is usually from 2 nm to 500 nm, and above all, from the viewpoint of external quantum efficiency, it is more preferably from 3 nm to 200 nm, and still more preferably from 5 nm to 100 nm.

In the organic electroluminescent element of the present invention, the light emitting layer contains the compound represented by the general formula (I), and it is a preferred aspect to use the compound represented by the general formula (I) as a light emitting material of the light emitting layer. Here, the host material as referred to in the present specification is a compound which chiefly plays a role in injecting or transporting charges in the light emitting layer and is also a compound which does not substantially emit light in itself. As used herein, the statement "which does not substantially emit light" means that the amount of light emission from the compound which does not substantially emit light is preferably 5% or less, more preferably 3% or less, and still more preferably 1% or less, with respect to the total amount of light emission in the whole of the element. The compound represented by the general formula (I) may be used as a host material of the light emitting layer.

(Light Emitting Material)

In the organic electroluminescent element of the present invention, the compound represented by the general formula (I) is preferably used as the light emitting material, but in this case, a combination of the compound with light emitting materials different from the compound represented by the general formula (I) can be used. Further, in the organic electroluminescent element of the present invention, in the case where the compound represented by the general formula (I) is used as a host material of the light emitting layer or in the case where the compound represented by the general formula (I) is used in an organic layer other than the light emitting layer, it is used in the light emitting materials different from the compound represented by the general formula (I).

The light emitting material which can be used in the present invention may be a phosphorescent light emitting material. Further, the light emitting layer in the present invention may contain two or more kinds of light emitting materials in order to improve the color purity or widen the light emitting wavelength region.

The fluorescent light emitting material and the phosphorescent material which can be used in the organic electroluminescent element of the present invention are described in detail in, for example, paragraph Nos. [0100] to of JP-A-2008-270736 and paragraph Nos. [0088] to [0090] of JP-A-2007-266458, the detailed descriptions thereon in these publications can be applied to the present invention.

The kind of the fluorescent light emitting material which can be used in the present invention is not particularly limited, but examples thereof include those other than the compound represented by the general formula (I), for example, benzoxazole, benzimidazole, benzothiazole, styrylbenzene, polyphenyl, diphenylbutadiene, tetraphenylbutadiene, naphthalimide, coumarin, pyrane, perinone, oxadiazole, aldazine, pyralizine, cyclopentadiene, bisstyrylanthracene, quinacridone, pyrrolopyridine, thiadiazolopyridine, cyclopentadiene, styrylamine, aromatic fused polycyclic compounds (anthracene, phenanthroline, pyrene, perylene, rubrene, pentacene, and the like), a variety of metal complexes typified by metal complexes of 8-quinolinol, pyrromethene complexes, and rare-earth complexes, polymer compounds such as polythiophene, polyphenylene, and polyphenylenevinylene, organic silanes, and derivatives thereof.

In addition, the compound described in [0082] of JP-A-2010-111620 can also be used as a light emitting material.

The light emitting layer in the organic electroluminescent element of the present invention may be constituted with only a light emitting material or may be constituted as a mixed layer of a host material and a light emitting material. The light emitting material may be made of a single kind or two or more kinds. The host material is preferably a charge transport material. The host material may be made of a single kind or two or more kinds. Examples thereof include a configuration in which an electron-transporting host material and a hole-transporting host material are mixed. Furthermore, the light emitting layer may contain a material which does not have charge transporting properties and which does not emit light.

In addition, the light emitting layer may be made of a single layer or two or more layers. The respective layers may include the same light emitting materials or host materials, and may also include different materials from each other over layers. In the case where a plurality of light emitting layers are present, the respective light emitting layers may emit light in different luminous colors from each other.

(Host Material)

The host material is a compound that usually plays a role in injecting or transporting charges in the light emitting layer and is also a compound which does not substantially emit light in itself. As used herein, it is meant by the terms "which does not substantially emit light" that the amount of light emitting from the compound which does not substantially emit light is preferably 5% or less, more preferably 3% or less, and still more preferably 1% or less of the total amount of light emitting in the whole of the element.

Examples of the host material which can be used in the organic electroluminescent element of the present invention include the following compounds, other than compound represented by the general formula (I):

conductive high-molecular oligomers such as pyrrole, indole, carbazole, azaindole, azacarbazole, triazole, oxazole, oxadiazole, pyrazole, imidazole, thiophene, benzothiophene, dibenzothiophene, furan, benzofuran, dibenzofuran, polyarylalkanes, pyrazoline, pyrazolone, phenylenediamine, arylamines, amino-substituted chalcone, styrylanthracene, fluorenone, hydrazone, stilbene, silazane, aromatic tertiary amine compounds, styrylamine compounds, porphyrin-based compounds, fused ring aromatic hydrocarbon compounds (fluorene, naphthalene, phenanthrene, triphenylene, and the like), polysilane-based compounds, poly(N-vinylcarbazole), aniline-based copolymers, thiophene oligomers, and polythiophene, organic silanes, carbon films, pyridine, pyrimidine, triazine, imidazole, pyrazole, triazole, oxazole, oxadiazole, fluorenone, anthraquinodimethane, anthrone, diphenylquinone, thiopyran dioxide, carbodiimide, fluorenylidenemethane, distyrylpyrazine, fluorine-substituted aromatic compounds, heterocyclic tetracarboxylic anhydrides such as naphthalene perylene, phthalocyanine, and a variety of metal complexes typified by metal complexes of 8-quinolinol derivatives and metal complexes having metal phthalocyanine, benzoxazole, or benzothiazole as a ligand thereof, and derivatives thereof (which may have a substituent or a fused ring). In addition, the compounds described in [0081] or [0083] of JP-A-2010-111620 can also be used.

Above all, carbazole, dibenzothiophene, dibenzofuran, arylamine, aromatic hydrocarbon compounds with fused rings, and metal complexes are preferred, and aromatic hydrocarbon compounds with fused rings are particularly preferred since they are stable. As the aromatic hydrocarbon compounds with fused rings, naphthalene-based compounds, anthracene-based compounds, phenanthrene-based compounds, triphenylene-based compounds, and pyrene-based compounds are preferred; anthracene-based compounds and pyrene-based compounds are more preferred; and anthracene-based compounds are particularly preferred. As the anthracene-based compounds, those described in [0033] to [0064] of WO 2010/134350 are particularly preferred, and examples thereof include Compounds H-1 and H-2 as described later.

In the organic electroluminescent element of the present invention, the host material included in the light emitting layer preferably has a hydrocarbon fused ring structure having 10 to 50 carbon atoms.

The hydrocarbon fused ring structure having 10 to 50 carbon atoms is preferably naphthalene, phenanthrene, benzo[c]phenanthrene, anthracene, pyrene, triphenylene, or chrysene, more preferably naphthalene, phenanthrene, benzo[c]phenanthrene, or anthracene, and most preferably anthracene. That is, the hydrocarbon fused ring structure having 10 to 50 carbon atoms in the host material is further preferably an anthracene skeleton. Further, it is particularly preferable that the hydrocarbon fused ring structure having 10 to 50 carbon atoms is a compound composed of only carbon, and hydrogen or deuterium.

The host material that can be used in the light emitting layer in the organic electroluminescent element of the present invention may be a host material having hole transporting properties or a host material having electron transporting properties.

In the light emitting layer, the singlet lowest excited energy ($S_1$ energy) in the film state of the host material is preferably higher than the $S_1$ energy of the light emitting material from the viewpoints of color purity, luminous efficiency, and driving durability. The $S_1$ of the host material is preferably higher than the $S_1$ of the light emitting material by 0.1 eV or more, more preferably by 0.2 eV or more, and still more preferably by 0.3 eV or more.

When $S_1$ in the film state of the host material is lower than $S_1$ of the light emitting material, the light emitting is lost, and thus, the host material is required to have higher $S_1$ than the $S_1$ of the light emitting material. Further, even in the case where $S_1$ of the host material is higher than the $S_1$ of the light emitting material, a small difference in the $S_1$ of the both leads to partial reverse energy movement from the light emitting material to the host material, which causes reduction in efficiency, color purity, or durability. Therefore, there is a demand for a host material having a sufficiently high $S_1$, and high chemical stability and carrier injecting/transporting properties.

Furthermore, the content of the host compound in the light emitting layer in the organic electroluminescent element of the present invention is not particularly limited, but from the viewpoint of luminous efficiency and driving voltage, it is preferably from 15% by mass to 95% by mass, with respect to the total mass of the compounds forming the light emitting layer. When the light emitting layer includes a plurality of kinds of host compounds containing the compound represented by the general formula (I), the content of the compound represented by the general formula (I) is preferably from 50% by mass to 99% by mass, with respect to the total host compounds.

(Other Layers)

The organic electroluminescent element of the present invention may include layers other than the light emitting layer.

Examples of the organic layer other than the light emitting layer which may be included in the organic layer include a hole injecting layer, a hole transporting layer, a blocking layer (a hole blocking layer, an exciton blocking layer, and the like), and an electron transporting layer. Specifically, examples of the layer configuration include those described below, but it should not be construed that the present invention is limited to these configurations.

Anode/hole transporting layer/light emitting layer/electron transporting layer/cathode,
Anode/hole transporting layer/light emitting layer/blocking layer/electron transporting layer/cathode,
Anode/hole transporting layer/light emitting layer/blocking layer/electron transporting layer/electron injecting layer/cathode,
Anode/hole injecting layer/hole transporting layer/light emitting layer/blocking layer/electron transporting layer/cathode,
Anode/hole injecting layer/hole transporting layer/light emitting layer/electron transporting layer/electron injecting layer/cathode,
Anode/hole injecting layer/hole transporting layer/light emitting layer/blocking layer/electron transporting layer/electron injecting layer/cathode,
Anode/hole injecting layer/hole transporting layer/blocking layer/light emitting layer/blocking layer/electron transporting layer/electron injecting layer/cathode.

The organic electroluminescent element of the present invention preferably includes at least one organic layer which is preferably disposed between the (A) anode and the light emitting layer. Examples of the organic layer which is preferably disposed between the (A) anode and the light emitting layer include an hole injecting layer, a hole transporting layer, and an electron blocking layer from the anode side.

The organic electroluminescent element of the present invention preferably includes at least one organic layer which is preferably disposed between the (B) cathode and the light emitting layer. Examples of the organic layer which is preferably disposed between the (B) cathode and the light emitting layer include an electron injecting layer, an electron transporting layer, and a hole blocking layer from the cathode side.

Specifically, an example of the preferred aspects of the organic electroluminescent element of the present invention is the aspect shown in FIG. 1, in which a hole injecting layer 4, a hole transporting layer 5, a light emitting layer 6, a hole blocking layer 7, and an electron transporting layer 8 are laminated in this order as the organic layer from the anode 3 side.

Hereinafter, the layers other than the light emitting layer which the organic electroluminescent element of the present invention may have will be described.

(A) Organic Layer Preferably Disposed between Anode and Light Emitting Layer:

First, the (A) organic layer preferably disposed between the anode and the light emitting layer will be described.

(A-1) Hole Injecting Layer and Hole Transporting Layer

The hole injecting layer and the hole transporting layer are layers having a function of receiving holes from the anode or the anode side and transporting them to the cathode side.

The light emitting element of the present invention preferably includes at least one organic layer between the light emitting layer and the anode, and the organic layer preferably includes at least one compound of the compounds represented by the following general formulae (Sa-1), (Sb-1), and (Sc-1).

General formula (Sa-1)

[Chem. 22]

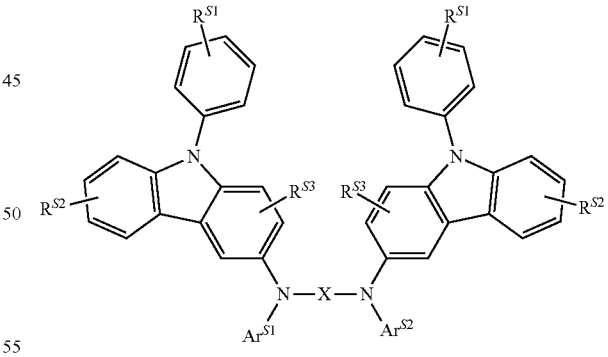

(in which X represents a substituted or unsubstituted alkylene group having 1 to 30 carbon atoms, a substituted or unsubstituted alkenylene group having 2 to 30 carbon atoms, a substituted or unsubstituted arylene group having 6 to 30 carbon atoms, a substituted or unsubstituted heteroarylene group having 2 to 30 carbon atoms, or a substituted or unsubstituted heterocycle having 2 to 30 carbon atoms. $R^{S1}$, $R^{S2}$, and $R^{S3}$ each independently represent a hydrogen atom, a substituted or unsubstituted alkyl group having 1 to 30 carbon atoms, a substituted or unsubstituted alkoxy group having 1 to 30 carbon atoms, a substituted or unsubstituted aryl group having 6 to 30 carbon atoms, a substituted or unsubstituted aryloxy group having 6 to 30 carbon atoms, a substituted or unsubstituted heterocycle having 2 to 30 carbon atoms, a substituted or unsubstituted fused polycyclic group having 5 to 30 carbon atoms, a hydroxy group, a cyano group, or a substituted or unsubstituted amino group. Adjacent $R^{S1}$, $R^{S2}$, and $R^{S3}$ may be bonded to each other to form a saturated carbocycle or an unsaturated carbocycle. $Ar^{S1}$ and $Ar^{S2}$ each independently represent a substituted or unsubstituted aryl group having 6 to 30 carbon atoms, or a substituted or unsubstituted heteroaryl group having 2 to 30 carbon atoms.)

[Chem. 23]

General formula (Sb-1)

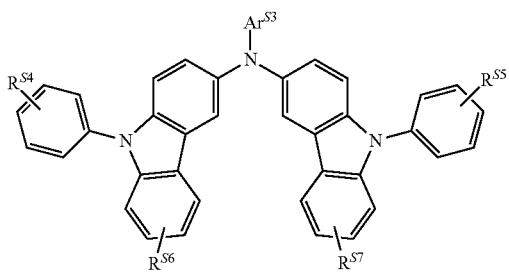

(in which $R^{S4}$, $R^{S5}$, $R^{S6}$, and $R^{S7}$ each independently represent a hydrogen atom, a substituted or unsubstituted alkyl group having 1 to 30 carbon atoms, a substituted or unsubstituted alkoxy group having 1 to 30 carbon atoms, a substituted or unsubstituted aryl group having 6 to 30 carbon atoms, a substituted or unsubstituted aryloxy group having 6 to 30 carbon atoms, a substituted or unsubstituted heterocycle having 2 to 30 carbon atoms, a substituted or unsubstituted fused polycyclic group having 5 to 30 carbon atoms, a hydroxy group, a cyano group, or a substituted or unsubstituted amino group. Adjacent $R^{S4}$, $R^{S5}$, $R^{S6}$, and $R^{S7}$ may be bonded to each other to form a saturated carbocycle or an unsaturated carbocycle. $Ar^{S3}$ represents a substituted or unsubstituted aryl group having 6 to 30 carbon atoms, or a substituted or unsubstituted heteroaryl group having 2 to 30 carbon atoms.)

[Chem. 24]

General formula (Sc-1)

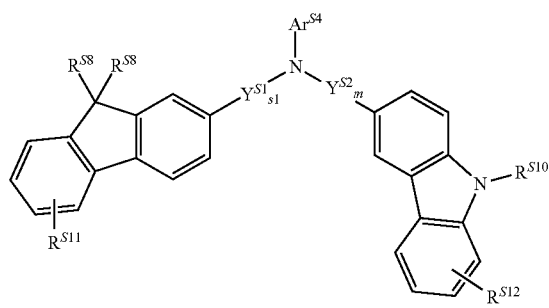

(in which $R^{S8}$ and $R^{S9}$ each independently represent a hydrogen atom, a substituted or unsubstituted alkyl group having 1 to 30 carbon atoms, a substituted or unsubstituted aryl group having 6 to 30 carbon atoms, a substituted or unsubstituted heterocyclic group having 2 to 30 carbon atoms, or a substituted or unsubstituted fused polycyclic group having to 30 carbon atoms. $R^{S10}$ represents a substituted or unsubstituted alkyl group having 1 to 30 carbon atoms, a substituted or unsubstituted aryl group having 6 to 30 carbon atoms, a substituted or unsubstituted heterocyclic group having 2 to 30 carbon atoms, or a substituted or unsubstituted fused polycyclic group having 5 to 30 carbon atoms. $R^{S11}$ and $R^{S12}$ each independently represent a hydrogen atom, a substituted or unsubstituted alkyl group having 1 to 30 carbon atoms, a substituted or unsubstituted alkoxy group having 1 to 30 carbon atoms, a substituted or unsubstituted aryl group having 6 to 30 carbon atoms, a substituted or unsubstituted aryloxy group having 6 to 30 carbon atoms, a substituted or unsubstituted heterocycle having 2 to 30 carbon atoms, a substituted or unsubstituted fused polycyclic group having 5 to 30 carbon atoms, a hydroxy group, a cyano group, or a substituted or unsubstituted amino group. Adjacent $R^{S11}$ and $R^{S12}$ may be bonded to each other to form a saturated carbocycle or an unsaturated carbocycle. $Ar^{S4}$ represents a substituted or unsubstituted aryl group having 6 to 30 carbon atoms, or a substituted or unsubstituted heteroaryl group having 2 to 30 carbon atoms. $Y^{S1}$ and $Y^{S2}$ each independently represent a substituted or unsubstituted alkylene group having 1 to 30 carbon atoms, or a substituted or unsubstituted arylene group having 6 to 30 carbon atoms. n and m each independently represent an integer of 0 to 5.)

The general formula (Sa-1) will be described.

In the general formula (Sa-1), X represents a substituted or unsubstituted alkylene group having 1 to 30 carbon atoms, a substituted or unsubstituted alkenylene group having 2 to 30 carbon atoms, a substituted or unsubstituted arylene group having 6 to 30 carbon atoms, a substituted or unsubstituted heteroarylene group having 2 to 30 carbon atoms, or a substituted or unsubstituted heterocycle having 2 to 30 carbon atoms. X is preferably a substituted or unsubstituted arylene group having 6 to 30 carbon atoms, more preferably having a substituted or unsubstituted phenylene, a substituted or unsubstituted biphenylene, and a substituted or unsubstituted naphthylene, and still more preferably a substituted or unsubstituted biphenylene.

$R^{S1}$, $R^{S2}$, and $R^{S3}$ each independently represent a hydrogen atom, a substituted or unsubstituted alkyl group having 1 to 30 carbon atoms, a substituted or unsubstituted alkoxy group having 1 to 30 carbon atoms, a substituted or unsubstituted aryl group having 6 to 30 carbon atoms, a substituted or unsubstituted aryloxy group having 6 to 30 carbon atoms, a substituted or unsubstituted heterocycle having 2 to 30 carbon atoms, a substituted or unsubstituted fused polycyclic group having 5 to 30 carbon atoms, a hydroxy group, a cyano group, or a substituted or unsubstituted amino group. Adjacent $R^{S1}$, $R^{S2}$, and $R^{S3}$ may be bonded to each other to form a saturated carbocycle or an unsaturated carbocycle. Examples of the saturated carbocycle or the unsaturated carbocycle include naphthalene, azulene, anthracene, fluorene, and phenalene. $R^{S1}$, $R^{S2}$, and $R^{S3}$ are preferably a hydrogen atom, a substituted or unsubstituted alkyl group having 1 to 30 carbon atoms, a substituted or unsubstituted aryl group having 6 to 30 carbon atoms, a substituted or unsubstituted fused polycyclic group having 5 to 30 carbon atoms, or a cyano group, and more preferably a hydrogen atom.

$Ar^{S1}$ and $Ar^{S2}$ each independently represent a substituted or unsubstituted aryl group having 6 to 30 carbon atoms, or a substituted or unsubstituted heteroaryl group having 2 to 30 carbon atoms. $Ar^{S1}$ and $Ar^{S2}$ are preferably a substituted or unsubstituted phenyl group.

Next, the general formula (Sb-1) will be described.

In the general formula (Sb-1), $R^{S4}$, $R^{S5}$, $R^{S6}$ and $R^{S7}$ each independently represent a hydrogen atom, a substituted or unsubstituted alkyl group having 1 to 30 carbon atoms, a substituted or unsubstituted alkoxy group having 1 to 30 carbon atoms, a substituted or unsubstituted aryl group having 6 to 30 carbon atoms, a substituted or unsubstituted aryloxy group having 6 to 30 carbon atoms, a substituted or unsubstituted heterocycle having 2 to 30 carbon atoms, or a substituted or unsubstituted fused polycyclic group having 5 to 30 carbon atoms, a hydroxy group, a cyano group, or a substituted or unsubstituted amino group. Adjacent $R^{S4}$, $R^{S5}$, $R^{S6}$ and $R^{S7}$ may be bonded to each other to form a saturated carbocycle or an unsaturated carbocycle. Examples of the saturated carbocycle or the unsaturated carbocycle include naphthalene, azulene, anthracene, fluorene, and phenalene. $R^{S4}$, $R^{S5}$, $R^{S6}$ and $R^{S7}$ are preferably a hydrogen atom, a substituted or unsubstituted alkyl group having 1 to 30 carbon atoms, a substituted or unsubstituted aryl group having 6 to 30 carbon atoms, a substituted or unsubstituted fused polycyclic group having 5 to 30 carbon atoms, or a cyano group, and more preferably a hydrogen atom.

$Ar^{S3}$ represents a substituted or unsubstituted aryl group having 6 to 30 carbon atoms, or a substituted or unsubstituted heteroaryl group having 2 to 30 carbon atoms. $Ar^{S3}$ is preferably a substituted or unsubstituted phenyl group.

Next, the general formula (Sa-1) will be described. In the general formula (Sa-1), $R^{S8}$ and $R^{S9}$ each independently represent a hydrogen atom, a substituted or unsubstituted alkyl group having 1 to 30 carbon atoms, a substituted or unsubstituted aryl group having 6 to 30 carbon atoms, a substituted or unsubstituted heterocyclic group having 2 to 30 carbon atoms, or a substituted or unsubstituted fused polycyclic group having 5 to 30 carbon atoms. $R^{S8}$ and $R^{S9}$ are preferably a substituted or unsubstituted alkyl group having 1 to 30 carbon atoms, or a substituted or unsubstituted aryl group having 6 to 30 carbon atoms, and more preferably a methyl group or a phenyl group. $R^{S10}$ is a substituted or unsubstituted alkyl group having 1 to 30 carbon atoms, a substituted or unsubstituted aryl group having 6 to 30 carbon atoms, a substituted or unsubstituted heterocyclic group having 2 to 30 carbon atoms, or a substituted or unsubstituted fused polycyclic group having 5 to 30 carbon atoms. $R^{S10}$ is preferably a substituted or unsubstituted aryl group having 6 to 30 carbon atoms, and more preferably a phenyl group. $R^{S11}$ and $R^{S12}$ each independently represent a hydrogen atom, a substituted or unsubstituted alkyl group having 1 to 30 carbon atoms, a substituted or unsubstituted alkoxy group having 1 to 30 carbon atoms, a substituted or unsubstituted aryl group having 6 to 30 carbon atoms, a substituted or unsubstituted aryloxy group having 6 to 30 carbon atoms, a substituted or unsubstituted heterocycle having 2 to 30 carbon atoms, a substituted or unsubstituted fused polycyclic group having 5 to 30 carbon atoms, a hydroxy group, a cyano group, or a substituted or unsubstituted amino group. Adjacent $R^{S11}$ and $R^{S12}$ may be bonded to each other to form a saturated carbocycle or an unsaturated carbocycle. Examples of the saturated carbocycle or the unsaturated carbocycle include naphthalene, azulene, anthracene, fluorene, and phenalene. $R^{S11}$ and $R^{S12}$ are preferably a hydrogen atom, a substituted or unsubstituted alkyl group having 1 to 30 carbon atoms, a substituted or unsubstituted aryl group having 6 to 30 carbon atoms, a substituted or unsubstituted fused polycyclic group having 5 to 30 carbon atoms, or a cyano group, and more preferably a hydrogen atom. $Ar^{S4}$ represents a substituted or unsubstituted aryl group having 6 to 30 carbon atoms, or a substituted or unsubstituted heteroaryl group having 2 to 30 carbon atoms. $Y^{S1}$ and $Y^{S2}$ represent a substituted or unsubstituted alkylene having 1 to 30 carbon atoms, or substituted or unsubstituted arylene having 6 to 30 carbon atoms. $Y^{S1}$ and $Y^{S2}$ are preferably a substituted or unsubstituted arylene having 6 to 30 carbon atoms, and more preferably a substituted or unsubstituted phenylene. n is an integer of 0 to 5, preferably 0 to 3, more preferably 0 to 2, and still more preferably 0. m is an integer of 0 to 5, preferably 0 to 3, more preferably 0 to 2, and still more preferably 1.

The general formula (Sa-1) is preferably a compound represented by the following general formula (Sa-2).

[Chem. 25]

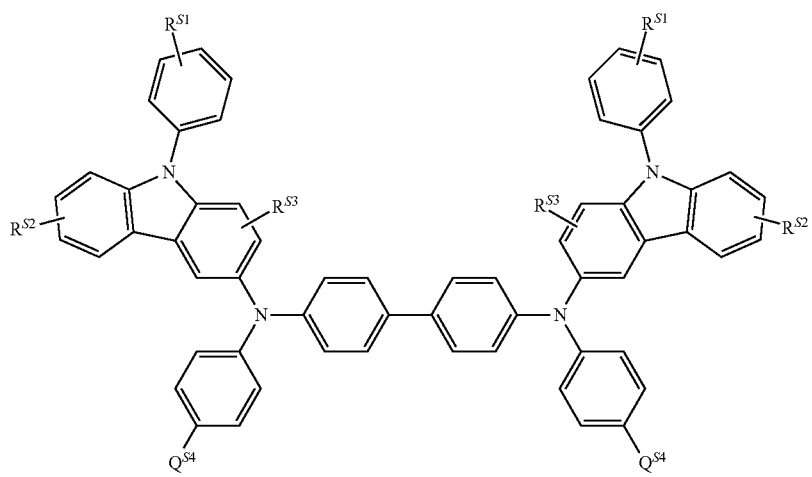

General formula (Sa-2)

(in which $R^{S1}$, $R^{S2}$, and $R^{S3}$ each independently represent a hydrogen atom, a substituted or unsubstituted alkyl group having 1 to 30 carbon atoms, a substituted or unsubstituted alkoxy group having 1 to 30 carbon atoms, a substituted or unsubstituted aryl group having 6 to 30 carbon atoms, a substituted or unsubstituted aryloxy group having 6 to 30 carbon atoms, a substituted or unsubstituted heterocycle having 2 to 30 carbon atoms, a substituted or unsubstituted fused polycyclic group having 5 to 30 carbon atoms, a hydroxy group, a cyano group, or a substituted or unsubstituted amino group. Adjacent $R^{S1}$, $R^{S2}$, and $R^{S3}$ may be bonded to each other to form a saturated carbocycle or an unsaturated carbocycle. $Q^{Sa}$ each independently represent a hydrogen atom, a cyano group, a fluorine atom, an alkoxy group having 1 to 30 carbon atoms, a substituted or unsubstituted alkyl group having 1 to 30 carbon atoms, an aryloxy group having 6 to 30 carbon atoms, a substituted or unsubstituted aryl group having 6 to 30 carbon atoms, a substituted or unsubstituted heterocycle having 2 to 30 carbon atoms, or a substituted or unsubstituted amino group.)

The general formula (Sa-2) will be described. $R^{S1}$, $R^{S2}$, and $R^{S3}$ have the same definitions as those in the general formula (Sa-1), and their preferred ranges are also the same. Each $Q^{Sa}$ independently represents a hydrogen atom, a cyano group, a fluorine atom, an alkoxy group having 1 to 30 carbon atoms, a substituted or unsubstituted alkyl group having 1 to 30 carbon atoms, an aryloxy group having 6 to 30 carbon atoms, a substituted or unsubstituted aryl group having 6 to 30 carbon atoms, a substituted or unsubstituted heterocycle having 2 to 30 carbon atoms, or a substituted or unsubstituted amino group. $Q^{Sa}$ is preferably a hydrogen atom, a cyano group, a fluorine atom, a substituted or unsubstituted alkyl group having 1 to 30 carbon atoms, or a substituted or unsubstituted aryl group having 6 to 30 carbon atoms, more preferably having a hydrogen atom or a substituted or unsubstituted alkyl group having 1 to 30 carbon atoms, and still more preferably a hydrogen atom.

The general formula (Sb-1) is preferably a compound represented by the following general formula (Sb-2).

[Chem. 26]

General formula (Sb-2)

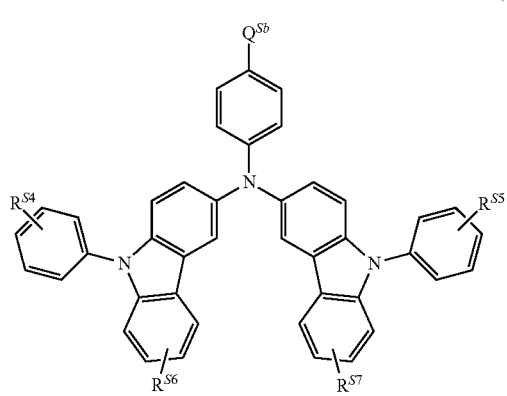

(in which $R^{S4}$, $R^{S5}$, $R^{S6}$ and $R^{S7}$ each independently represent a hydrogen atom, a substituted or unsubstituted alkyl group having 1 to 30 carbon atoms, a substituted or unsubstituted alkoxy group having 1 to 30 carbon atoms, a substituted or unsubstituted aryl group having 6 to 30 carbon atoms, a substituted or unsubstituted aryloxy group having 6 to 30 carbon atoms, a substituted or unsubstituted heterocycle having 2 to 30 carbon atoms, a substituted or unsubstituted fused polycyclic group having 5 to 30 carbon atoms, a hydroxy group, a cyano group, or a substituted or unsubstituted amino group. Adjacent $R^{S4}$, $R^{S5}$, $R^{S6}$ and $R^{S7}$ may be bonded to each other to form a saturated carbocycle or an unsaturated carbocycle. $Q^{Sb}$ represents a hydrogen atom, a cyano group, a fluorine atom, an alkoxy group having 1 to 30 carbon atoms, a substituted or unsubstituted alkyl group having 1 to 30 carbon atoms, an aryloxy group having 6 to 30 carbon atoms, a substituted or unsubstituted aryl group having 6 to 30 carbon atoms, a substituted or unsubstituted heterocycle having 2 to 30 carbon atoms, or a substituted or unsubstituted amino group.)

The general formula (Sb-2) will be described. $R^{S4}$, $R^{S5}$, $R^{S6}$ and $R^{S7}$ have the same definitions as those in the general formula (Sb-1), and their preferred ranges are also the same. $Q^{Sa}$ represents a hydrogen atom, a cyano group, a fluorine atom, an alkoxy group having 1 to 30 carbon atoms, a substituted or unsubstituted alkyl group having 1 to 30 carbon atoms, an aryloxy group having 6 to 30 carbon atoms, a substituted or unsubstituted aryl group having 6 to 30 carbon atoms, a substituted or unsubstituted heterocycle having 2 to 30 carbon atoms, or a substituted or unsubstituted amino group. $Q^{Sa}$ is preferably a hydrogen atom, a cyano group, a fluorine atom, a substituted or unsubstituted alkyl group having 1 to 30 carbon atoms, or a substituted or unsubstituted aryl group having 6 to 30 carbon atoms, more preferably having a hydrogen atom, or a substituted or unsubstituted alkyl group having 1 to 30 carbon atoms, and still more preferably a hydrogen atom.

The general formula (Sa-1) is preferably a compound represented by the following general formula (Sa-2).

[Chem. 27]

General formula (Sc-2)

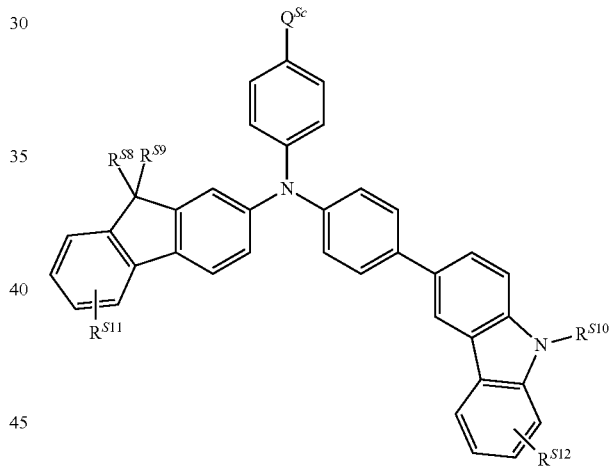

(in which $R^{S8}$ and $R^{S9}$ each independently represent a hydrogen atom, a substituted or unsubstituted alkyl group having 1 to 30 carbon atoms, a substituted or unsubstituted aryl group having 6 to 30 carbon atoms, a substituted or unsubstituted heterocyclic group having 2 to 30 carbon atoms, or a substituted or unsubstituted fused polycyclic group having 5 to 30 carbon atoms. $R^{S10}$ represents a substituted or unsubstituted alkyl group having 1 to 30 carbon atoms, a substituted or unsubstituted aryl group having 6 to 30 carbon atoms, a substituted or unsubstituted heterocyclic group having 2 to 30 carbon atoms, or a substituted or unsubstituted fused polycyclic group having 5 to 30 carbon atoms. $R^{S11}$ and $R^{S12}$ each independently represent a hydrogen atom, a substituted or unsubstituted alkyl group having 1 to 30 carbon atoms, a substituted or unsubstituted alkoxy group having 1 to 30 carbon atoms, a substituted or unsubstituted aryl group having 6 to 30 carbon atoms, a substituted or unsubstituted aryloxy group having 6 to 30 carbon atoms, a substituted or unsubstituted heterocycle having 2 to 30 carbon atoms, or a substituted or unsubstituted fused polycyclic group having 5 to 30 carbon atoms, a hydroxy group, a cyano group, or a substituted or unsubstituted amino group. Adjacent $R^{S11}$ and $R^{S12}$ may be bonded to each other to form a saturated carbocycle or an unsaturated carbocycle. $Q^{Sc}$ represents a hydrogen atom, a cyano group, a fluorine atom, an alkoxy group having 1 to 30 carbon atoms, a substituted or unsubstituted alkyl group having 1 to 30 carbon atoms, an aryloxy group having 6 to 30 carbon atoms, a substituted or unsubstituted aryl group having 6 to 30 carbon atoms, a substituted or unsubstituted heterocycle having 2 to 30 carbon atoms, or a substituted or unsubstituted amino group.)

The general formula (Sa-2) will be described. $R^{S8}$, $R^{S9}$, $R^{S10}$, $R^{S11}$ and $R^{S12}$ have the same definitions as those in the general formula (Sa-1), and their preferred ranges are also the same. $Q^{Sc}$ represents a hydrogen atom, a cyano group, a fluorine atom, an alkoxy group having 1 to 30 carbon atoms, a substituted or unsubstituted alkyl group having 1 to 30 carbon atoms, an aryloxy group having 6 to 30 carbon atoms, a substituted or unsubstituted aryl group having 6 to 30 carbon atoms, a substituted or unsubstituted heterocycle having 2 to 30 carbon atoms, or a substituted or unsubstituted amino group. $Q^{Sc}$ is preferably a hydrogen atom, a cyano group, a fluorine atom, a substituted or unsubstituted alkyl group having 1 to 30 carbon atoms, or a substituted or unsubstituted aryl group having 6 to 30 carbon atoms, more preferably having a hydrogen atom, or a substituted or unsubstituted aryl group having 6 to 30 carbon atoms, and still more preferably a phenyl group.

Specific examples of the compounds represented by the general formulae (Sa-1), (Sb-1), and (Sc-1) include the following ones. However, the present invention is not limited to the following specific examples.

[Chem. 28]

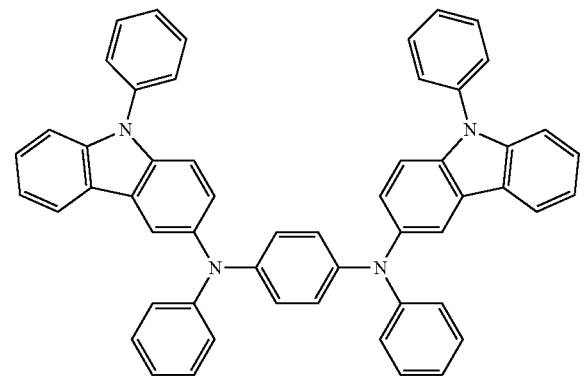

1

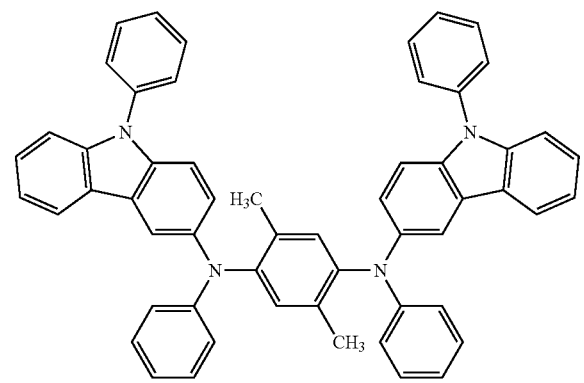

2

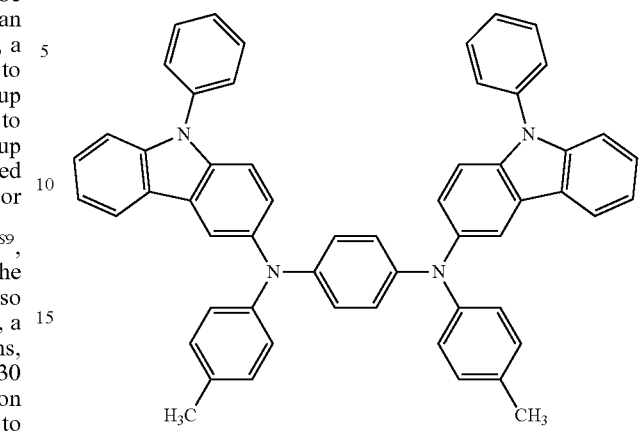

-continued

6
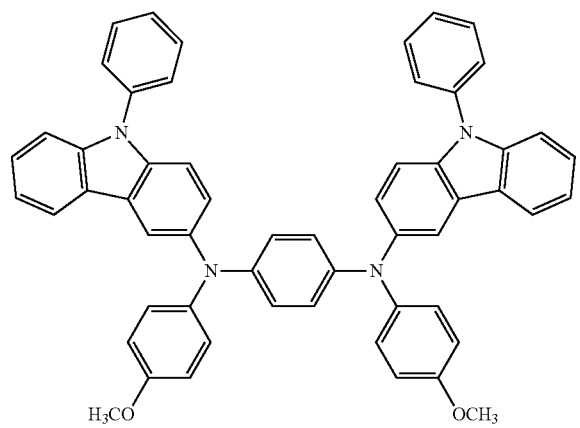
7
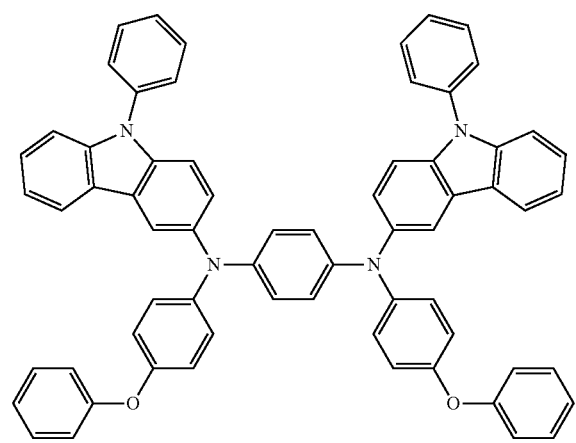
8
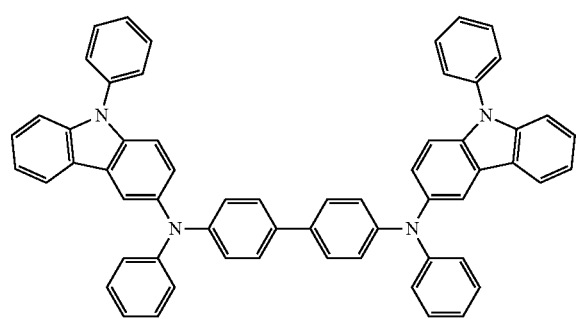
[Chem. 29]
9
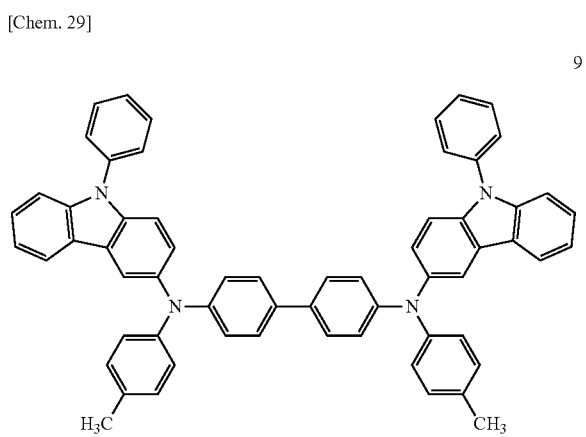
10
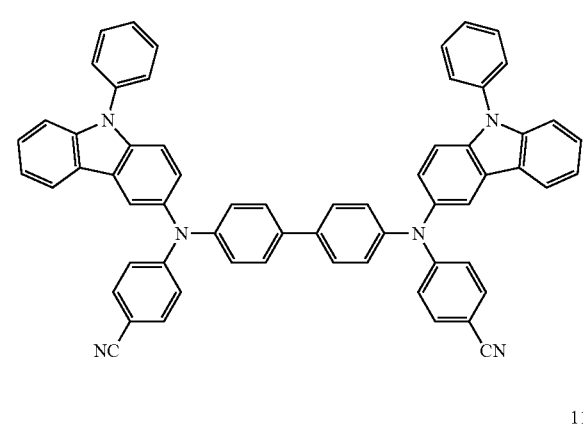
11
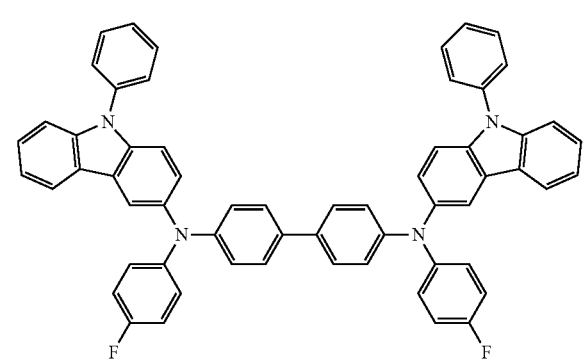
12
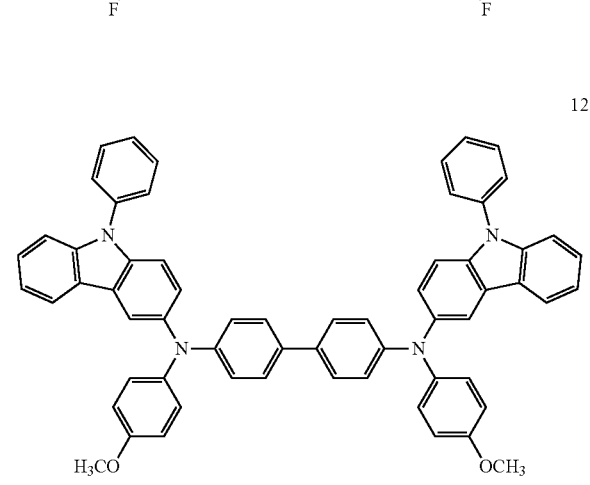
13
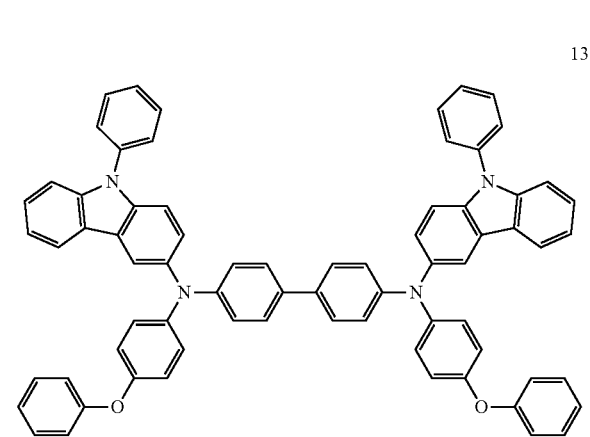

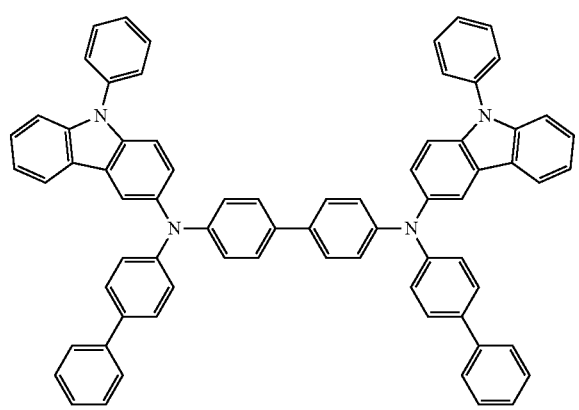
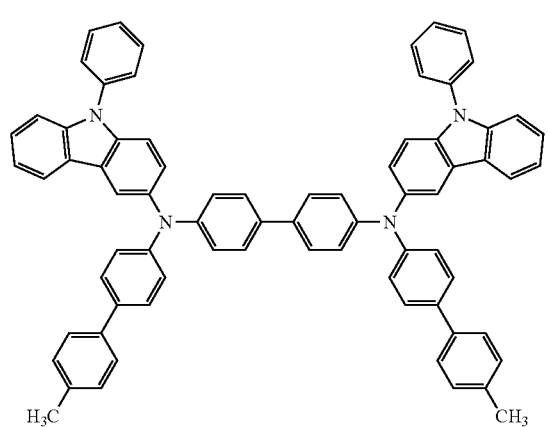
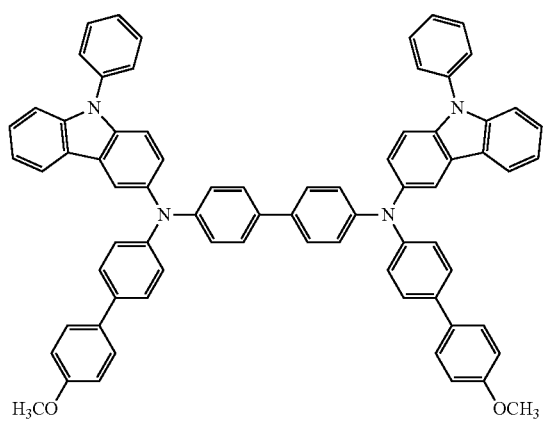

20
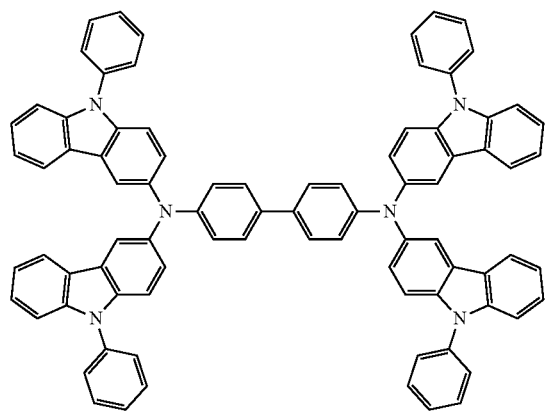
23
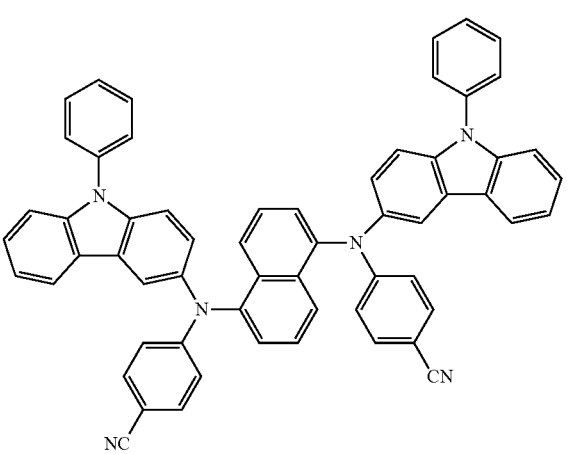
[Chem. 31]
21
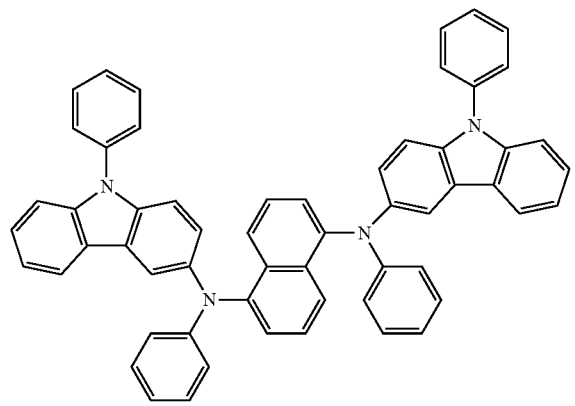
24
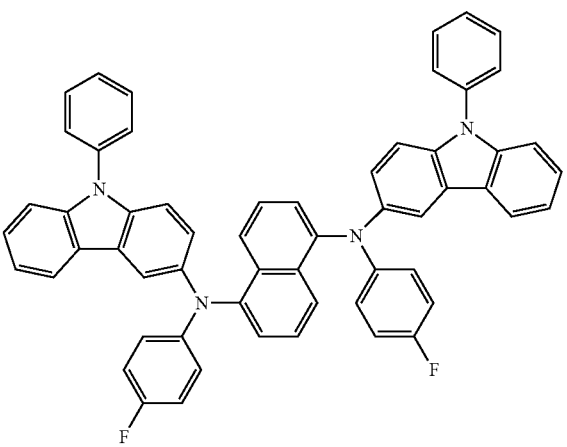
22
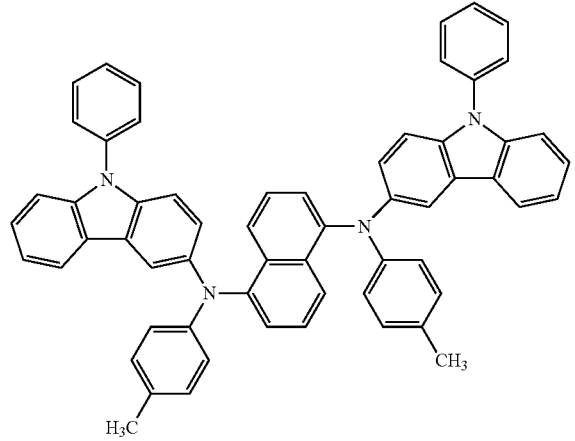
25
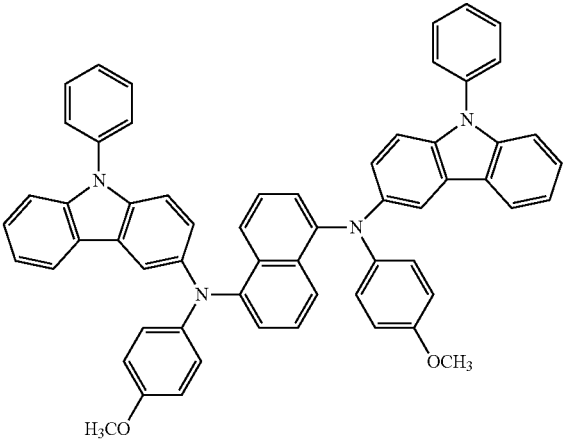

[Chem. 32]

[Chem. 33]
33
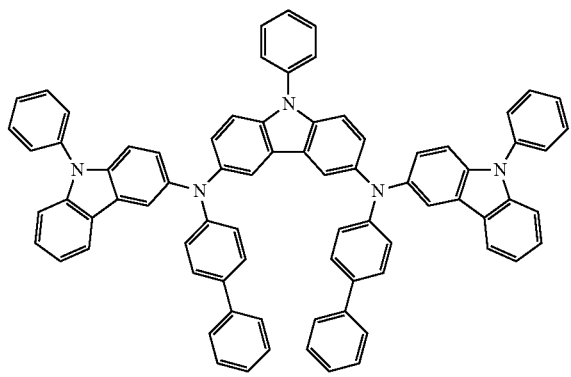
34
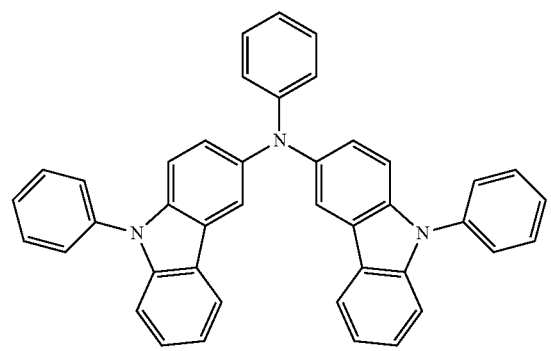
35
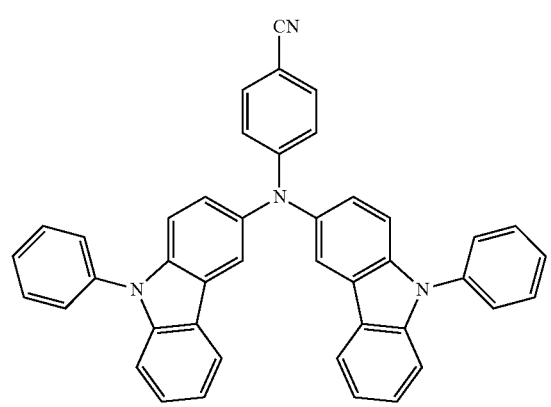
36
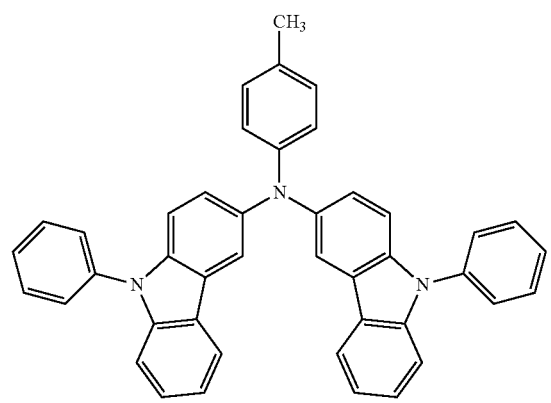
37
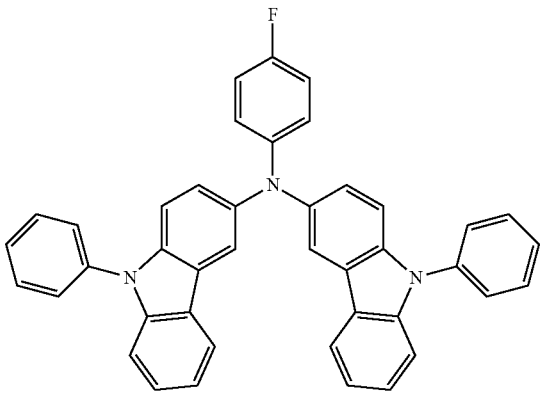
38
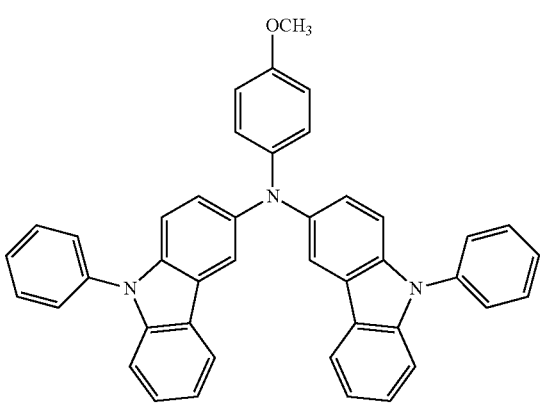
[Chem. 34]
39
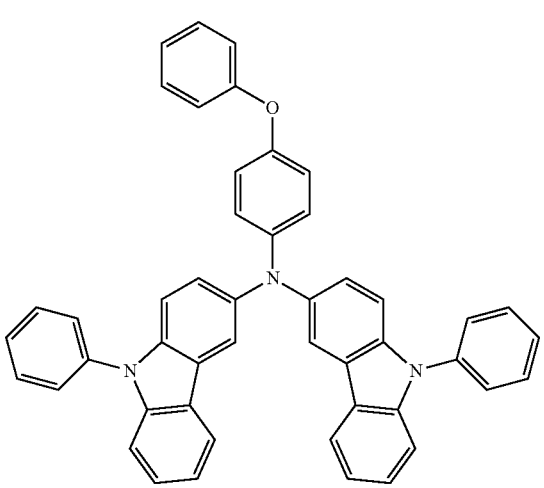

40
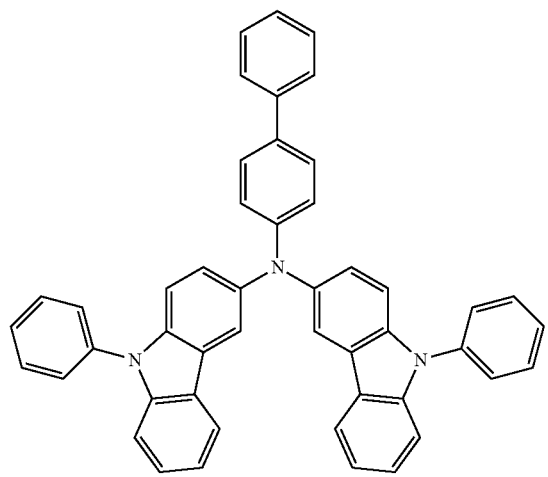
41
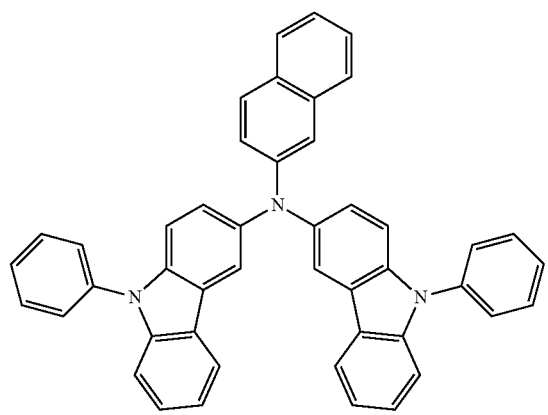
42
[Chem. 35]
43
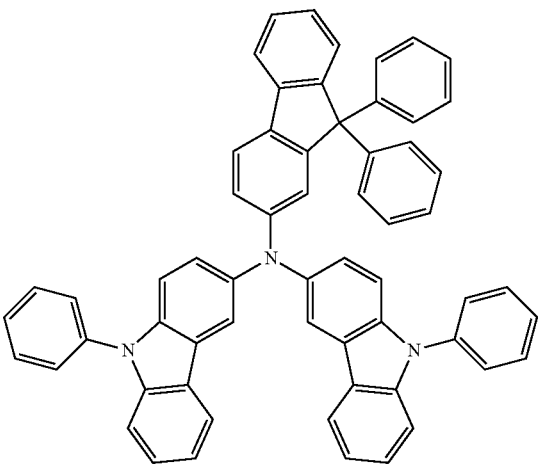
44
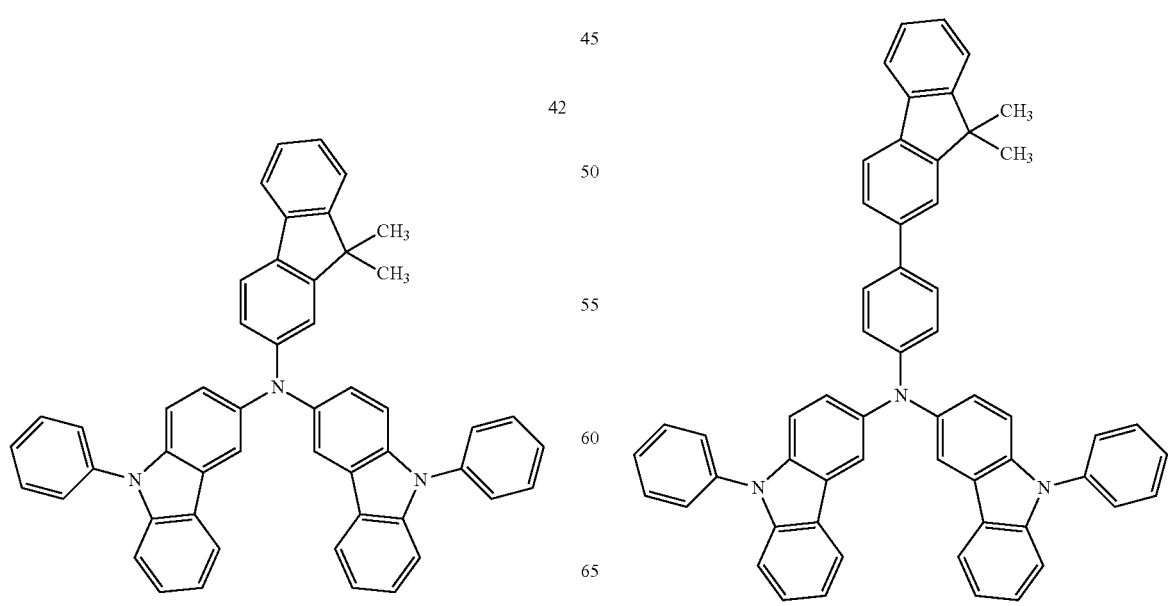

45
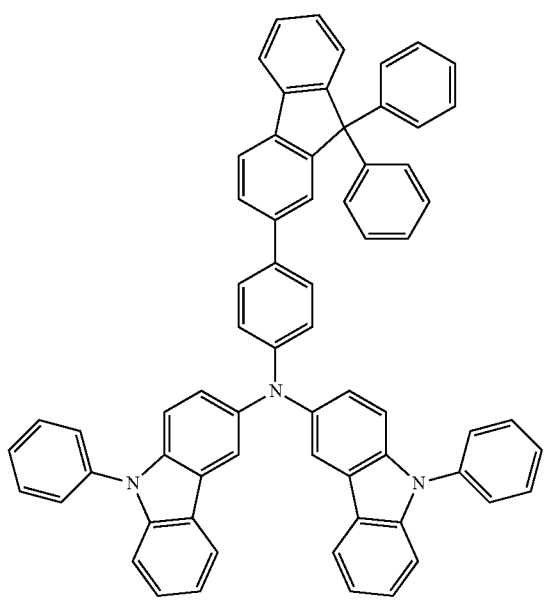
48
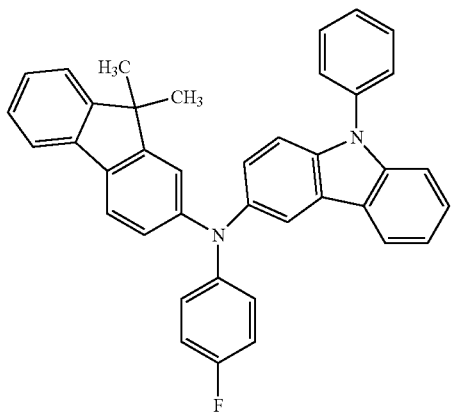
46
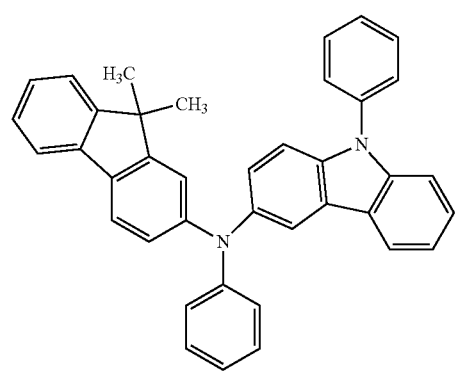
49
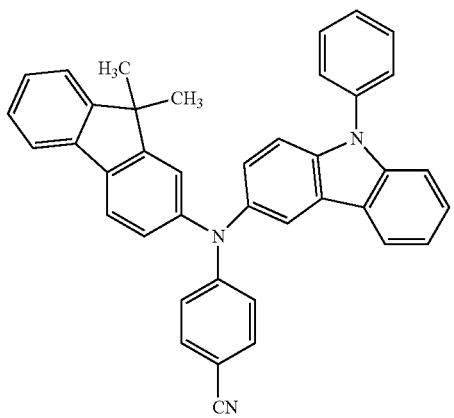
[Chem. 36]
47
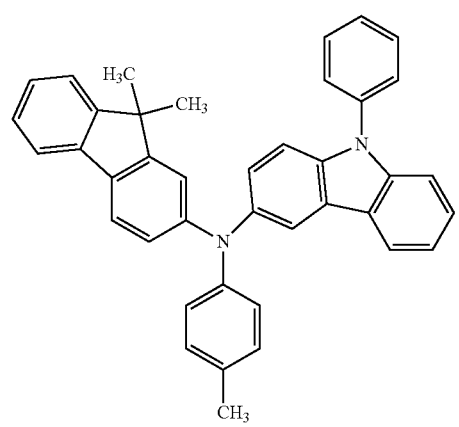
50
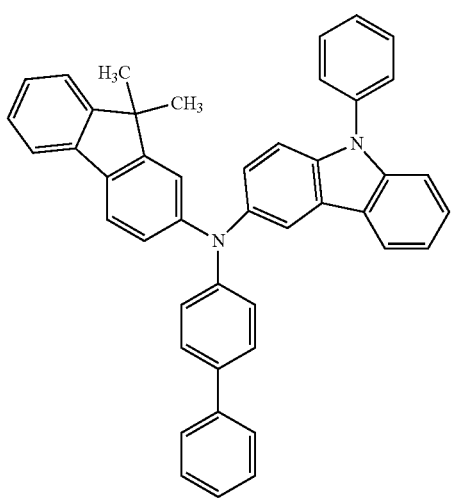

51
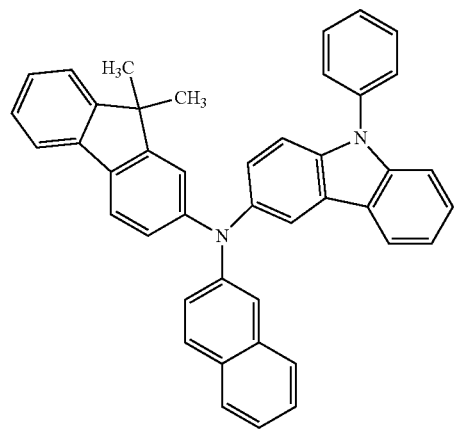
52
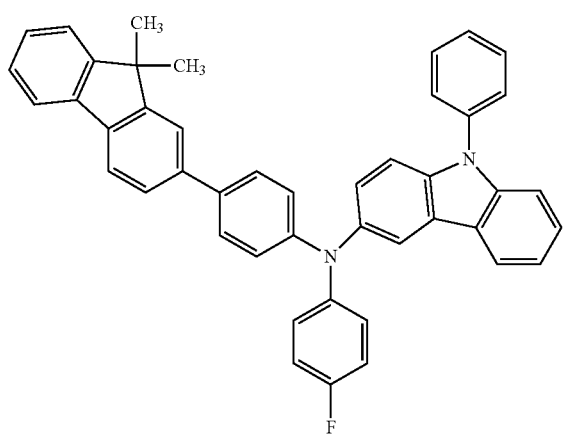
53
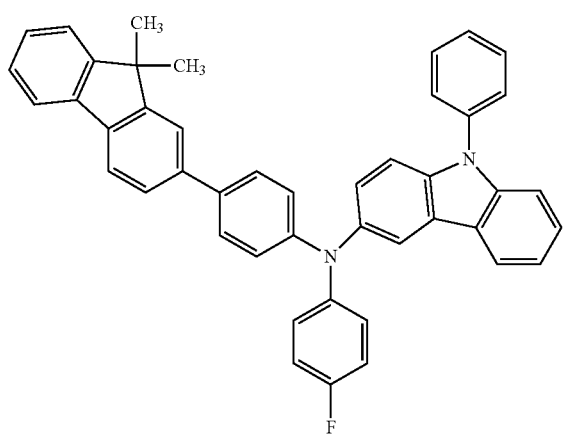
[Chem. 37]
54
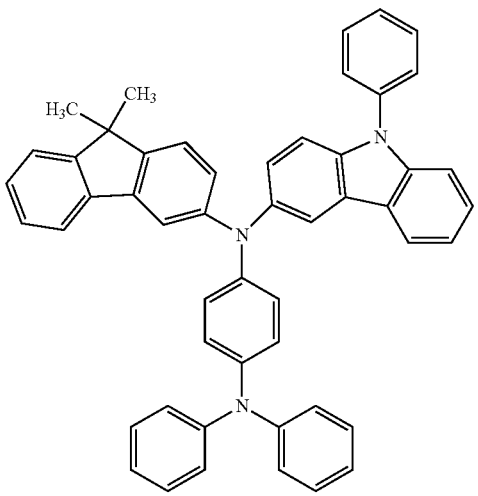
55
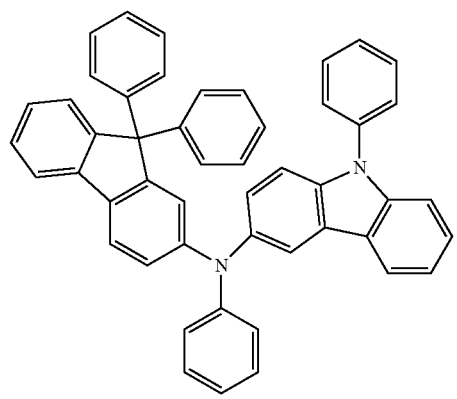
56
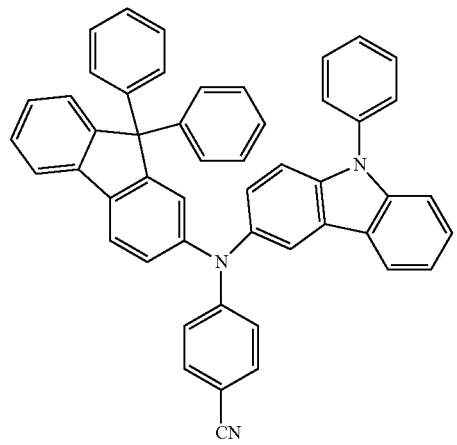

57
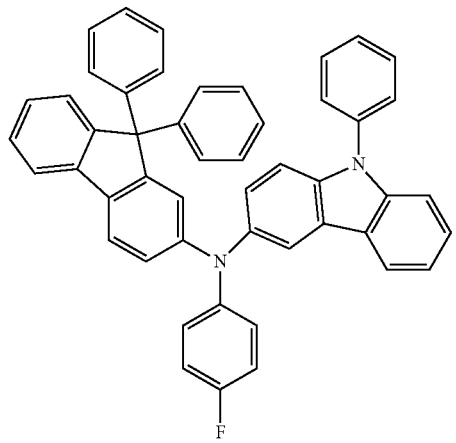
58
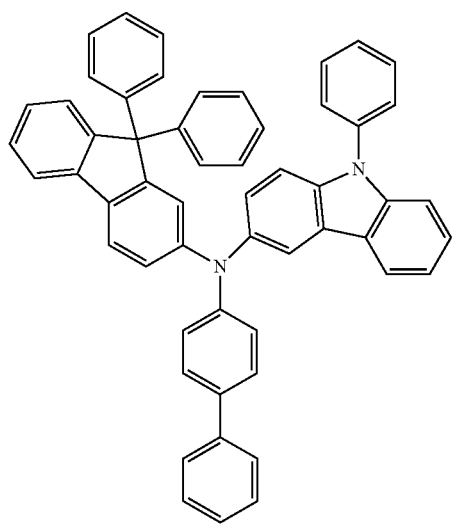
59
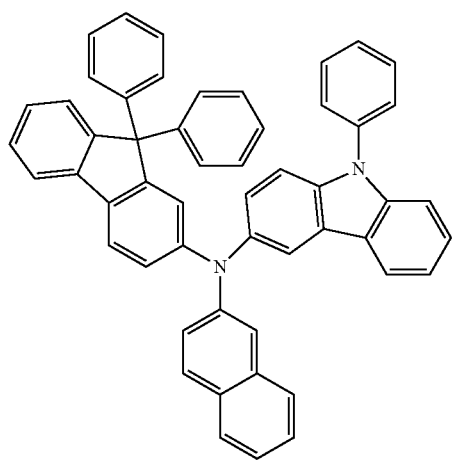
60
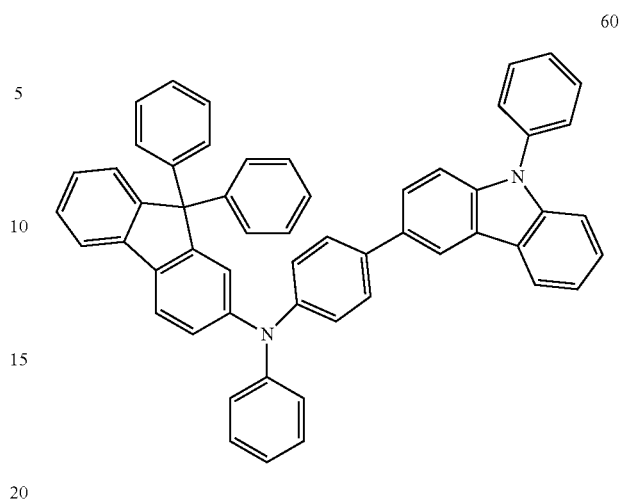
61
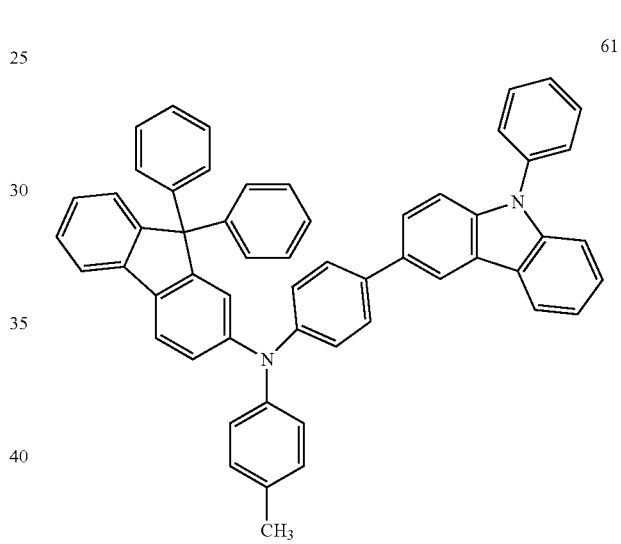
62
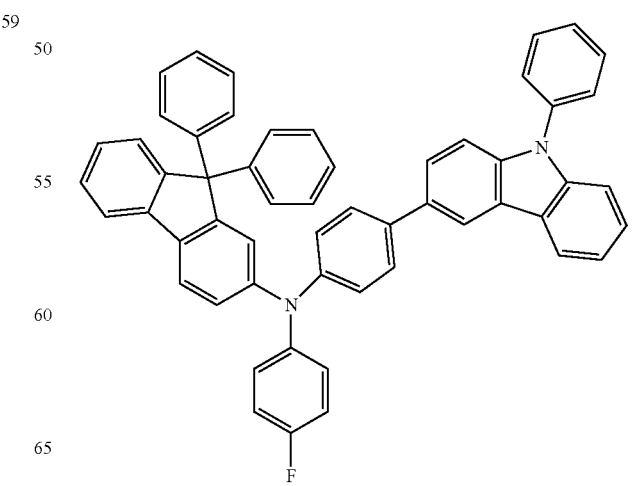

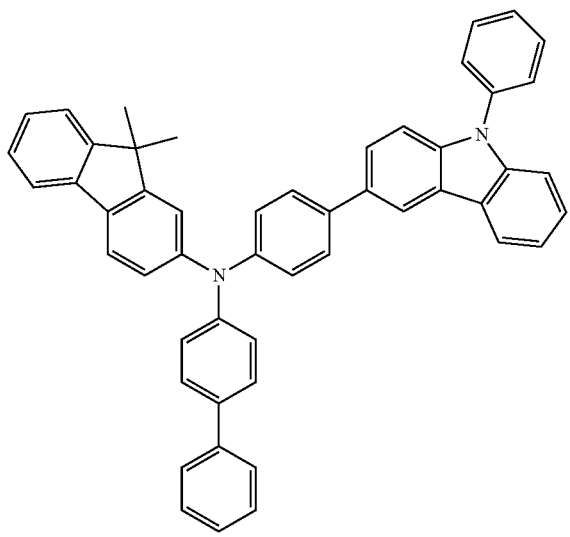

The compound represented by the general formula (Sa-1), (Sb-1), or (Sc-1) can be synthesized by the method described in JP-A-2007-318101. After the synthesis, purification is preferably carried out by column chromatography, recrystallization, reprecipitation, or the like, and then by sublimation purification. By the sublimation purification, organic impurities can be separated and inorganic salts, residual solvents, moisture, or the like can be removed effectively.

In the light emitting element of the present invention, the compound represented by the general formula (Sa-1), (Sb-1), or (Sc-1) is preferably included in the organic layer between the light emitting layer and the anode, and above all, it is more preferably included in the layer on the anode side adjacent to the light emitting layer, and it is particularly preferably a hole transporting material included in the hole transporting layer.

The compound represented by the general formula (Sa-1), (Sb-1), or (Sc-1) is preferably contained in the amount of 70% by mass to 100% by mass, and more preferably 85% by mass to 100% by mass, with respect to the total mass of the organic layer added.

With respect to the hole injecting layer and the hole transporting layer, the detailed descriptions in paragraph Nos. to [0167] of JP-A-2008-270736 can be applied to the present invention.

The hole injecting layer preferably contains an electron receptive dopant. By incorporating the electron receptive dopant in the hole injecting layer, there are effects in which, for example, the hole injecting properties are improved, the driving voltage is lowered, and the efficiency is improved. The electron receptive dopant may be any one of organic materials and inorganic materials as long as it is capable of withdrawing electrons from a material to be doped and generating radical cations, and examples thereof include tetracyanoquinodimethane (TCNQ), tetrafluorotetracyanoquinodimethane ($F_4$-TCNQ) f and molybdenum oxide.

The electron receptive dopant in the hole injecting layer is contained in the amount of preferably from 0.01% by mass to 50% by mass, more preferably from 0.1% by mass to 40% by mass, and still more preferably from 0.2% by mass to 30% by mass, with respect to the total mass of the compounds forming the hole injecting layer (A-2) Electron Blocking Layer The electron blocking layer is a layer having a function of preventing the electrons, which have been transported from the cathode side to the light emitting layer, from passing through to the anode side. In the present invention, the electron blocking layer can be provided as an organic layer adjacent to the light emitting layer on the anode side.

As the organic compound constituting the electron blocking layer, for example, those exemplified above as the hole transporting material can be used.

The thickness of the electron blocking layer is preferably from 1 nm to 500 nm, more preferably from 3 nm to 100 nm, and still more preferably from 5 nm to 50 nm.

The electron blocking layer may have either a single layer structure composed of one or two or more kinds of materials selected from the above-exemplified materials or a multilayer structure composed of a plurality of layers having the same composition or different compositions.

The material used in the electron blocking layer preferably has higher $S_1$ energy than that of the light emitting material from the viewpoints of color purity, luminous efficiency, and driving durability. The $S_1$ in the film state of the material used in the electron blocking layer is preferably higher than the $S_1$ of the light emitting material by 0.1 eV or more, more preferably by 0.2 eV or more, and still more preferably by 0.3 eV or more.

(B) Organic Layer Preferably Disposed Between Cathode and Light Emitting Layer

Next, the (B) organic layer preferably disposed between the cathode and the light emitting layer will be described.

(B-1) Electron Injecting Layer and Electron Transporting Layer

The electron injecting layer and the electron transporting layer are layers having a function of receiving electrons from the cathode or the cathode side and transporting them to the anode side. The electron injecting material and the electron transporting material used in these layers may be either a low-molecular compound or a high-molecular compound.

As the electron transporting material, for example, the compound represented by the general formula (I) can be used. As the other electron transporting materials, any one selected from aromatic ring tetracarboxylic acid anhydrides, such as pyridine derivatives, quinoline derivatives, pyrimidine derivatives, pyrazine derivatives, phthalazine derivatives, phenanthroline derivatives, triazine derivatives, triazole derivatives, oxazole derivatives, oxadiazole derivatives, imidazole derivatives, benzimidazole derivatives, imidazopyridine derivatives, fluorenone derivatives, anthraquinodimethane derivatives, anthrone derivatives, diphenylquinone derivatives, thiopyranedioxide derivatives, carbodiimide derivatives, fluorenylidenemethane derivatives, distyrylpyrazine derivatives, naphthalene, and perylene; various metal complexes typified by metal complexes of phthalocyanine derivatives or 8-quinolinol derivatives and metal complexes having metal phthalocyanine, benzoxazole, or benzothiazole as a ligand thereof, organic silane derivatives typified by silole, hydrocarbon compounds with fused rings, such as naphthalene, anthracene, phenanthrene, triphenylene, and pyrene is preferred, and any one selected from pyridine derivatives, benzimidazole derivatives, imidazopyridine derivatives, metal complexes, and hydrocarbon compounds with fused rings is more preferred.

From the viewpoint of decreasing the driving voltage, the thickness of each of the electron injecting layer and the electron transporting layer is preferably 500 nm or less.

The thickness of the electron transporting layer is preferably from 1 nm to 500 nm, more preferably from 5 nm to 200 nm, and still more preferably from 10 nm to 100 nm. In addition, the thickness of the electron injecting layer is preferably from 0.1 nm to 200 nm, more preferably from 0.2 nm to 100 nm, and still more preferably from 0.5 nm to 50 nm.

The electron injecting layer and the electron transporting layer may have either a single layer structure composed of one or two or more kinds of the above-described materials or a multilayer structure composed of a plurality of layers having the same composition or different compositions.

The electron injecting layer preferably contains an electron donating dopant. By incorporating the electron donating dopant in the electron injecting layer, there are effects that, for example, the electron injecting properties are improved, the driving voltage is lowered, and the efficiency is improved. The electron donating dopant may be any one of organic materials and inorganic materials as long as it is capable of giving electrons to the material to be doped and generating radical anions, and examples thereof include dihydroimidazole compounds such as tetrathiafulvalene (TTF), tetrathianaphthacene (TTT), and bis-[1,3-d]ethyl-2-methyl-1,2-dihydrobenzimidazolyl], lithium, and cesium.

The electron donating dopant in the electron injecting layer is contained in the amount of preferably from 0.01% by mass to 50% by mass, more preferably from 0.1% by mass to 40% by mass, and still more preferably 0.5% by mass to 30% by mass, with respect to the total mass of the compounds forming the electron injecting layer.

(B-2) Hole Blocking Layer

The hole blocking layer is a layer having a function of preventing holes, which have been transported from the anode side to the light emitting layer, from passing through to the cathode side. In the present invention, the hole blocking layer can be provided as an organic layer adjacent to the light emitting layer on the cathode side.

In order that the $S_1$ energy of the organic compound in the film state constituting the hole blocking layer prevents the energy movement of excitons produced in the light emitting layer, and thus, does not lower the luminous efficiency, it is preferably higher than $S_1$ energy of the light emitting material.

As an example of the organic compound constituting the hole blocking layer, for example, the compound represented by the general formula (I) can be used.

Examples of the organic compounds constituting the hole blocking layer, other than the compound represented by the general formula (I), include aluminum complexes such as aluminum (III) bis(2-methyl-8-quinolinato) 4-phenylphenolate (abbreviated as Balq), triazole derivatives, and phenanthroline derivatives such as 2,9-dimethyl-4,7-diphenyl-1,10-phenanthroline (abbreviated as BCP).

The thickness of the hole blocking layer is preferably from 1 nm to 500 nm, more preferably from 3 nm to 100 nm, and still more preferably from 5 nm to 50 nm.

The hole blocking layer may have either a single layer structure composed of one or two or more kinds of the above-described materials or a multilayer structure composed of a plurality of layers having the same composition or different compositions.

The material used in the hole blocking layer preferably has higher $S_1$ energy than that of the light emitting material from the viewpoints of color purity, luminous efficiency, and driving durability. The $S_1$ in the film state of the material used in the hole blocking layer is preferably higher than the $S_1$ of the light emitting material by 0.1 eV or more, more preferably by 0.2 eV or more, and still more preferably by 0.3 eV or more.

(B-3) Material which is Particularly Preferably Used in Organic Layer, Preferably Disposed Between Cathode and Light Emitting Layer For the organic electroluminescent element of the present invention, examples of the material which is particularly preferably used in the (B) materials for an organic layer, preferably disposed between the cathode and the light emitting layer include the compound represented by the general formula (I), a compound represented by the following general formula (P-1), and a compound represented by the following general formula (O-1).

Hereinafter, a compound represented by the general formula (O-1) and a compound represented by the general formula (P-1) will be described.

The organic electroluminescent element of the present invention preferably includes at least one organic layer between the light emitting layer and the cathode, and the organic layer preferably contains at least one of compounds represented by the following general formula (O-1), from the viewpoint of efficiency or driving voltage of an element. Hereinafter, the general formula (O-1) will be described.

[Chem. 38]

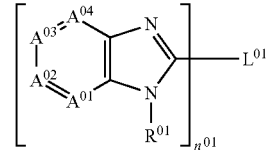

(In the general formula (O-1), $R^{O1}$ represents an alkyl group, an aryl group, or a heteroaryl group. $A^{O1}$ to $A^{O4}$ each independently represent C—$R^A$ or a nitrogen atom. $R^A$ represents a hydrogen atom, an alkyl group, an aryl group, or a heteroaryl group, and a plurality of $R^A$'s may be the same as or different from each other. $L^{O1}$ represents any of divalent to hexavalent linking groups with an aryl ring or a heteroaryl ring. $n^{O1}$ represents an integer of 2 to 6).

$R^{O1}$ represents an alkyl group (preferably having 1 to 8 carbon atoms), an aryl group (preferably having 6 to 30 carbon atoms), or a heteroaryl group (preferably having 4 to 12 carbon atoms), which may have a substituent selected from the above-described Substituent Group A. $R^{O1}$ is preferably an aryl group or a heteroaryl group, and more preferably an aryl group. Preferred examples of the substituent in the case where the aryl group of $R^{O1}$ has a substituent include an alkyl group, an aryl group, and a cyano group, more preferably an alkyl group and an aryl group, and still more preferably an aryl group. In the case where the aryl group of $R^{O1}$ has a plurality of substituents, the plurality of substituents may be bonded to each other to form a 5- or 6-membered ring. The aryl group of $R^{O1}$ is preferably a phenyl group which may have a substituent selected from Substituent Group A, more preferably a phenyl group which may be substituted with an alkyl group or an aryl group, and still more preferably an unsubstituted phenyl group or 2-phenylphenyl group.

$A^{O1}$ to $A^{O4}$ each independently represent C—$R^A$ or a nitrogen atom. It is preferable that 0 to 2 groups out of $A^{O1}$ to $A^{O4}$ be nitrogen atoms; and it is more preferable that 0 or 1 member out of $A^{O1}$ to $A^{O4}$ be nitrogen atoms. It is preferable that all of $A^{O1}$ to $A^{O4}$ be C—$R^A$, or $A^{O1}$ be a nitrogen atom, and $A^{O2}$ to $A^{O4}$ are C—$R^A$; it is more preferable that $A^{O1}$ be a nitrogen atom, and $A^{O2}$ to $A^{O4}$ be C—$R^A$; it is still more preferable that $A^{O1}$ be a nitrogen atom, $A^{O2}$ to $A^{O4}$ be C—$R^A$, and $R^A$'s be all hydrogen atoms.

$R^A$ represents a hydrogen atom, an alkyl group (preferably having 1 to 8 carbon atoms), an aryl group (preferably having 6 to 30 carbon atoms), or a heteroaryl group (preferably having 4 to 12 carbon atoms), and may have a substituent selected from the above-described Substituent Group A. Further, a plurality of $R^A$'s may be the same as or different from each other. $R^A$ is preferably a hydrogen atom or an alkyl group, and more preferably a hydrogen atom.

$L^{O1}$ represents any of a divalent to hexavalent linking group including an aryl ring (preferably having 6 to 30 carbon atoms) or a heteroaryl ring (preferably having 4 to 12 carbon atoms.) $L^{O1}$ is preferably an arylene group, a heteroarylene group, an aryltriyl group, or a heteroaryltriyl group, more preferably a phenylene group, a biphenylene group, or a benzenetriyl group, and still more preferably a biphenylene group or a benzenetriyl group. $L^{O1}$ may have a substituent selected from the above-described Substituent Group A, and in a case of having the substituent, the substituent is preferably an alkyl group, an aryl group, or a cyano group. Specific examples of $L^{O1}$ include the following.

[Chem. 39]

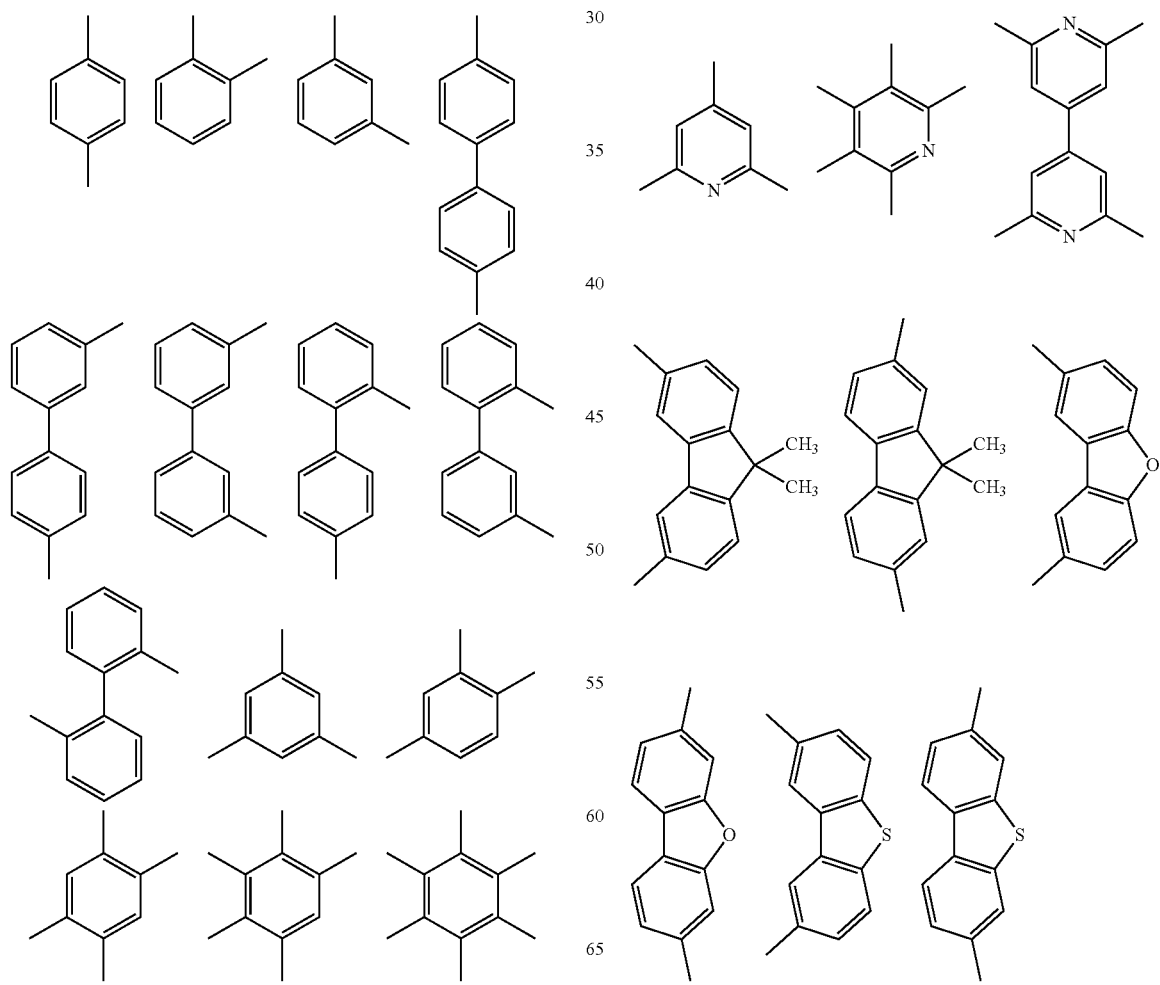

-continued

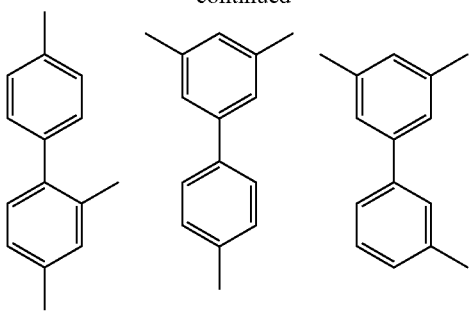

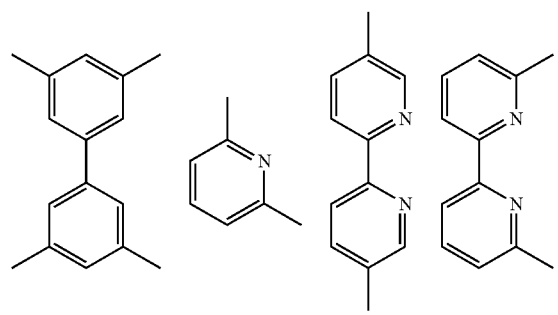

-continued

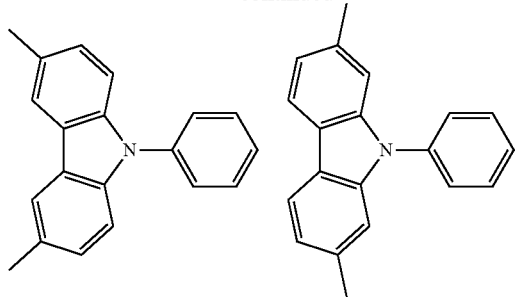

$n^{O1}$ represents an integer of 2 to 6, preferably an integer of 2 to 4, and more preferably 2 or 3. $n^{O1}$ is most preferably 3 from the viewpoint of the efficiency of an element, or most preferably 2 from the viewpoint of the durability of an element.

The glass transition temperature (Tg) of the compound represented by the general formula (O-1) is preferably from 100° C. to 300° C., more preferably from 120° C. to 300° C., still more preferably from 120° C. to 300° C., and even still more preferably from 140° C. to 300° C., from the viewpoint of stability at the time of storage at a high temperature, or stable operation during driving at a high temperature or against heat generation during driving.

Specific examples of the compound represented by the general formula (O-1) are shown below, but the compound represented by the general formula (O-1), which can be used in the present invention, should not be construed to be limited to the specific examples.

[Chem. 40]

OM-1

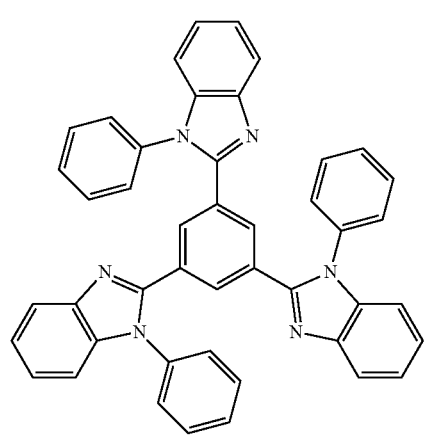

OM-2

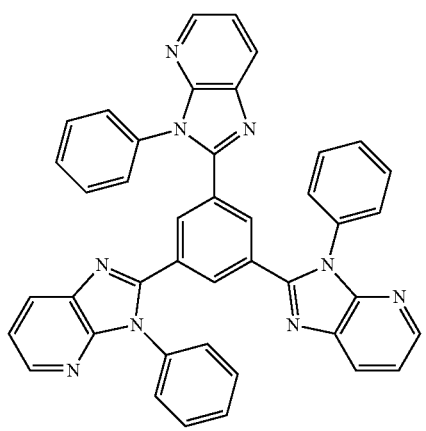

OM-3

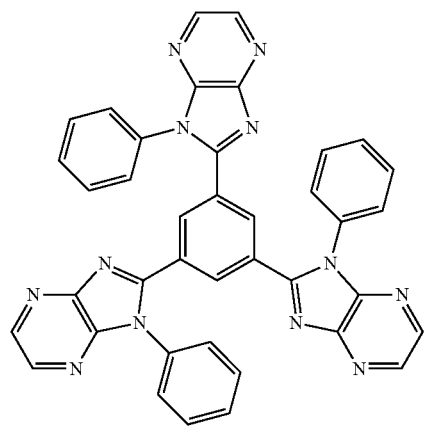

OM-4

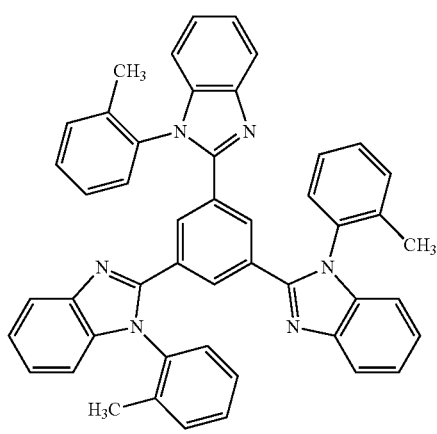

-continued
OM-5
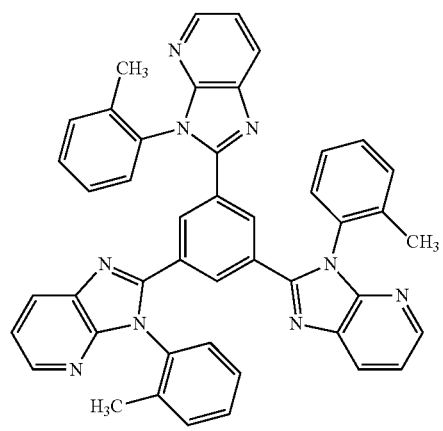
OM-6
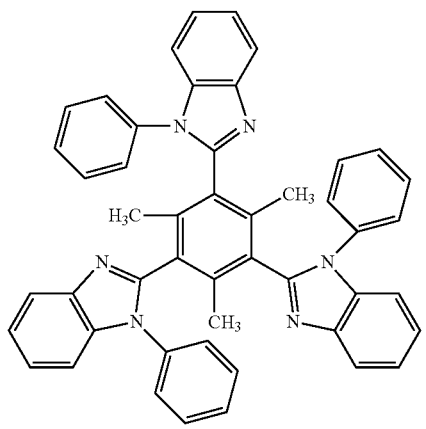
OM-7
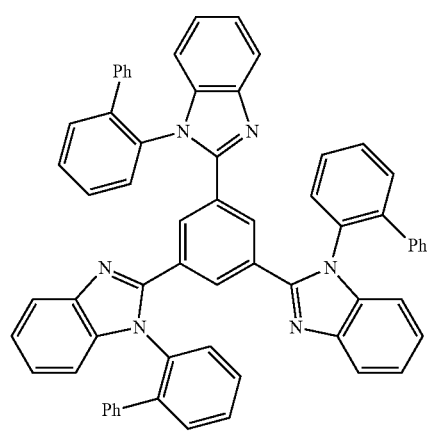
OM-8
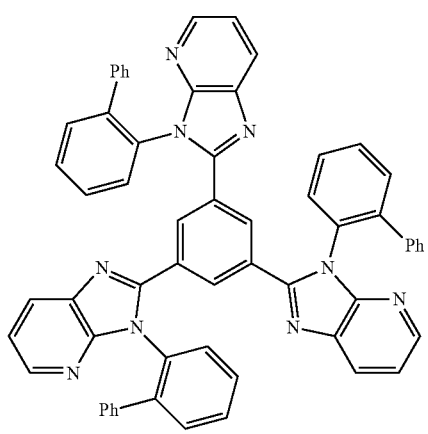
OM-9
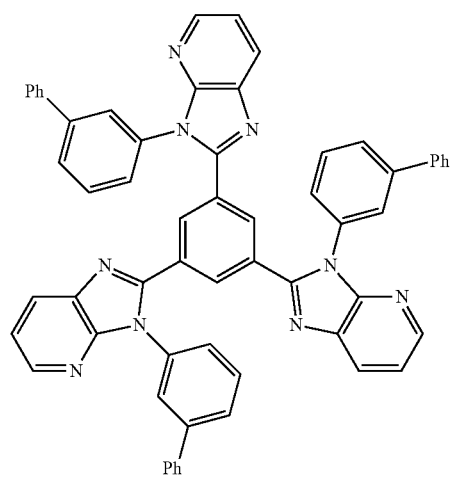

[Chem. 41]
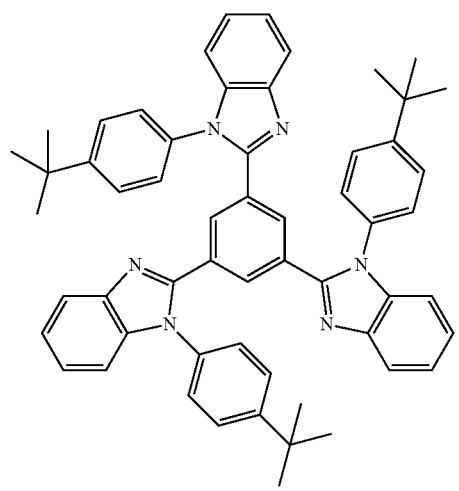
OM-10
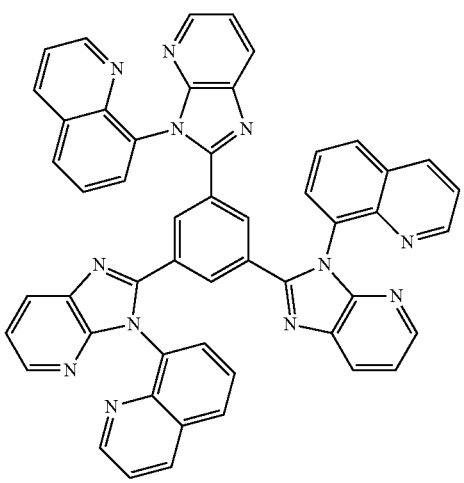
OM-11
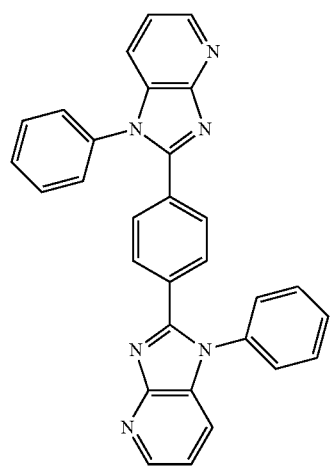
OM-12
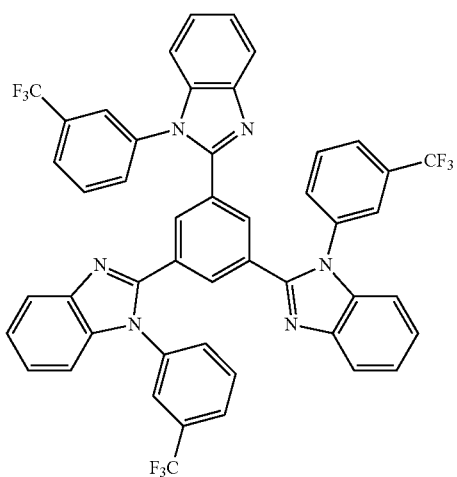
OM-13
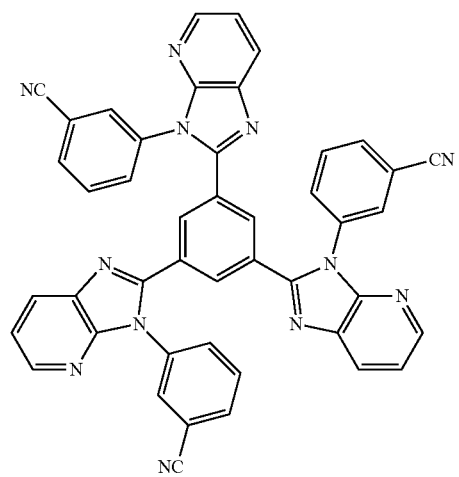
OM-14
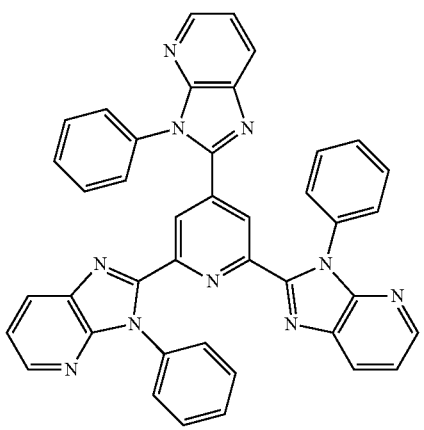
OM-15

-continued

OM-16
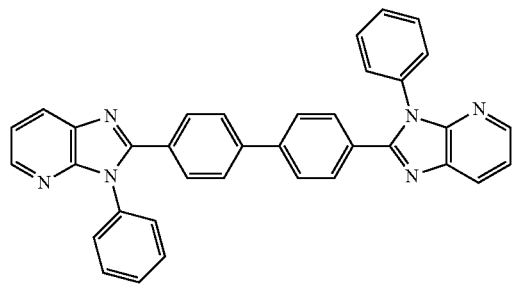

OM-17
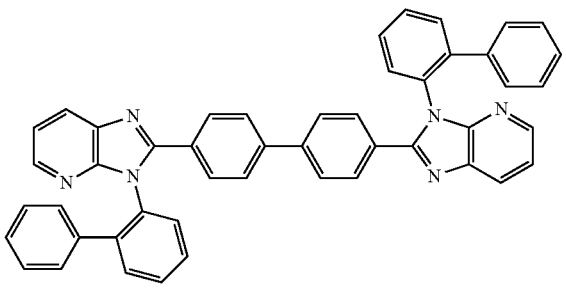

OM-18
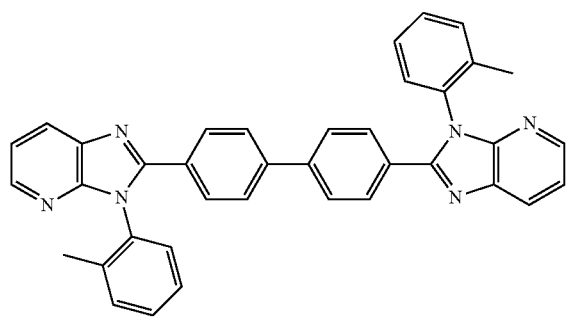

OM-19
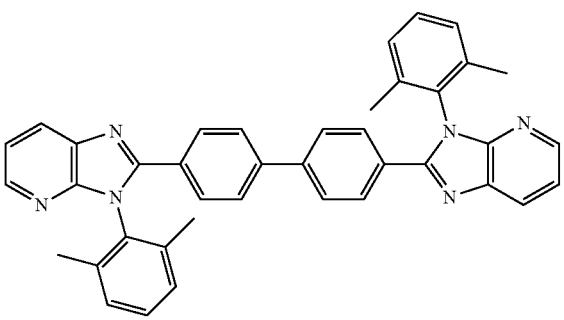

OM-20
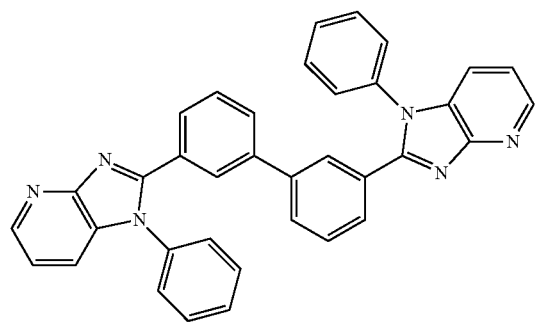

OM-21
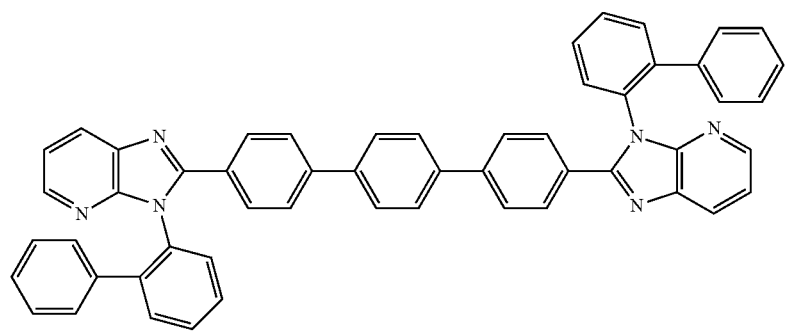

OM-22
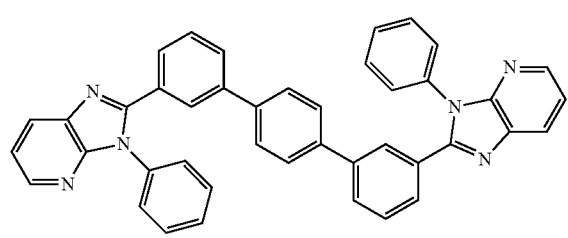

The compound represented by the general formula (O-1) can be synthesized by the method described in JP-A-2001-335776. After the synthesis, purification is preferably carried out by column chromatography, recrystallization, reprecipitation, or the like, and then by sublimation purification. By the sublimation purification, organic impurities can be separated and inorganic salts, residual solvents, moisture, or the like can be removed effectively.

In the organic electroluminescent element of the present invention, the compound represented by the general formula (O-1) is preferably included in the organic layer between the light emitting layer and the cathode, however, it is more preferably included in the layer on the cathode side adjacent to the light emitting layer.

The compound represented by the general formula (O-1) is preferably contained in the amount of 70% by mass to 100% by mass, and more preferably 85% by mass to 100% by mass, with respect to the total mass of the organic layer added.

The organic electroluminescent element of the present invention preferably includes at least one layer of organic layers between the light emitting layer and the cathode, and it is preferable that the organic layer contain at least one of compounds represented by the following general formula (P), from the viewpoint of efficiency or the driving voltage of an element. Hereinafter, the general formula (P) will be described.

[Chem. 42]

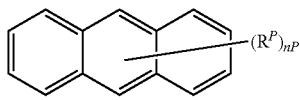

General formula (P)

(In the general formula (P), $R^P$ represents an alkyl group (preferably having 1 to 8 carbon atoms), an aryl group (preferably having 6 to 30 carbon atoms), or a heteroaryl group (preferably having 4 to 12 carbon atoms), which may have a substituent selected from the above-described Substituent Group A. nP represents an integer of 1 to 10, and in the case where there are a plurality of $R^P$'s, these may be the same as or different from each other. At least one of $R^P$'s is a substituent represented by the following general formulae (P-1) to (P-3).

[Chem. 43]

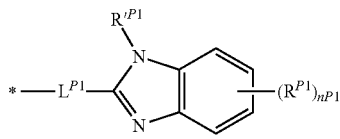

General formula (P-1)

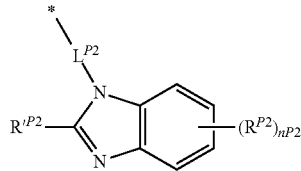

General formula (P-2)

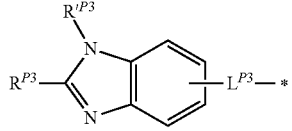

General formula (P-3)

(In the general formulae (P-1) to (P-3), $R^{P1}$ to $R^{P3}$ and $R^{iP1}$ to $R^{iP3}$ each represent an alkyl group (preferably having 1 to 8 carbon atoms), an aryl group (preferably having 6 to 30 carbon atoms), or a heteroaryl group (preferably having 4 to 12 carbon atoms), which may have a substituent selected from the above-described Substituent Group A. $n^{P1}$ and $n^{P2}$ represent an integer of 0 to 4, and in the case where there are a plurality of $R^{P1}$ to $R^{P3}$ and $R^{iP1}$ to $R^{iP3}$, these may be the same as or different from each other. $L^{P1}$ to $L^{P3}$ represent any one of divalent linking groups consisting of a single bond, an aryl ring, or a heteroaryl ring. * represents a binding position with the anthracene ring of the general formula (P)).

A preferred substituent other than the substituents represented by (P-1) to (P-3) as $R^P$ is an aryl group, more preferably any one of a phenyl group, a biphenyl group, a terphenyl group, and a naphthyl group, and still more preferably a naphthyl group.

$R^{P1}$ to $R^{P3}$ and $R^{iP1}$ to $R^{iP3}$ are preferably any one of an aryl group and a heteroaryl group, more preferably an aryl group, still more preferably any one of a phenyl group, a biphenyl group, a terphenyl group, and a naphthyl group, and most preferably a phenyl group.

$L^{P1}$ to $L^{P3}$ are preferably any one of divalent linking groups consisting of a single bond and an aryl ring, more preferably any one of a single bond, phenylene, biphenylene, terphenylene, and naphthylene, and still more preferably any one of a single bond, phenylene, and naphthylene.

Specific examples of the compound represented by the general formula (P) are shown below, but the compound represented by the general formula (P) that can be used in the present invention should not be construed to be limited to the specific examples.

[Chem. 44]

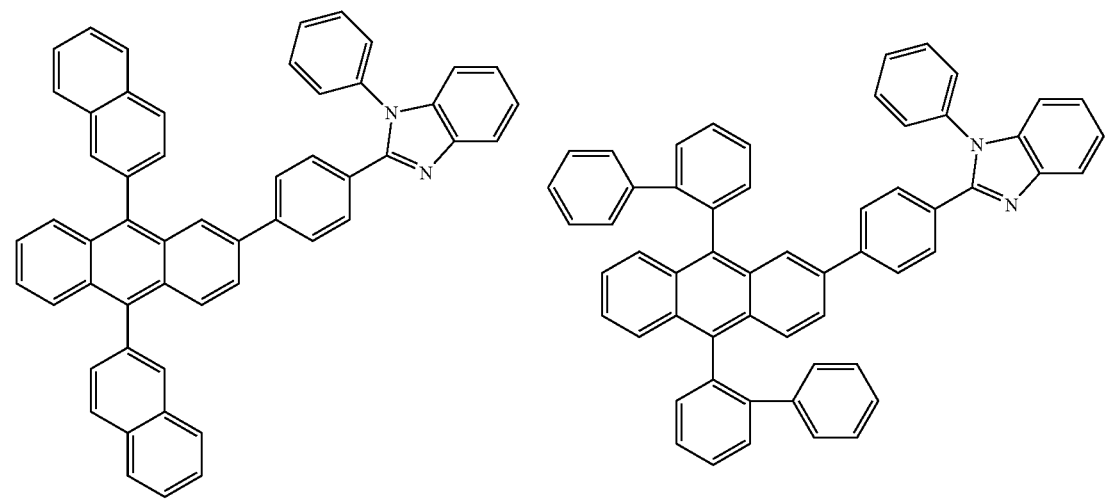

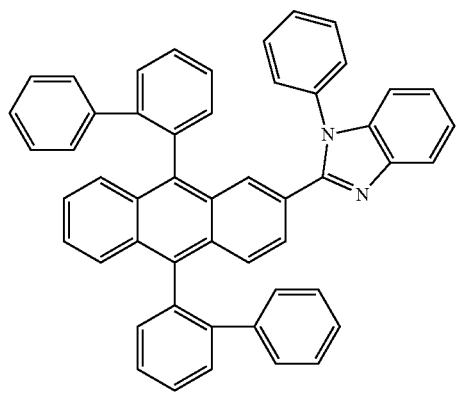
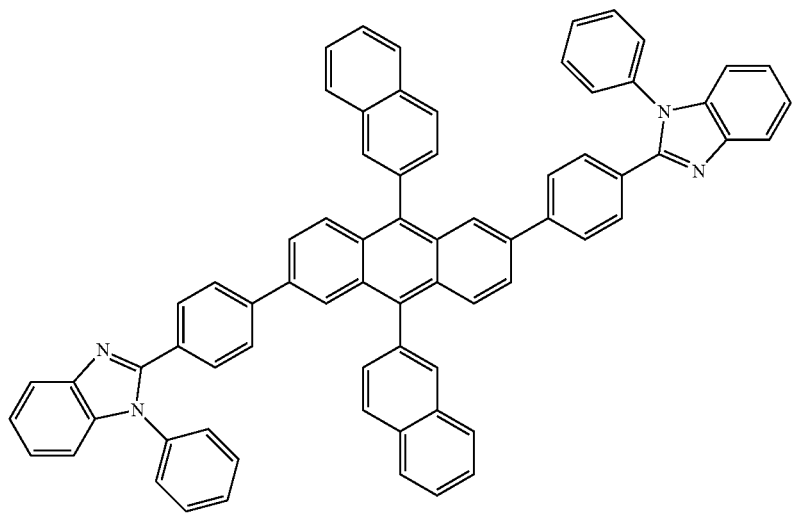
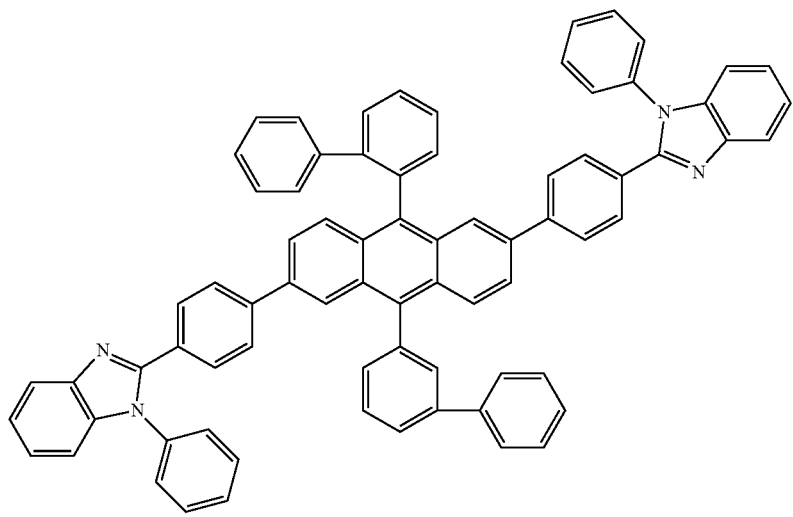
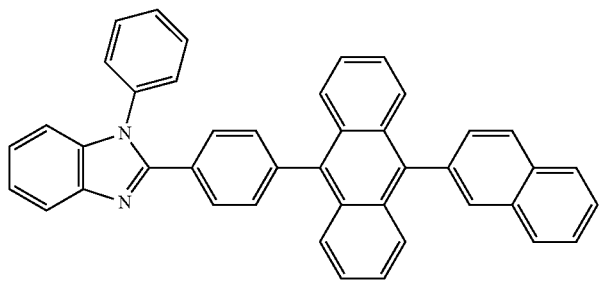

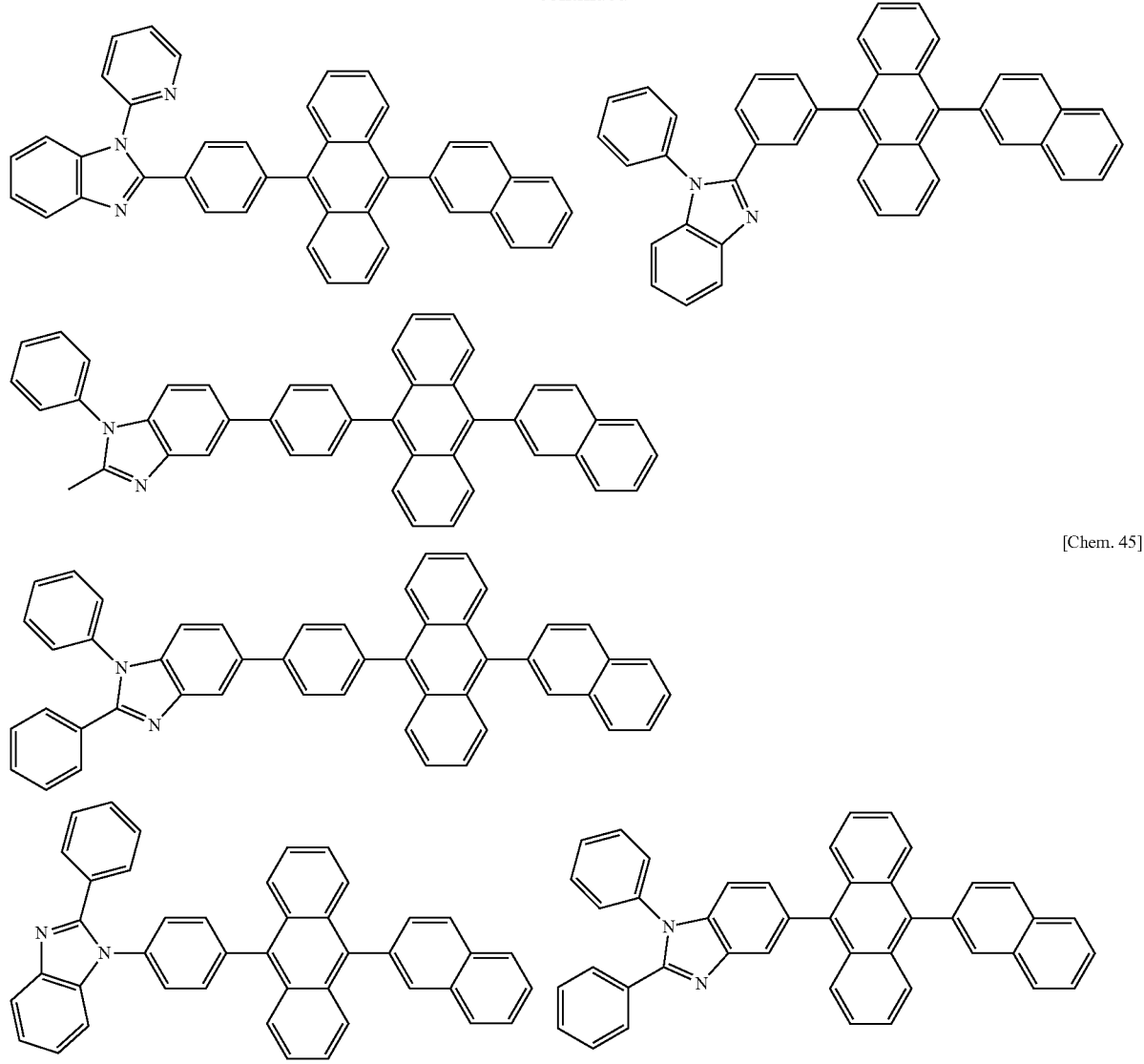

[Chem. 45]

The compound represented by the general formula (P) can be synthesized by the method described in WO 2003/060956 and WO 2004/080975. After the synthesis, purification is preferably carried out by column chromatography, recrystallization, reprecipitation, or the like, and then by sublimation purification. By the sublimation purification, organic impurities can be separated and inorganic salts, residual solvents, moisture, or the like can be removed effectively.

In the organic electroluminescent element of the present invention, the compound represented by the general formula (P) is preferably included in the organic layer between the light emitting layer and the cathode, and more preferably in the layer adjacent to the cathode.

The compound represented by the general formula (P) is preferably contained in the amount of 70% by mass to 100% by mass, and more preferably 85% by mass to 100% by mass, based on the total mass of the organic layer added.

Preferred examples of the material other than the material used in the electron injecting layer or the electron transporting layer in the organic electroluminescent element of the present invention include silole compounds described in JP-A-09-194487 or the like, phosphineoxide compounds described in JP-A-2006-73581 or the like, nitrogen-containing aromatic 6-membered ring hetero compounds described in JP-A-2005-276801, JP-A-2006-225320, WO 2005/085387, or the like, compounds having nitrogen-containing aromatic 6-membered hetero structures and carbazole structures, described in WO 2003/080760, WO 2005/085387, or the like, and aromatic hydrocarbon compounds described in US2009/0009065, WO 2010/134350, JP-T-2010-535806 (naphthalene compounds, anthracene compounds, triphenylene compounds, phenanthrene compounds, pyrene compounds, fluoranthene compounds, and the like).

<Protective Layer>

In the present invention, the entirety of the organic electroluminescent element may be protected by a protective layer.

For the protective layer, the detailed description in paragraph Nos. [0169] to [0170] of JP-A-2008-270736 can also be applied to the present invention. Incidentally, the materials for the protective layer may be either an inorganic material or an organic material.

<Sealing Enclosure>

For the organic electroluminescent element according to the present invention, the entirety of the element may be sealed using a sealing enclosure.

For the sealing enclosure, the detailed description in paragraph No. [0171] of JP-A-2008-270736 can be applied to the present invention.

<Driving Method>

The organic electroluminescent element of the present invention can emit light by applying a direct current (it may contain an alternate current component, if necessary) voltage (typically from 2 volts to 15 volts) or a direct current between the anode and the cathode.

As a driving method of the organic electroluminescent element of the present invention, driving methods described in JP-A-2-148687, JP-A-6-301355, JP-A-5-29080, JP-A-7-134558, JP-A-8-234685, and JP-A-8-241047, Japanese Patent No. 2784615, and U.S. Pat. Nos. 5,828,429 and 6,023,308 can be applied.

The external quantum efficiency of the organic electroluminescent element of the present invention is preferably 5% or more, more preferably 6% or more, and still more preferably 7% or more. As to the numerical value of the external quantum efficiency, a maximum value of the external quantum efficiency obtained when the organic electroluminescent element is driven at 20° C., or a value of the external quantum efficiency in the vicinity of from 300 $cd/m^2$ to 400 $cd/m^2$ obtained when the element is driven at 20° C. can be employed.

The internal quantum efficiency of the organic electroluminescent element of the present invention is preferably 30% or more, more preferably 50% or more, and still more preferably 70% or more. The internal quantum efficiency of the element is calculated by dividing the external quantum efficiency by the light extraction efficiency. The light extraction efficiency in usual organic EL elements is about 20%, but by taking into consideration the shape of a substrate, the shape of an electrode, the thickness of an organic layer, the thickness of an inorganic layer, the refractive index of an organic layer, the refractive index of an inorganic layer, or the like, it is possible to increase the light extraction efficiency to 20% or more.

<Light Emitting Wavelength>

In the organic electroluminescent element of the present invention, its light emitting wavelength is the same as the maximum light emitting wavelength of the material for the organic electroluminescent element of the present invention, and the element is used for blue light emission among the three primary colors of light. In the organic electroluminescent element of the present invention, the compound represented by the general formula (I) is subjected to blue light emission as the light emitting material.

<Use of Organic Electroluminescent Element of the Present Invention>

The organic electroluminescent element of the present invention can be suitably used for display elements, displays, backlights, electrophotography, illumination light sources, recording light sources, exposure light sources, readout light sources, signs, billboards, interior decorations, optical communications, and the like, and particularly preferably for devices driven in a region of high-intensity luminescence, such as a light emitting device, an illumination device, and a display device.

[Light Emitting Device]

The light emitting device of the present invention may include the organic electroluminescent element of the present invention.

Next, the light emitting device of the present invention will be described with reference to FIG. 2.

The light emitting device of the present invention is formed by using the organic electroluminescent element.

Figure 2:
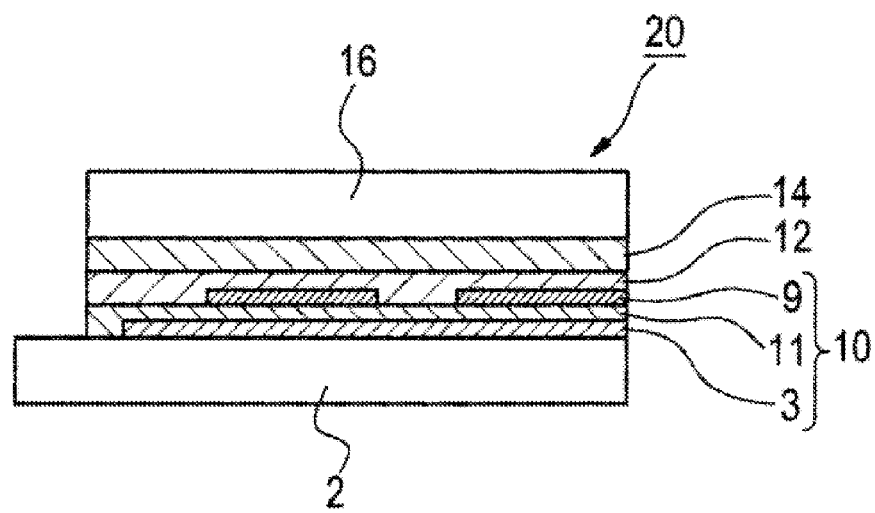
FIG. 2 is a schematic view showing one example of alight emitting device according to the present invention.

FIG. 2 is a cross-sectional view schematically showing one example of the light emitting device of the present invention. The light emitting device 20 in FIG. 2 includes a transparent substrate 2 (supporting substrate), an organic electroluminescent element 10, a sealing enclosure 16, and the like.

The organic electroluminescent element 10 is formed by laminating on the substrate 2 an anode 3 (first electrode), an organic layer 11, and a cathode 9 (second electrode) in this order. In addition, a protective layer 12 is laminated on the cathode 9, and a sealing enclosure 16 is further provided via an adhesive layer 14 on the protective layer 12. Incidentally, a part of each of the electrodes 3 and 9, a diaphragm, an insulating layer, and the like are omitted in FIG. 2.

Here, a photocurable adhesive such as an epoxy resin, or a thermosetting adhesive can be used for the adhesive layer 14, and for example, a thermosetting adhesive sheet may also be used as the adhesive layer 14.

The light emitting device of the present invention is not particularly limited in its use, and it can be used as not only an illumination device but also a display device of a television set, a personal computer, a mobile phone, electronic paper, or the like.

[Illumination Device]

The illumination device of the present invention includes the organic electroluminescent element of the present invention.

Next, the illumination device of the present invention will be described with reference to FIG. 3.

Figure 3:
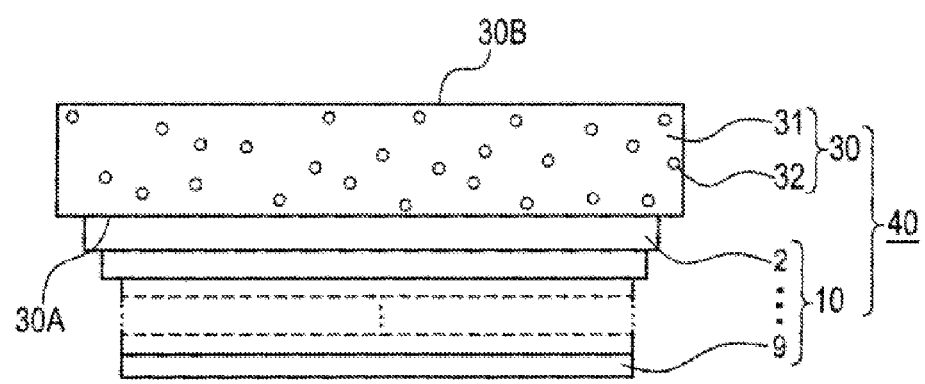
FIG. 3 is a schematic view showing one example of an illumination device according to the present invention.

FIG. 3 is a cross-sectional view schematically showing one example of the illumination device of the present invention. The illumination device 40 of the present invention includes, as shown in FIG. 3, the above-described organic EL element 10 and a light scattering member 30. More specifically, the illumination device 40 is configured such that the substrate 2 of the organic EL element 10 and the light scattering member 30 are in contact with each other.

The light scattering member 30 is not particularly limited as long as it can scatter light, but in FIG. 3, a member obtained by dispersing fine particles 32 in a transparent substrate 31 is used. Suitable examples of the transparent substrate 31 include a glass substrate, and suitable examples of the fine particles 32 include transparent resin fine particles. As the glass substrate and the transparent resin fine particles, a known product can be used for both. In such an illumination device 40, when light emitted from the organic electroluminescent element 10 is incident on the light incident surface 30A of the scattering member 30, the incident light is scattered by the light scattering member 30 and the scattered light is output as illuminating light from the light output surface 30B.

[Display Device]

The display device of the present invention may include the organic electroluminescent element of the present invention.

The display device of the present invention may be used for, for example, a display device of a television set, a personal computer, a mobile phone, electronic paper, or the like.

EXAMPLES

The characteristic features of the present invention are hereunder described in more detail with reference to the following Examples and Comparative Examples. The materials, use amounts, ratios, treatment details, treatment procedures, and the like shown in the following Examples and Comparative Examples can be appropriately modified so far as the gist of the present invention is not deviated. Accordingly, it should not be construed that the scope of the present invention is limited to the specific examples shown below.

The structural formulae of the compounds used in Examples and Comparative Examples are summarized below.

[Chem. 46]

Compound 1

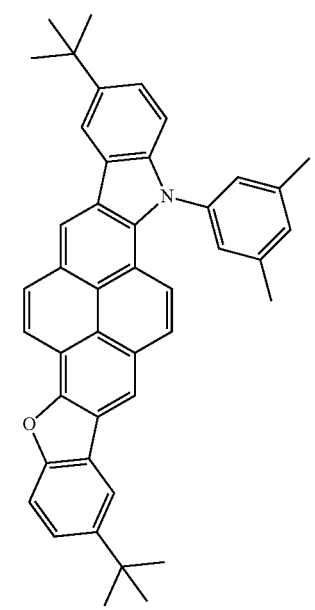

Compound 2

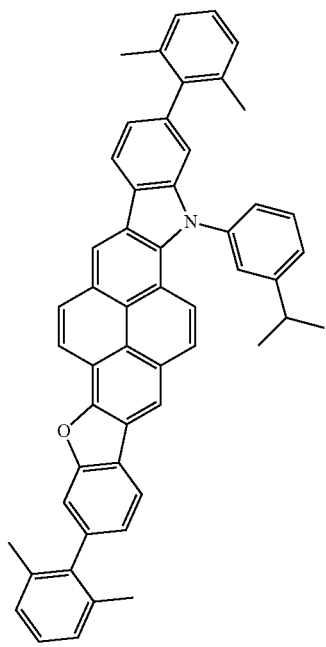

Compound 3

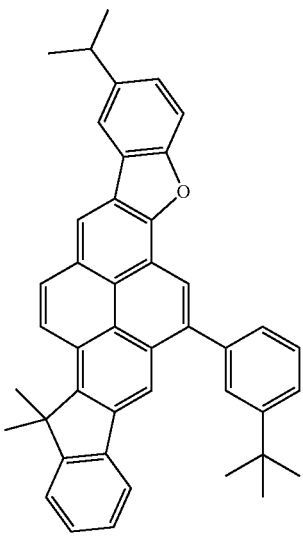

Compound 4

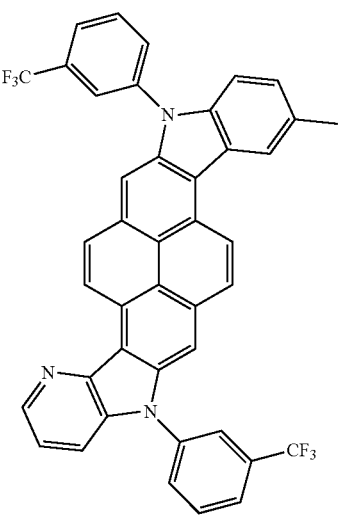

Compound 5

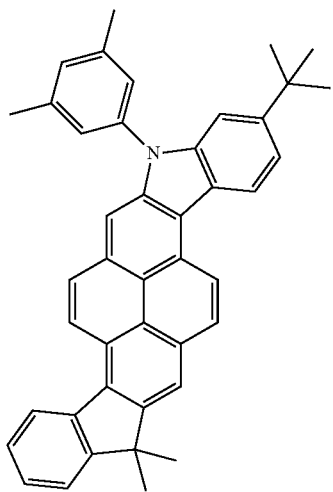

109
-continued
Compound 6
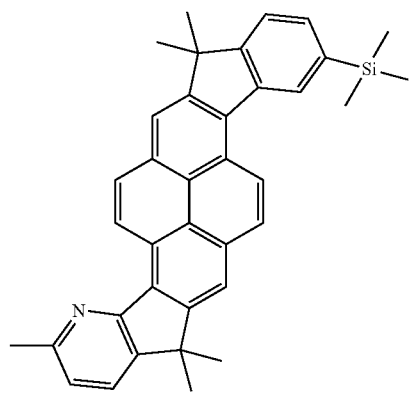
Compound 7
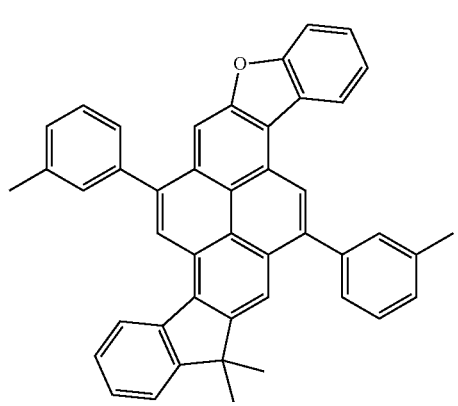
Compound 8
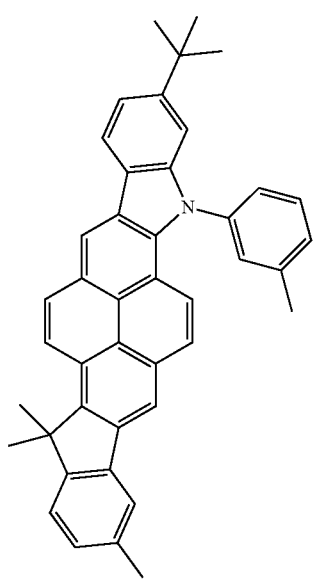
110
-continued
Comparative compound 1
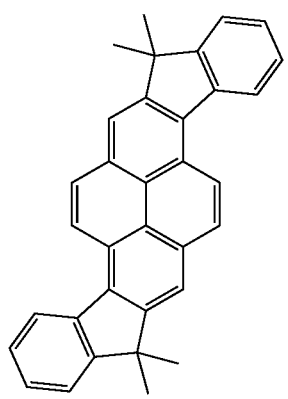
WO2010012328
Comparative compound 2
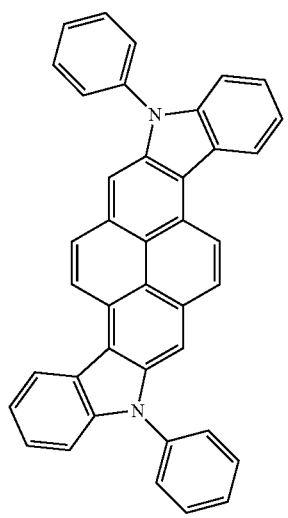
JP-2010-205986
KR20110006915
KR20110041726
Comparative compound 3
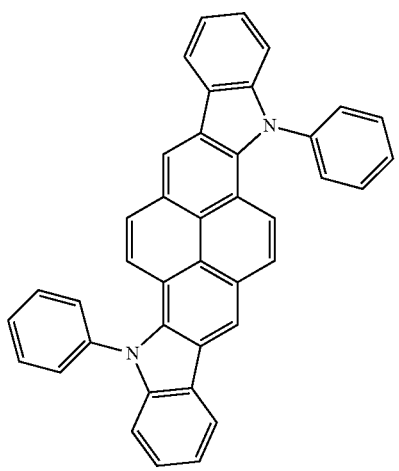
KR20100041726

[Chem. 47]
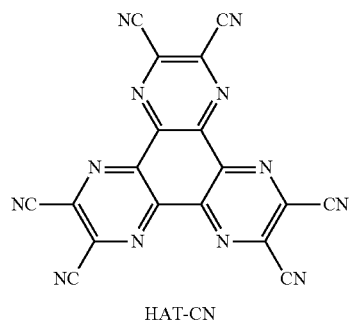
HAT-CN
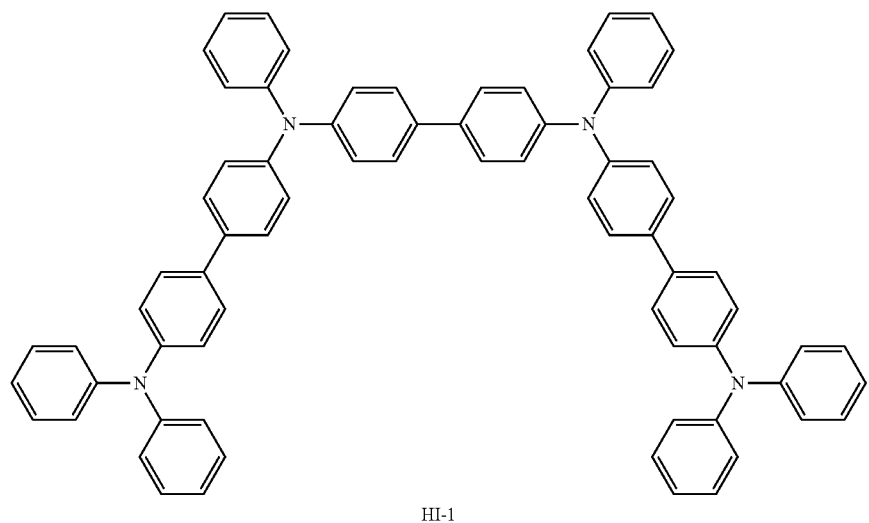
HI-1
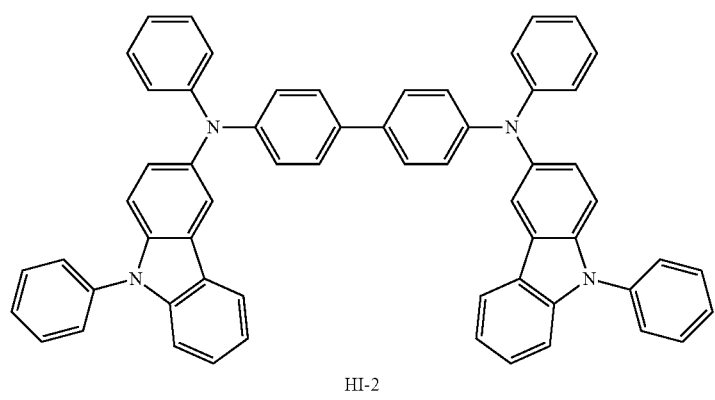
HI-2

-continued
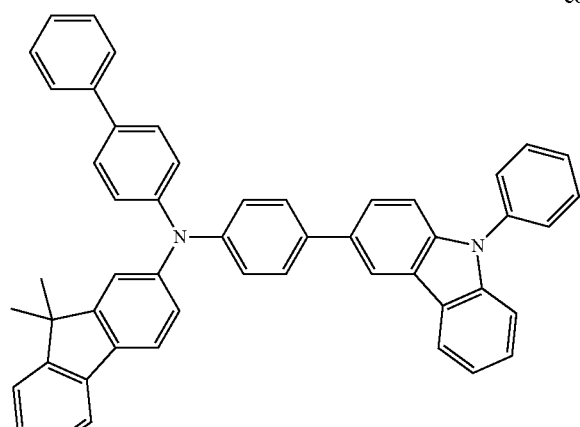
HT-1
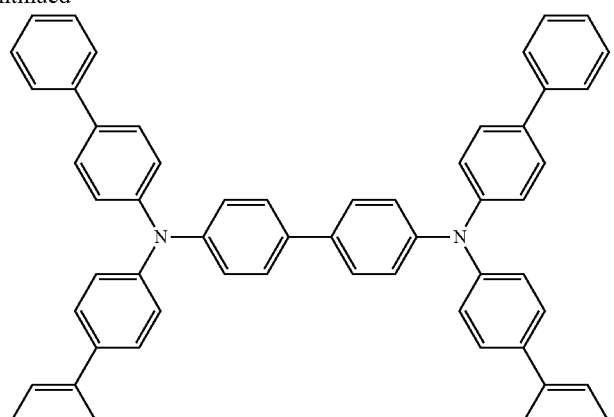
HT-2
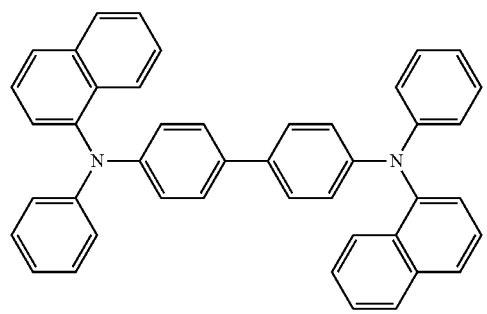
NPD
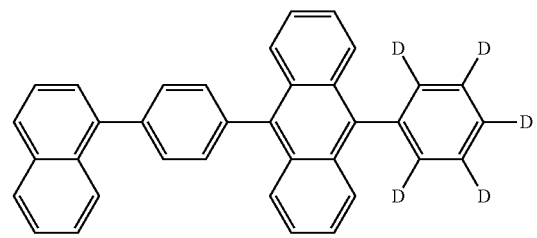
H-1
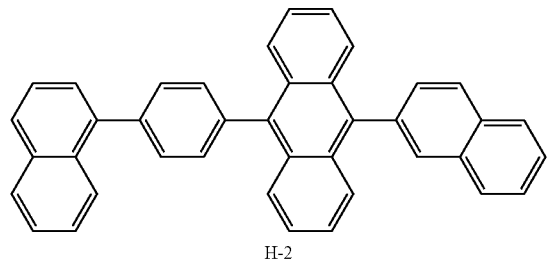
H-2
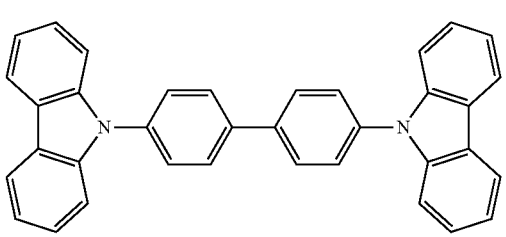
CBP
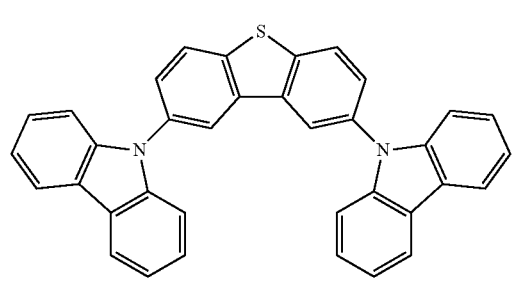
H-3
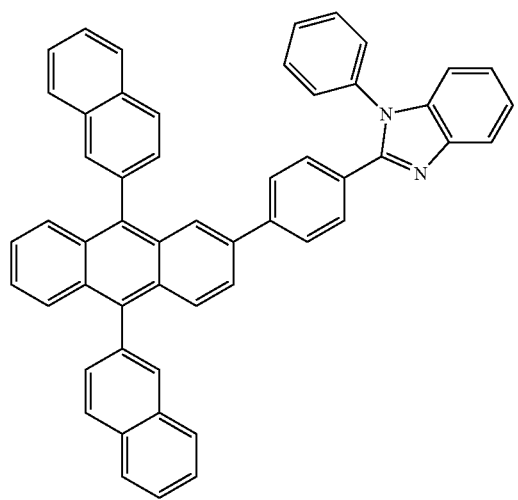
ET-1

-continued

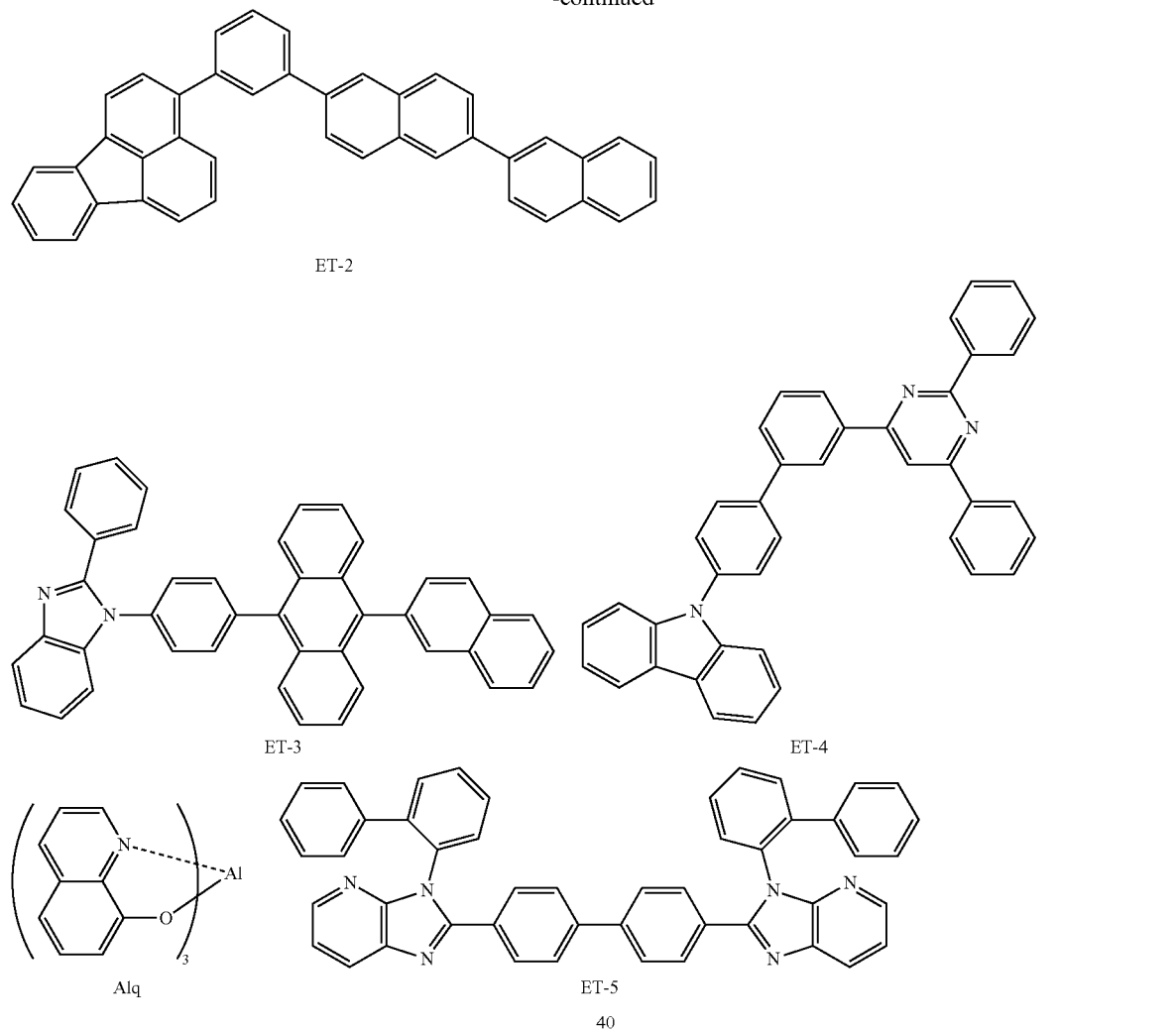

1. Synthesis Example

The compound represented by the general formula (I) can be synthesized by the method described in the present specification or a combination of other known reactions. Representative examples of the specific synthesis procedure of the compound represented by the general formula (I) will be described below.

(Synthesis Example 1) Synthesis of Compound 1

[Chem. 48]

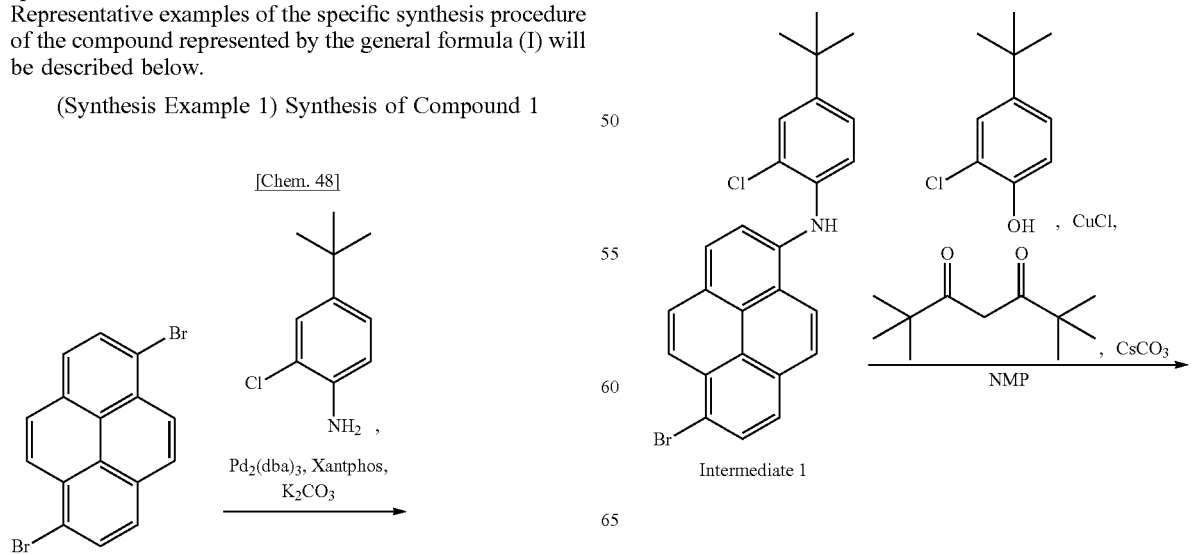

-continued

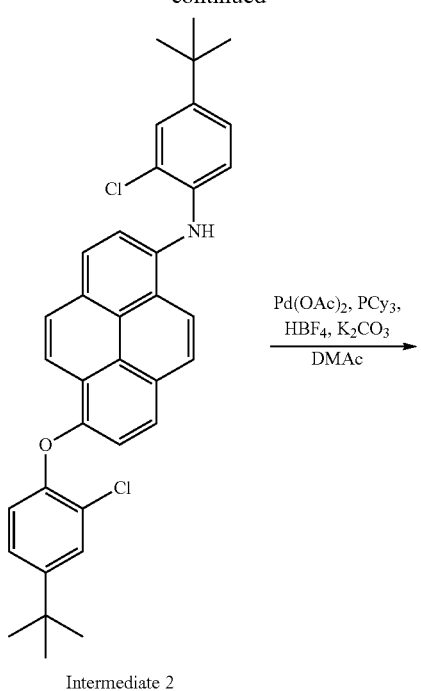

Intermediate 2

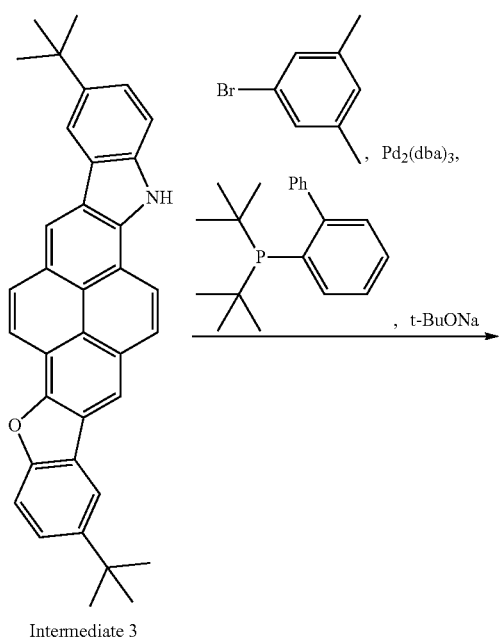

Intermediate 3

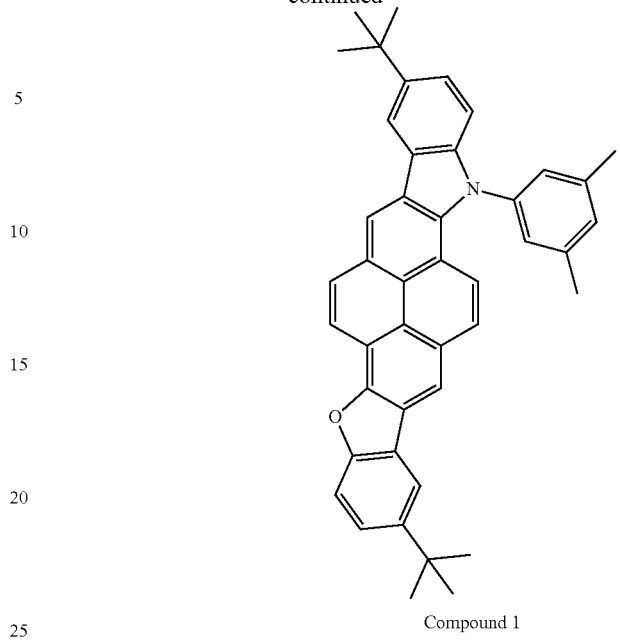

Compound 1

A synthesis intermediate 3 was synthesized according to the synthesis scheme with reference to well-known literatures. For the synthesis of the synthesis intermediate 2, reference may be made to [Org. Lett. 2002, 4, 1623-1626], and for the synthesis of the synthesis intermediate 3, reference may be made to [J. Am. Chem. Soc. 2006, 128, 581-590]. Subsequently, a compound 1 was synthesized by the following method.

900 mg (1.82 mmol) of the synthesis intermediate 3, 674 mg (3.64 mmol) of 1-bromo-3,5-dimethylbenzene, 168 mg (0.182 mmol) of tris(dibenzylideneacetone) dipalladium, 108 mg (0.364 mmol) of 2-(di-t-butylphosphino)biphenyl, 526 mg (5.48 mmol) of t-butoxysodium, and 20 mL of xylene were mixed, and heated and refluxed for 3 hours under a nitrogen atmosphere. The reaction liquid was purified by silica gel column chromatography (developing solvent: toluene) and further recrystallized with toluene/ethanol (1:4) to obtain 600 mg of compound 1 (yield 55%).

$^1$H NMR (400 MHz, in DMSO-d$_6$); δ (ppm)=9.32 (s, 1H), 8.92 (s, 1H), 8.60 (s, 1H), 8.50 (s, 2H), 8.45 (s, 1H), 8.09 (d, 1H), 7.87 (d, 1H), 7.74-7.64 (m, 3H), 7.41 (s, 1H), 7.32 (s, 2H), 7.19 (d, 1H), 2.46 (s, 6H), 1.49 (s, 9H), 1.47 (s, 9H) ppm.

The compounds 2 to 9 in Examples were synthesized by the similar method as for the compound 1. The comparative compounds 1 to 3 were synthesized with reference to well-known literatures in which each of the compounds is described.

Example 1

<Confirmation of Purity>

All of the materials used in the fabrication of the organic electroluminescent element were subjected to sublimation purification, and it was confirmed that the purity (absorption intensity area ratio at 254 nm) was 99.9% or more by using high performance liquid chromatography (TSKgel ODS-100Z, manufactured by Tosoh Corporation).

<Fabrication and Evaluation by Decomposition of Organic Electroluminescent Element>

A 0.5 mm-thick and 2.5 cm square glass substrate (manufactured by Geomatec Co., Ltd., surface resistance: 10Ω/□) having an ITO film thereon was put in a cleaning container. After ultrasonic cleaning in 2-propanol, the glass substrate was subjected to a UV-ozone treatment for 30 minutes. The following organic compound layers were deposited sequentially on this transparent anode (ITO film) by a vacuum deposition method.

First layer: HAT-CN: Film thickness 10 nm
Second layer: HT-1: Film thickness 30 nm
Third layer: H-2 and the light emitting material described in Table 1 (mass ratio=96:4): Film thickness 30 nm
Fourth layer: ET-1: Film thickness 30 nm 1 nm of lithium fluoride and 100 nm of metallic aluminum were deposited in this order thereon, thereby forming a cathode.

The obtained laminate was put in a glove box purged with a nitrogen gas without bringing it into contact with the atmosphere and then sealed with a sealing can made of glass and an ultraviolet ray-curable adhesive (XNR5516HV, manufactured by Nagase-Chiba Ltd.), thereby obtaining organic electroluminescent elements 1-1 to 1-10, and comparative organic electroluminescent elements 1-1 to 1-7, each having a light emitting area in a 2 mm×2 mm square. For each of the obtained organic electroluminescent elements, the tests below were carried out. The results of the evaluation from the viewpoint of the luminous efficiency, the color purity, and the change in the driving chromaticity are shown in Table 1.

(a) Color Purity

Light was emitted by applying a direct current voltage to each of the elements using a source measure unit 2400 manufactured by TOYO Corporation. The luminance was measured with a luminance meter (BM-8, manufactured by Topcon Corporation). The luminous spectrum and the light emitting wavelength were measured using a spectrum analyzer (PMA-11, manufactured by Hamamatsu Photonics K. K.). The chromaticity (x, y) was determined from the luminous spectrum when each of the organic electroluminescent elements was allowed to emit light to a luminance of 1000 cd/m² (CIE1931 color system). The y values at that time were evaluated as the following 3 grades according to the following criteria.

A: Less than 0.12
B: 0.12 or more and less than 0.18
C: 0.18 or more (b) Change in Driving Chromaticity Light was continuously emitted by applying a direct current voltage to each of the organic electroluminescent elements to a luminance of 1000 cd/m², and the chromaticity (x', y') when the luminance decreased to 500 cd/m² was measured from the luminous spectrum (CIE1931 color system). The change in the y values Δy (=|y'−Δy|) before and after the deterioration by driving was evaluated as the following 4 grades according to the following criteria.

A: Less than 0.01
B: 0.01 or more and less than 0.02
C: 0.02 or more and less than 0.03
D: 0.03 or more (c) Increase in Driving Voltage Light was continuously emitted by applying a direct current voltage to each of the organic electroluminescent elements to a luminance of 1000 cd/m², and the value of an increase in the voltage when the luminance decreased to 500 cd/m² was evaluated as the following 2 grades.

A: Less than 1.5 V
B: 1.5 V or more and less than 2.5 V
C: 2.5 V or more

TABLE 1

| Element No. | Light emitting material | Luminous color | Color purity | Change in driving chromaticity | Increase in driving voltage |
|---|---|---|---|---|---|
| Element 1-1 | Compound 1 | Blue | B | A | B |
| Element 1-2 | Compound 3 | Blue | B | A | B |
| Element 1-3 | Compound 4 | Blue | B | B | B |
| Element 1-4 | Compound 5 | Blue | B | A | B |
| Element 1-5 | Compound 7 | Blue | B | A | B |
| Element 1-6 | Compound 8 | Blue | B | A | B |
| Comparative element 1-1 | Comparative compound 1 | Blue | C | D | D |
| Comparative element 1-2 | Comparative compound 2 | Blue green | D | D | C |
| Comparative element 1-3 | Comparative compound 3 | Blue green | D | D | C |

Example 2

Organic electroluminescent elements were fabricated in the same manner as in Example 1, except that the layer configurations were changed as follows, and evaluations were carried out in the same manner as in Example 1. The results are shown in Table 2 below. Further, the luminous efficiency in Table 2 below is shown as a relative value, taking the external quantum efficiency of the comparative element 2-1 as 1.0.

First layer: HI-2: Film thickness 50 nm
Second layer: HT-2: Film thickness 45 nm
Third layer: H-3 and the light emitting material described in Table 2 (mass ratio=96:4): Film thickness 25 nm
Fourth layer: ET-2: Film thickness 5 nm
Fifth layer: ET-3: Film thickness 20 nm

TABLE 2

| Element No. | Light emitting material | Luminous color | Color purity | Change in driving chromaticity | Increase in driving voltage |
|---|---|---|---|---|---|
| Element 2-1 | Compound 2 | Blue | B | A | B |
| Element 2-2 | Compound 3 | Blue | B | A | B |
| Element 2-3 | Compound 5 | Blue | B | A | B |
| Element 2-4 | Compound 6 | Blue | B | B | B |
| Element 2-5 | Compound 9 | Blue | B | A | B |
| Comparative Element 2-1 | Comparative compound 1 | Blue | C | D | D |
| Comparative element 2-2 | Comparative compound 2 | Blue green | D | D | C |
| Comparative element 2-3 | Comparative compound 3 | Blue green | D | D | C |

Example 3

Organic electroluminescent elements were fabricated in the same manner as in Example 1, except that the layer configurations were changed as follows, and evaluations were carried out in the same manner as in Example 1. The results are shown in Table 3 below. Further, the luminous efficiency in Table 3 below is shown as a relative value, taking the external quantum efficiency of the comparative organic electroluminescent element 3-1 as 1.0.

First layer: HI-2: Film thickness 10 nm
Second layer: NPD: Film thickness 30 nm
Third layer: The host material and the light emitting material described in Table 3 (96:4): Film thickness 30 nm
Fourth layer: ET-4: Film thickness 10 nm
Fifth layer: The electron transporting material described in Table 3: Film thickness 20 nm

TABLE 3

| Element No. | Host material | Light emitting material | Electron transporting material | Luminous color | Color purity | Change in driving chromaticity | Increase in driving voltage |
|---|---|---|---|---|---|---|---|
| Element 3-1 | CBP | Compound 1 | ET-5 | Blue | B | A | B |
| Element 3-2 | H-3 | Compound 3 | Alq | Blue | B | A | B |
| Element 3-3 | H-3 | Compound 5 | ET-5 | Blue | B | A | B |
| Element 3-4 | CBP | Compound 7 | Alq | Blue | B | A | B |
| Element 3-5 | CBP | Compound 8 | ET-5 | Blue | B | A | B |
| Comparative element 3-1 | CBP | Comparative compound 1 | ET-5 | Blue | C | D | D |
| Comparative element 3-2 | CBP | Comparative compound 2 | ET-5 | Blue green | D | D | C |
| Comparative element 3-3 | H-3 | Comparative compound 3 | Alq | Blue green | D | D | C |

Example 4

Preparation of Light Emitting Layer-Forming Coating Liquids

A light emitting material 1 (0.25% by mass) and a host material ADN (5% by mass) were mixed with toluene (94.75% by mass) to obtain a light emitting layer-forming coating liquid 1.

Light emitting layer-forming coating liquids 2 and 3 were prepared in the same manner as for the light emitting layer-forming coating liquid 1, except that the light emitting material 1 in the light emitting layer-forming coating liquid 1 was changed to light emitting materials 4 and 6.

—Fabrication of Organic Electroluminescent Element—

ITO was deposited on a 25 mm×25 mm×0.7 mm glass substrate to give a thickness of 150 nm, thereby forming a film. The film was taken as a transparent supporting substrate. This transparent supporting substrate was etched and washed.

On this ITO glass substrate, 2 parts by mass of PTPDES-2 represented by the following structural formula (manufactured by Chemipro Kasei Kaisha, Ltd., Tg=205° C.) was dissolved in 98 parts by mass of cyclohexanone for the Electronics Industry (manufactured by Kanto Chemical Co., Inc.) and spin-coated (2,000 rpm, 20 seconds) to give a thickness of about 40 nm, and then dried at 120° C. for 30 minutes and subjected to an annealing treatment at 160° C. for 10 minutes to form a hole injecting layer.

PTPDES-2 represents the following structure.

[Chem. 49]

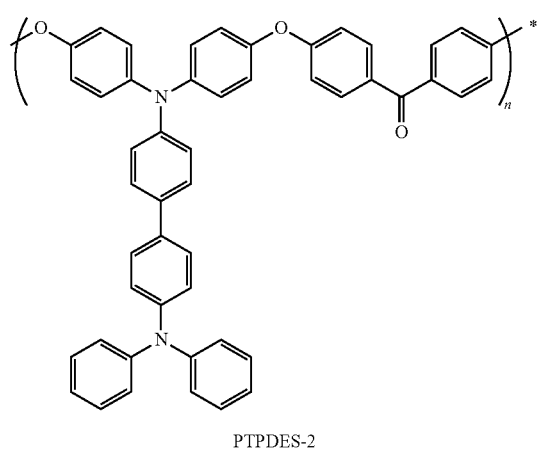

PTPDES-2

The light emitting layer-forming coating liquids 1 and 3 were spin-coated on the hole injecting layers (1,300 rpm, seconds) to give a thickness of about 40 nm, thereby obtaining light emitting layers.

Subsequently, BAlq represented by the following structural formula was formed as an electron transporting layer on a light emitting layer to give a thickness of 40 nm by a vacuum deposition method.

[Chem. 50]

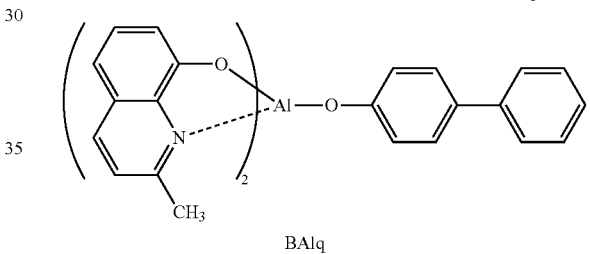

BAlq

Lithium fluoride (LiF) was formed as an electron injecting layer on an electron transporting layer to give a thickness of 1 nm by a vacuum deposition method. Metal aluminum was further deposited to 70 nm thereon to give a cathode.

The laminate thus prepared was put into a globe box purged with an argon gas, and then sealed with a sealing can made of stainless steel and an ultraviolet ray-curable adhesive (XNR5516HV, manufactured by Nagase-Chiba Ltd) to fabricate organic electroluminescent elements 4-1 to 4-3.

For the organic electroluminescent elements 4-1 to 4-3 and the comparative elements 4-1 to 4-2, the same evaluation as in Example 1 was carried out. The results are shown in Table 4 below.

TABLE 4

| Element No. | Light emitting material | Luminous color | Color purity | Change in driving chromaticity | Increase in driving voltage |
|---|---|---|---|---|---|
| Element 4-1 | Compound 1 | Blue | A | A | A |
| Element 4-2 | Compound 4 | Blue | A | A | A |
| Element 4-3 | Compound 6 | Blue | A | A | A |
| Comparative element 4-1 | Comparative compound 1 | Blue | B | C | C |
| Comparative element 4-2 | Comparative compound 2 | Blue green | C | C | C |

REFERENCE SIGNS LIST

2: SUBSTRATE
3: ANODE
4: HOLE INJECTING LAYER
5: HOLE TRANSPORTING LAYER
6: LIGHT EMITTING LAYER
7: HOLE BLOCKING LAYER
8: ELECTRON TRANSPORTING LAYER
9: CATHODE
10: ORGANIC ELECTROLUMINESCENT ELEMENT
11: ORGANIC LAYER
12: PROTECTIVE LAYER
14: ADHESIVE LAYER
16: SEALING ENCLOSURE
20: LIGHT EMITTING DEVICE
30: LIGHT SCATTERING MEMBER
31: TRANSPARENT SUBSTRATE
30A: LIGHT INCIDENT SURFACE
30B: LIGHT OUTPUTTING SURFACE
32: FINE PARTICLES
40: ILLUMINATION DEVICE

The invention claimed is:
1. An organic electroluminescent element comprising:
a substrate;
a pair of electrodes including an anode and a cathode, disposed on the substrate; and
at least one organic layer including a light emitting layer, disposed between the electrodes,
wherein at least one kind of compound represented by the following general formula (I) is contained in the any layer of the at least one organic layer:

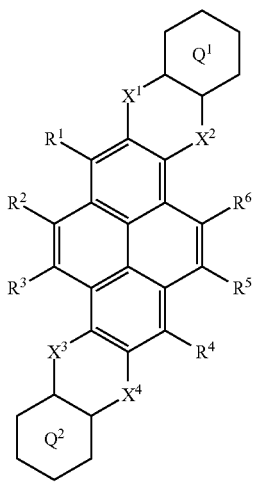

General formula (I)

$R^1$ to $R^6$ each independently represent a hydrogen atom or a substituent, but there is no case where two adjacent groups out of $R^1$ to $R^6$ are bonded to each other to form a ring; $Q^1$ and $Q^2$ each independently represent a 6-membered aromatic ring or a 6-membered nitrogen-containing aromatic heterocycle; a ring may be further fused with the 6-membered ring represented by $Q^1$ and $Q^2$; of $X^1$ to $X^4$, either each of $X^1$ and $X^4$ represents a single bond, and $X^2$ and $X^3$ each independently represents a linking group represented by any one of $CR^{51}R^{52}$, $NR^{53}$, O, S, and $SiR^{54}R^{55}$, or each of $X^2$ and $X^3$ represents a single bond, and $X^1$ and $X^4$ each independently represents a linking group represented by any one of $CR^{51}R^{52}$, $NR^{53}$, O, S, and $SiR^{54}R^{55}$; $R^{51}$ to $R^{55}$ each independently represents a hydrogen atom or a substituent; wherein general formula (I) satisfies at least one of the following conditions 1 and 2:
condition 1 in which the number of carbon atoms constituting the 6-membered aromatic ring or the 6-membered nitrogen-containing aromatic heterocycle of $Q^1$ and the number of carbon atoms constituting the 6-membered aromatic ring or the 6-membered nitrogen-containing aromatic heterocycle of $Q^2$ are different from each other;
with the proviso that when one of $Q^1$ or $Q^2$ is a pyridine group and the other is a phenyl group, $X^1$ and $X^4$ are $NR^{53}$, and each $R^{53}$ is a phenyl group, then at least one phenyl group of $R^{53}$ has at least one substituent; and
condition 2 in which the linking group represented by one of $X^1$ and $X^2$ and the linking group represented by one of $X^3$ and $X^4$ are different from each other.

2. The organic electroluminescent element according to claim 1, wherein the compound represented by the general formula (I) is a compound represented by the following general formula (II-1):

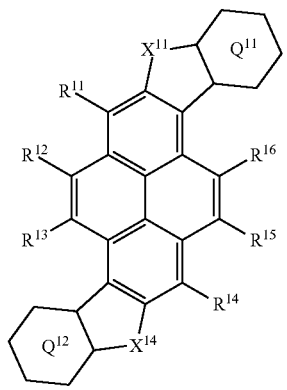

General formula (II-1)

wherein $R^{11}$ to $R^{16}$ each independently represents a hydrogen atom or a substituent, but there is no case where two adjacent groups out of $R^{11}$ to $R^{16}$ are bonded to each other to form a ring; $Q^{11}$ and $Q^{12}$ each independently represents a 6-membered aromatic ring or a 6-membered nitrogen-containing aromatic heterocycle; a ring may be further fused with the 6-membered ring represented by $Q^{11}$ and $Q^{12}$; $X^{11}$ and $X^{14}$ each independently represents a linking group represented by any one of $CR^{51}R^{52}$, $NR^{53}$, O, S, and $SiR^{54}R^{55}$; $R^{51}$ to $R^{55}$ each independently represents a hydrogen atom or a substituent; wherein general formula (II-1) satisfies at least one of the following conditions 1 and 2:
condition 1 in which the number of carbon atoms constituting the 6-membered aromatic ring or the 6-membered nitrogen-containing aromatic heterocycle of $Q^{11}$ and the number of carbon atoms constituting the 6-membered aromatic ring or the 6-membered nitrogen-containing aromatic heterocycle of $Q^{12}$ are different from each other;
with the proviso that when one of $Q^{11}$ or $Q^{12}$ is a pyridine group and the other is a phenyl group, $X^{11}$ and $X^{14}$ are $NR^{53}$, and each $R^{53}$ is a phenyl group, then at least one phenyl group of $R^{53}$ has at least one substituent; and condition 2 in which the linking group represented by $X^{11}$ and the linking group represented by $X^{14}$ are different from each other.

3. The organic electroluminescent element according to claim 2, wherein the compound represented by the general formula (II-1) is a compound represented by the following general formula (II-2):

General formula (II-2)

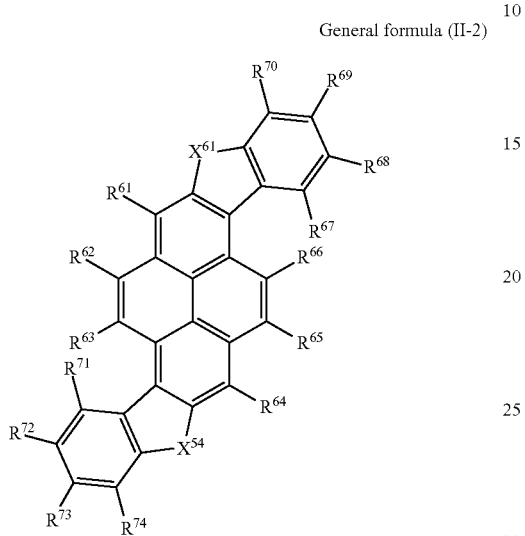

wherein $R^{61}$ to $R^{66}$ each independently represents a hydrogen atom or a substituent, but there is no case where two adjacent groups out of $R^{61}$ to $R^{66}$ are bonded to each other to form a ring; $R^{67}$ to $R^{74}$ each independently represents a hydrogen atom or a substituent, two adjacent groups out of $R^{67}$ to $R^{74}$ may be bonded to each other to form a ring structure, but the number of the rings thus formed is 2 or less; $X^{51}$ and $X^{54}$ each independently represents a linking group represented by any one of $CR^{51}R^{52}$, $NR^{53}$, O, S, and $SiR^{54}R^{55}$; $R^{51}$ to $R^{55}$ each independently represents a hydrogen atom or a substituent; wherein the linking group represented by $X^{51}$ and the linking group represented by $X^{54}$ are different from each other.

4. The organic electroluminescent element according to claim 3, wherein in the general formula (II-2), $X^{51}$ and $X^{54}$ each independently represent a linking group represented by any one of $CR^{51}R^{52}$, $NR^{53}$, and O.

5. The organic electroluminescent element according to claim 3, wherein in the general formula (II-2), any one of $X^{51}$ and $X^{54}$ is a linking group represented by $NR^{53}$, and the other is a linking group represented by any one of $CR^{51}R^{52}$ and O.

6. The organic electroluminescent element according to claim 3, wherein in the general formula (II-2), at least one of $R^{61}$ to $R^{74}$ and $R^{51}$ to $R^{55}$ is a substituent having any one of a fluorine atom, an alkyl group, a silyl group, an amino group, and a phenyl group or nitrogen-containing aromatic 6-membered ring having these groups.

7. The organic electroluminescent element according to claim 1, wherein the compound represented by the general formula (I) is a compound represented by the following general formula (III-1):

General formula (III-1)

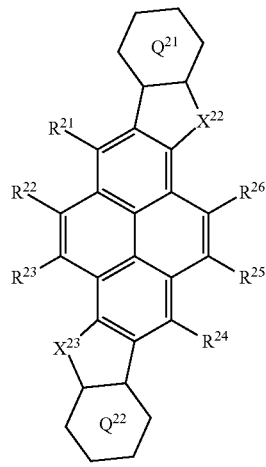

$R^{21}$ to $R^{26}$ each independently represents a hydrogen atom or a substituent, but there is no case where two adjacent groups out of $R^{51}$ to $R^{25}$ are bonded to each other to form a ring; $Q^{21}$ and $Q^{22}$ each independently represent a 6-membered aromatic ring or a 6-membered nitrogen-containing aromatic heterocycle; a ring may be further fused with the 6-membered ring represented by $Q^{12}$ and $Q^{22}$; $X^{22}$ and $X^{23}$ each independently represent a linking group represented by any one of $CR^{51}R^{52}$, $NR^{53}$, O, S, and $SiR^{54}R^{55}$; $R^{51}$ to $R^{55}$ each independently represent a hydrogen atom or a substituent; wherein general formula (III-1) satisfies at least one of the following conditions 1 and 2;

condition 1 in which the number of carbon atoms constituting the 6-membered aromatic ring or the 6-membered nitrogen-containing aromatic heterocycle of $Q^{21}$ and the number of carbon atoms constituting the 6-membered aromatic ring or the 6-membered nitrogen-containing aromatic heterocycle of $Q^{22}$ are different from each other;

condition 2 in which the linking group represented by $X^{22}$ and the linking group represented by $X^{23}$ are different from each other.

8. The organic electroluminescent element according to claim 7, wherein the compound represented by the general formula (III-1) is a compound represented by the following general formula (III-2):

General formula (III-2)

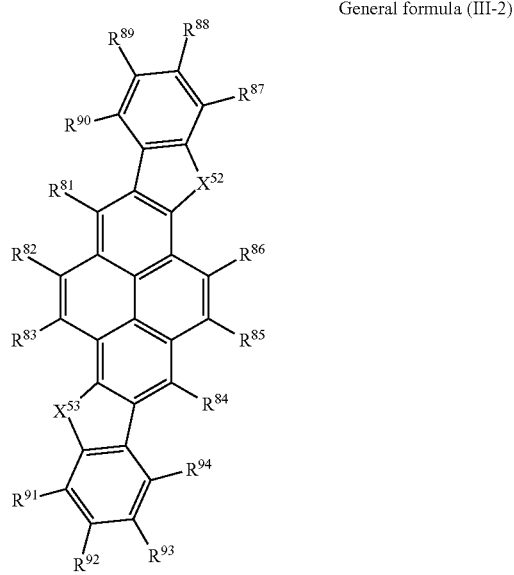

$R^{81}$ to $R^{86}$ each independently represent a hydrogen atom or a substituent, but there is no case where two adjacent groups out of $R^{61}$ to $R^{66}$ are bonded to each other to form a ring; $R^{87}$ to $R^{94}$ each independently represent a hydrogen atom or a substituent, two adjacent groups out of $R^{87}$ to $R^{94}$ may be bonded to each other to form a ring structure, but the number of the rings thus formed is 2 or less; $X^{51}$ and $X^{54}$ each independently represent a linking group represented by any one of $CR^{51}R^{52}$, $NR^{53}$, O, S, and $SiR^{54}R^{55}$; $R^{51}$ to $R^{55}$ each independently represent a hydrogen atom or a substituent; wherein the linking group represented by $X^{52}$ and the linking group represented by $X^{53}$ are different from each other.

9. The organic electroluminescent element according to claim 8, wherein in the general formula (III-2), $X^{52}$ and $X^{53}$ each independently represent a linking group represented by any one of $CR^{51}R^{52}$, $NR^{53}$, and O.

10. The organic electroluminescent element according to claim 8, wherein in the general formula (III-2), any one of $X^{52}$ and $X^{53}$ is a linking group represented by $NR^{53}$, and the other is a linking group represented by any one of $CR^{51}R^{52}$ and O.

11. The organic electroluminescent element according to claim 8, wherein in the general formula (III-2), at least one of $R^{81}$ to $R^{94}$ and $R^{51}$ to $R^{55}$ is a substituent having any one of a fluorine atom, an alkyl group, a silyl group, an amino group, and a phenyl group or nitrogen-containing aromatic 6-membered ring having these groups.

12. The organic electroluminescent element according to claim 1, wherein the compound represented by the general formula (I) is a compound represented by the following general formula (IV):

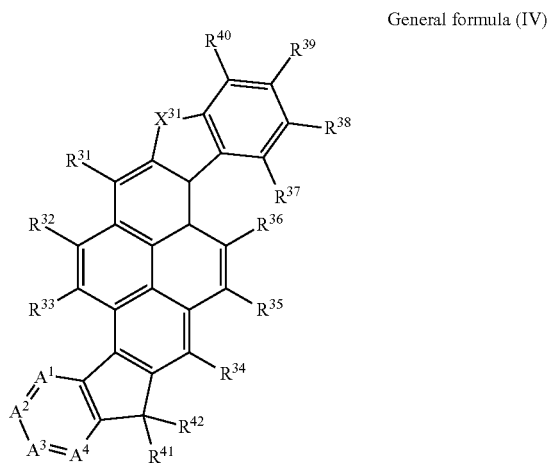

General formula (IV)

wherein $R^{31}$ to $R^{36}$ each independently represents a hydrogen atom or a substituent, but there is no case where two adjacent groups out of $R^{31}$ to $R^{36}$ are bonded to each other to form a ring; $R^{37}$ to $R^{40}$ each independently represents a hydrogen atom or a substituent, two adjacent groups out of $R^{37}$ to $R^{40}$ may be bonded to each other to form a ring structure, but the number of the rings thus formed is 2 or less; $R^{41}$ and $R^{42}$ each independently represent a hydrogen atom or a substituent; $A^1$ to $A^4$ each independently represent $CR^{56}$ or N, and at least one of $A^1$ to $A^4$ represents N; $R^{56}$ represents a hydrogen atom or a substituent, when two adjacent groups out of $A^1$ to $A^4$ are $CR^{56}$, the two $R^{56}$'s may be bonded to each other to form a ring structure, but the number of the rings thus formed is 2 or less; $X^{31}$ represents a linking group represented by any one of $NR^{53}$, O, S, and $SiR^{54}R^{55}$; $R^{53}$ to $R^{55}$ each independently represents a hydrogen atom or a substituent.

13. The organic electroluminescent element according to claim 1, wherein the molecular weight of the compound represented by the general formula (I) is 800 or less.

14. The organic electroluminescent element according to claim 1, wherein the compound represented by the general formula (I) is contained in the light emitting layer.

15. The organic electroluminescent element according to claim 14, wherein the compound represented by the general formula (I) is a light emitting material contained in the light emitting layer.

16. The organic electroluminescent element according to claim 15, wherein the light emitting layer further contains a host material.

17. The organic electroluminescent element according to claim 16, wherein the host material has a hydrocarbon fused ring structure having 10 to 50 carbon atoms.

18. The organic electroluminescent element according to claim 16, wherein the host material has an anthracene skeleton.

19. The organic electroluminescent element according to claim 1, wherein the organic layer containing the compound represented by the general formula (I) is formed by a vacuum deposition process.

20. The organic electroluminescent element according to claim 1, wherein the light emitting layer is formed by a wet process.

21. A light emitting device comprising the organic electroluminescent element according to claim 1.

22. A display device comprising the organic electroluminescent element according to claim 1.

23. An illumination device comprising the organic electroluminescent element according to claim 1.

24. A compound represented by the following general formula (I):

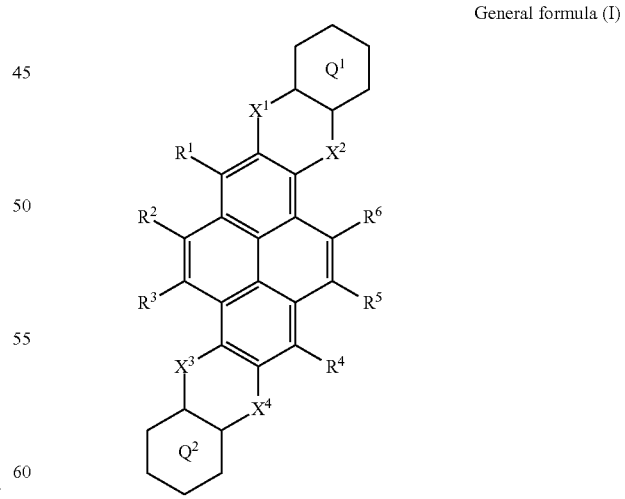

General formula (I)

wherein $R^1$ to $R^6$ each independently represent a hydrogen atom or a substituent, but there is no case where two adjacent groups out of $R^1$ to $R^6$ are bonded to each other to form a ring; $Q^1$ and $Q^2$ each independently represent a 6-membered aromatic ring or a 6-membered nitrogen-containing aromatic heterocycle; a ring may be further fused with the 6-membered ring represented by $Q^1$ and $Q^2$; of $X^1$ to $X^4$, either each of $X^1$ and $X^4$ represents a single bond, and $X^2$ and $X^3$ each independently represents a linking group represented by any one of $CR^{51}R^{52}$, $NR^{53}$, O, S, and $SiR^{54}R^{55}$, or each of $X^2$ and $X^3$ represents a single bond, and $X^1$ and $X^4$ each independently represents a linking group represented by any one of $CR^{51}R^{52}$, $NR^{53}$, O, S, and $SiR^{54}R^{55}$; $R^{51}$ to $R^{55}$ each independently represents a hydrogen atom or a substituent; wherein general formula (I) satisfies at least one of the following conditions 1 and 2:

condition 1 in which the number of carbon atoms constituting the 6-membered aromatic ring or the 6-membered nitrogen-containing aromatic heterocycle of $Q^1$ and the number of carbon atoms constituting the 6-membered aromatic ring or the 6-membered nitrogen-containing aromatic heterocycle of $Q^2$ are different from each other;

with the proviso that when one of $Q^1$ or $Q^2$ is a pyridine group and the other is a phenyl group, $X^1$ and $X^4$ are $NR^{53}$, and each $R^{53}$ is a phenyl group, then at least one phenyl group of $R^{53}$ has at least one substituent; and condition 2 in which the linking group represented by one of $X^1$ and $X^2$ and the linking group represented by one of $X^3$ and $X^4$ are different from each other;

with the provisos that when one of $X^1$ or $X^4$ is $NR^{53}$, the other of $X^1$ or $X^4$ is S, and $R^{53}$ is a substituted or unsubstituted phenyl group, then the compound represented by general formula (I) has at least one additional substituent;

when one of $X^1$ or $X^4$ is $NR^{53}$, the other of $X^1$ or $X^4$ is S, and $R^{53}$ is a substituted or unsubstituted alkyl group, then the compound represented by general formula (I) has at least one additional substituent selected from a fluorine atom, a silyl group and an amino group; and when $X^2$ is $NR^{53}$, $X^3$ is S, and $R^{53}$ is a substituted or unsubstituted alkyl group, then the compound represented by general formula (I) has at least one additional substituent.

* * * * *